US008741559B2

(12) United States Patent
Treiber et al.

(10) Patent No.: US 8,741,559 B2
(45) Date of Patent: Jun. 3, 2014

(54) CELLULAR ASSAY EMPLOYING DETECTABLE PROTEIN

(75) Inventors: Daniel Kelly Treiber, San Diego, CA (US); Warren G. Lewis, St. Louis, MO (US); Lisa M. Wodicka, San Diego, CA (US)

(73) Assignee: DiscoveRx Corporation, Fremont, CA (US)

( * ) Notice: Subject to any disclaimer, the term of this patent is extended or adjusted under 35 U.S.C. 154(b) by 0 days.

(21) Appl. No.: 13/265,806

(22) PCT Filed: Apr. 23, 2010

(86) PCT No.: PCT/US2010/032160
§ 371 (c)(1),
(2), (4) Date: Nov. 11, 2011

(87) PCT Pub. No.: WO2010/124157
PCT Pub. Date: Oct. 28, 2010

(65) Prior Publication Data
US 2012/0045769 A1    Feb. 23, 2012

Related U.S. Application Data

(60) Provisional application No. 61/172,680, filed on Apr. 24, 2009.

(51) Int. Cl.
*G01N 33/53* (2006.01)

(52) U.S. Cl.
USPC ............................................. 435/6.1; 435/7.1

(58) Field of Classification Search
None
See application file for complete search history.

(56) References Cited

U.S. PATENT DOCUMENTS 6,258,558 B1    7/2001   Szostak et al.
7,183,395 B2    2/2007   Mauro et al.

FOREIGN PATENT DOCUMENTS

| JP | 2005069788 A | 3/2005 |
| WO | 99/27092 A1 | 6/1999 |
| WO | 02/50259 A2 | 6/2002 |
| WO | 03/083435 A2 | 10/2003 |
| WO | 03/102221 A1 | 12/2003 |
| WO | 2004035732 A2 | 4/2004 |
| WO | 2008005310 A2 | 1/2008 |
| WO | 2008/147899 A1 | 12/2008 |

OTHER PUBLICATIONS

European Examination Report, Application No. 10714831.4-2402, Oct. 29, 2012.
Wang, et al., "Indentification of proteins bound to a thioaptamer probe on a proteomics array", Jun. 30, 2006, Biochemical and Biophysical Research Communications, 347, 586-593.
Nehyba, et al., "Differences in kB DNA-binding properties of v-Rel and c-Rel are the result of oncogenic mutations in three distinct functional regions of the Rel protein", Oncogene. 1997, 14, 2881-1897.

(Continued)

*Primary Examiner* — Jacob Cheu
(74) *Attorney, Agent, or Firm* — David J. Aston; Peters Verny, LLP

(57) ABSTRACT

Provided herein are assays useful, for example, for determining the activity of a protein involved in a cellular process. In some embodiments, the activity of the protein is assessed using a nucleic acid tag, and in particular, by detecting the presence of a nucleic acid tag. Such assays can be used, for example, to study the effects of test compounds as modulators, e.g., inhibitors, agonists and antagonists, of protein activity.

58 Claims, 7 Drawing Sheets

(56) References Cited

OTHER PUBLICATIONS

Figure 1:
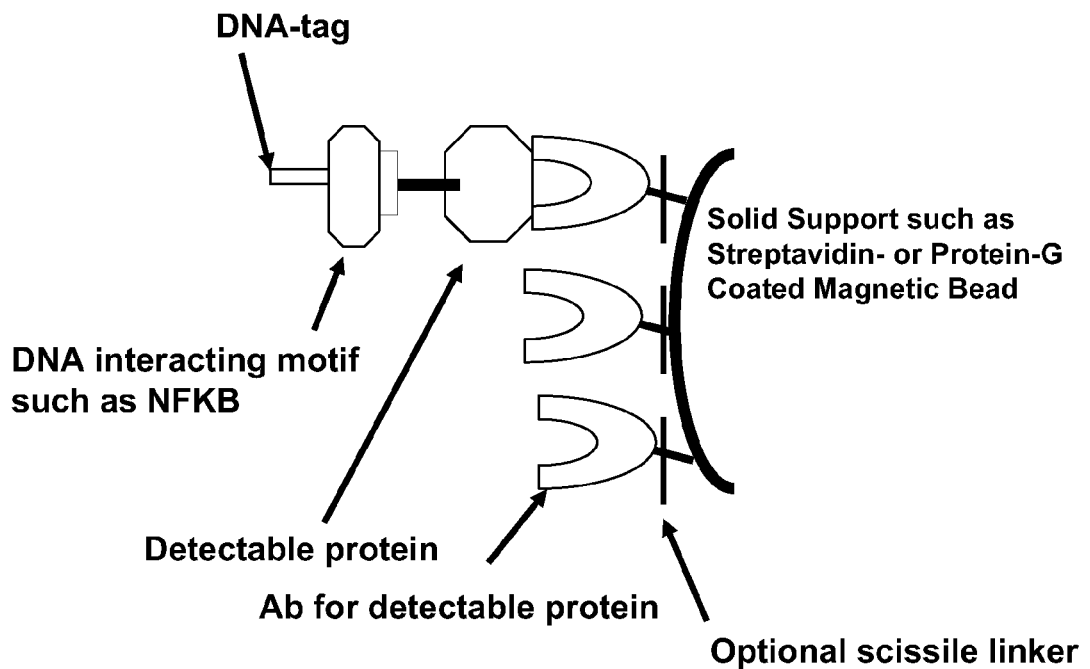

Fabian, et al., "A small molecule-kinase interaction map for clinical kinase inhibitors", Nature Biotechnology, vol. 23, No. 3, Mar. 2005, pp. 329-336.

Kuprash, et al,. "Homodimer of p50 (NFIB1) does not introduce a substantial directed bend into DNA according to three different experimental assays", Nucleic Acids Research, 1995, vol. 23, No. 3, pp. 427-433.

Escalante, et al., "Structure of IRF-1 with bound DNA reveals determinants of interferon regulation", Nature, vol. 391, Jan. 1998, pp. 103-106.

Seong, et al., "Atomic force microscopy identification of transcription factor NFkB bound to streptavidin-pin-holding DNA probe", Analytical Biochemistry 309 (2002) 241-247.

Traxler, et al. (Expert Opin Ther Targ, 2003, 7(2):215-234).

Roberts, et al., (PNAS, 1997, vol. 94, p. 12297-12302).

Basu, et al., (Mol. Cell Biol., 1997, 17(2):677-686).

International Search Report for PCT/US2007/015089, dated Jun. 23, 2008, 12 pp.

Roberts, et al., "The mouse proline-rich protein MP6 promoter binds isoprenaline-inducible parotid nuclear proteins via a hightly conserved NFkB/rel-like site", Nucleic Acids Research, vol. 19(19):5205-5211 (1991).

Schweitzer, et al., "Immunoassays with rolling circle DNA amplification: A versatile platform for ultrasensitive antigen detection," Proc. Natl. Assoc. Sci. 97: 10113-10119 (2000).

Wiltshire, et al., "Detection of multiple allergen-specific IgEs on microarrays by immunoassay with rolling circle amplification", Clinical Chemistry, 46:1900-1993 (2000).

International Search Report for PCT/US2010/124157, dated Jul. 29, 2010, 5 pp.

JP2005069788, published Mar. 17, 2005, machine translation prepared Jan. 8, 2014.

SEQUENCE LISTING

```
<160> NUMBER OF SEQ ID NOS: 34

<210> SEQ ID NO 1
<211> LENGTH: 98
<212> TYPE: DNA
<213> ORGANISM: Artificial Sequence
<220> FEATURE:
<223> OTHER INFORMATION: Nucleic acid oligomer for NF-kB binding

<400> SEQUENCE: 1
ttgtgaattg ctgaccgtag atgtcaactt tgaccatcag acaacgtttc tccattccaa    60
ttatgcgaga atcctaggga attccctag atcgcatg                            98

<210> SEQ ID NO 2
<211> LENGTH: 90
<212> TYPE: DNA
<213> ORGANISM: Artificial Sequence
<220> FEATURE:
<223> OTHER INFORMATION: Nucleic acid oligomer for NF-kB binding

<400> SEQUENCE: 2
cggcgtaaaa acgaatacca tgtctctcat cgctcgactc attctttcca aaatttcgcg    60
gaaccagggg gaattcccct agatcgcatg                                    90

<210> SEQ ID NO 3
<211> LENGTH: 94
<212> TYPE: DNA
<213> ORGANISM: Artificial Sequence
<220> FEATURE:
<223> OTHER INFORMATION: Nucleic acid oligomer for NF-kB binding

<400> SEQUENCE: 3
aaacaatgag acaccaggga ttagatatca gtacaatgtg cttccacaaa ggatcaccag    60
caatattcca aagggaattc ccctagatcg catg                               94

<210> SEQ ID NO 4
<211> LENGTH: 107
<212> TYPE: DNA
<213> ORGANISM: Artificial Sequence
<220> FEATURE:
<223> OTHER INFORMATION: Nucleic acid oligomer for GAL4 binding
```

```
<400> SEQUENCE: 4
catgcgacag cggagttacg tccagaagga caacatcttt gacatcgcct cttgaattgc     60
tgcaccaagg gctactgccg gagtactgtc ctccgctaga tcgcatg                 107

<210> SEQ ID NO 5
<211> LENGTH: 322
<212> TYPE: PRT
<213> ORGANISM: Artificial Sequence
<220> FEATURE:
<223> OTHER INFORMATION: NF-kB DNA binding domain

<400> SEQUENCE: 5

Met Ala Gly Pro Tyr Leu Gln Ile Leu Glu Gln Pro Lys Gln Arg Gly
  1               5                  10                  15

Phe Arg Phe Arg Tyr Val Cys Glu Gly Pro Ser His Gly Gly Leu Pro
                 20                  25                  30

Gly Ala Ser Ser Glu Lys Asn Lys Ser Tyr Pro Gln Val Lys Ile
             35                  40                  45

Cys Asn Tyr Val Gly Pro Ala Lys Val Ile Val Gln Leu Val Thr Asn
     50                  55                  60

Gly Lys Asn Ile His Leu His Ala His Ser Leu Val Gly Lys His Cys
 65                  70                  75                  80

Glu Asp Gly Ile Cys Thr Val Thr Ala Gly Pro Lys Asp Met Val Val
                 85                  90                  95

Gly Phe Ala Asn Leu Gly Ile Leu His Val Thr Lys Lys Lys Val Phe
                100                 105                 110

Glu Thr Leu Glu Ala Arg Met Thr Glu Ala Cys Ile Arg Gly Tyr Asn
            115                 120                 125

Pro Gly Leu Leu Val His Pro Asp Leu Ala Tyr Leu Gln Ala Glu Gly
        130                 135                 140

Gly Gly Asp Arg Gln Leu Gly Asp Arg Glu Lys Glu Leu Ile Arg Gln
145                 150                 155                 160

Ala Ala Leu Gln Gln Thr Lys Glu Met Asp Leu Ser Val Val Arg Leu
                165                 170                 175

Met Phe Thr Ala Phe Leu Pro Asp Ser Thr Gly Ser Phe Thr Arg Arg
                180                 185                 190

Leu Glu Pro Val Val Ser Asp Ala Ile Tyr Asp Ser Lys Ala Pro Asn
            195                 200                 205

Ala Ser Asn Leu Lys Ile Val Arg Met Asp Arg Thr Ala Gly Cys Val
        210                 215                 220

Thr Gly Gly Glu Glu Ile Tyr Leu Leu Cys Asp Lys Val Gln Lys Asp
225                 230                 235                 240

Asp Ile Gln Ile Arg Phe Tyr Glu Glu Glu Asn Gly Gly Val Trp
                245                 250                 255

Glu Gly Phe Gly Asp Phe Ser Pro Thr Asp Val His Arg Gln Phe Ala
                260                 265                 270

Ile Val Phe Lys Thr Pro Lys Tyr Lys Asp Ile Asn Ile Thr Lys Pro
                275                 280                 285

Ala Ser Val Phe Val Gln Leu Arg Arg Lys Ser Asp Leu Glu Thr Ser
            290                 295                 300

Glu Pro Lys Pro Phe Leu Tyr Tyr Pro Glu Ile Lys Asp Lys Glu Glu
305                 310                 315                 320

Val Asp

<210> SEQ ID NO 6
```

```
<211> LENGTH: 147
<212> TYPE: PRT
<213> ORGANISM: Artificial Sequence
<220> FEATURE:
<223> OTHER INFORMATION: GAL4 DNA binding domain

<400> SEQUENCE: 6

Met Lys Leu Leu Ser Ser Ile Glu Gln Ala Cys Asp Ile Cys Arg Leu
  1               5                  10                  15

Lys Lys Leu Lys Cys Ser Lys Glu Lys Pro Lys Cys Ala Lys Cys Leu
             20                  25                  30

Lys Asn Asn Trp Glu Cys Arg Tyr Ser Pro Lys Thr Lys Arg Ser Pro
         35                  40                  45

Leu Thr Arg Ala His Leu Thr Glu Val Glu Ser Arg Leu Glu Arg Leu
 50                  55                  60

Glu Gln Leu Phe Leu Leu Ile Phe Pro Arg Glu Asp Leu Asp Met Ile
 65                  70                  75                  80

Leu Lys Met Asp Ser Leu Gln Asp Ile Lys Ala Leu Leu Thr Gly Leu
                 85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser
145

<210> SEQ ID NO 7
<211> LENGTH: 10
<212> TYPE: DNA
<213> ORGANISM: Artificial Sequence
<220> FEATURE:
<223> OTHER INFORMATION: NF-kB recognition sequence

<400> SEQUENCE: 7
gggaattccc                                                          10

<210> SEQ ID NO 8
<211> LENGTH: 11
<212> TYPE: DNA
<213> ORGANISM: Artificial Sequence
<220> FEATURE:
<223> OTHER INFORMATION: NF-kB recognition sequence

<400> SEQUENCE: 8
gggaaattcc c                                                        11

<210> SEQ ID NO 9
<211> LENGTH: 10
<212> TYPE: DNA
<213> ORGANISM: Artificial Sequence
<220> FEATURE:
<223> OTHER INFORMATION: NF-kB recognition sequence

<400> SEQUENCE: 9
gggactttcc                                                          10

<210> SEQ ID NO 10
<211> LENGTH: 10
<212> TYPE: DNA
<213> ORGANISM: Artificial Sequence
<220> FEATURE:
```

```
<223> OTHER INFORMATION: NF-kB consensus sequence
<220> FEATURE:
<221> NAME/KEY: variation
<222> LOCATION: 4
<223> OTHER INFORMATION: n=purine
<220> FEATURE:
<221> NAME/KEY: variation
<222> LOCATION: (5)...(6)
<223> OTHER INFORMATION: n=any nucleotide
<220> FEATURE:
<221> NAME/KEY: variation
<222> LOCATION: (7)...(8)
<223> OTHER INFORMATION: n=pyrimidine

<400> SEQUENCE: 10 gggnnnnncc                                                          10

<210> SEQ ID NO 11
<211> LENGTH: 17
<212> TYPE: DNA
<213> ORGANISM: Artificial Sequence
<220> FEATURE:
<223> OTHER INFORMATION: Gal4 recognition sequence

<400> SEQUENCE: 11
cggagtactg tcctccg                                                  17

<210> SEQ ID NO 12
<211> LENGTH: 17
<212> TYPE: DNA
<213> ORGANISM: Artificial Sequence
<220> FEATURE:
<223> OTHER INFORMATION: Gal4 consensus sequence
<220> FEATURE:
<221> NAME/KEY: variation
<222> LOCATION: (4)...(14)
<223> OTHER INFORMATION: n=any nucleotide

<400> SEQUENCE: 12
cggnnnnnnn nnnnccg                                                  17

<210> SEQ ID NO 13
<211> LENGTH: 10
<212> TYPE: DNA
<213> ORGANISM: Artificial Sequence
<220> FEATURE:
<223> OTHER INFORMATION: RelA/c-Rel consensus sequence
<220> FEATURE:
<221> NAME/KEY: variation
<222> LOCATION: 1
<223> OTHER INFORMATION: n=a, c or t
<220> FEATURE:
<221> NAME/KEY: variation
<222> LOCATION: 5
<223> OTHER INFORMATION: n=purine
<220> FEATURE:
<221> NAME/KEY: variation
<222> LOCATION: 6
<223> OTHER INFORMATION: n=any nucleotide
<220> FEATURE:
<221> NAME/KEY: variation
<222> LOCATION: (7)...(8)
<223> OTHER INFORMATION: n=pyrimidine

<400> SEQUENCE: 13 nggannnncc                                                          10

<210> SEQ ID NO 14
<211> LENGTH: 21
<212> TYPE: DNA
<213> ORGANISM: Artificial Sequence
<220> FEATURE:
```

<223> OTHER INFORMATION: Cro repressor recognition sequence

<400> SEQUENCE: 14
tctatcaccg cgggtgataa a                                            21

<210> SEQ ID NO 15
<211> LENGTH: 21
<212> TYPE: DNA
<213> ORGANISM: Artificial Sequence
<220> FEATURE:
<223> OTHER INFORMATION: Lac repressor recognition sequence

<400> SEQUENCE: 15
gaattgtgag cgctcacaat t                                            21

<210> SEQ ID NO 16
<211> LENGTH: 10
<212> TYPE: DNA
<213> ORGANISM: Artificial Sequence
<220> FEATURE:
<223> OTHER INFORMATION: GCN4 recognition sequence

<400> SEQUENCE: 16
agtgactcat                                                         10

<210> SEQ ID NO 17
<211> LENGTH: 22
<212> TYPE: DNA
<213> ORGANISM: Artificial Sequence
<220> FEATURE:
<223> OTHER INFORMATION: Opaque-2 recognition sequence

<400> SEQUENCE: 17
tgtcattcca cgtagatgaa aa                                           22

<210> SEQ ID NO 18
<211> LENGTH: 10
<212> TYPE: DNA
<213> ORGANISM: Artificial Sequence
<220> FEATURE:
<223> OTHER INFORMATION: Opaque-2 recognition sequence

<400> SEQUENCE: 18
tccacgtaga                                                         10

<210> SEQ ID NO 19
<211> LENGTH: 16
<212> TYPE: DNA
<213> ORGANISM: Artificial Sequence
<220> FEATURE:
<223> OTHER INFORMATION: Lex-A recognition sequence

<400> SEQUENCE: 19
ctgtatatat atacag                                                  16

<210> SEQ ID NO 20
<211> LENGTH: 6
<212> TYPE: DNA
<213> ORGANISM: Artificial Sequence
<220> FEATURE:
<223> OTHER INFORMATION: TGA1a recognition sequence

<400> SEQUENCE: 20 gacgtc                                                              6

<210> SEQ ID NO 21

```
<211> LENGTH: 10
<212> TYPE: DNA
<213> ORGANISM: Artificial Sequence
<220> FEATURE:
<223> OTHER INFORMATION: EGR-1 or Zif 268  recognition sequence

<400> SEQUENCE: 21
gcgtgggcgt                                                                    10

<210> SEQ ID NO 22
<211> LENGTH: 393
<212> TYPE: PRT
<213> ORGANISM: Homo sapiens

<400> SEQUENCE: 22

Met Pro Lys Lys Lys Pro Thr Pro Ile Gln Leu Asn Pro Ala Pro Asp
 1               5                  10                  15

Gly Ser Ala Val Asn Gly Thr Ser Ala Glu Thr Asn Leu Glu Ala
             20                  25                  30

Leu Gln Lys Lys Leu Glu Glu Leu Glu Leu Asp Glu Gln Gln Arg Lys
             35                  40                  45

Arg Leu Glu Ala Phe Leu Thr Gln Lys Gln Lys Val Gly Glu Leu Lys
 50                  55                  60

Asp Asp Asp Phe Glu Lys Ile Ser Glu Leu Gly Ala Gly Asn Gly Gly
65                   70                  75                  80

Val Val Phe Lys Val Ser His Lys Pro Ser Gly Leu Val Met Ala Arg
                 85                  90                  95

Lys Leu Ile His Leu Glu Ile Lys Pro Ala Ile Arg Asn Gln Ile Ile
             100                 105                 110

Arg Glu Leu Gln Val Leu His Glu Cys Asn Ser Pro Tyr Ile Val Gly
         115                 120                 125

Phe Tyr Gly Ala Phe Tyr Ser Asp Gly Glu Ile Ser Ile Cys Met Glu
    130                 135                 140

His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
                165                 170                 175

Leu Thr Tyr Leu Arg Glu Lys His Lys Ile Met His Arg Asp Val Lys
            180                 185                 190

Pro Ser Asn Ile Leu Val Asn Ser Arg Gly Glu Ile Lys Leu Cys Asp
        195                 200                 205

Phe Gly Val Ser Gly Gln Leu Ile Asp Ser Met Ala Asn Ser Phe Val
    210                 215                 220

Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
                245                 250                 255

Ala Val Gly Arg Tyr Pro Ile Pro Pro Asp Ala Lys Glu Leu Glu
            260                 265                 270

Leu Met Phe Gly Cys Gln Val Glu Gly Asp Ala Ala Glu Thr Pro Pro
        275                 280                 285

Arg Pro Arg Thr Pro Gly Arg Pro Leu Ser Ser Tyr Gly Met Asp Ser
    290                 295                 300

Arg Pro Pro Met Ala Ile Phe Glu Leu Leu Asp Tyr Ile Val Asn Glu
305                 310                 315                 320

Pro Pro Pro Lys Leu Pro Ser Gly Val Phe Ser Leu Glu Phe Gln Asp
                325                 330                 335
```

```
Phe Val Asn Lys Cys Leu Ile Lys Asn Pro Ala Glu Arg Ala Asp Leu
                340                 345                 350

Lys Gln Leu Met Val His Ala Phe Ile Lys Arg Ser Asp Ala Glu Glu
            355                 360                 365

Val Asp Phe Ala Gly Trp Leu Cys Ser Thr Ile Gly Leu Asn Gln Pro
370                 375                 380

Ser Thr Pro Thr His Ala Ala Gly Val
385                 390

<210> SEQ ID NO 23
<211> LENGTH: 379
<212> TYPE: PRT
<213> ORGANISM: Homo sapiens

<400> SEQUENCE: 23

Met Ala Ala Ala Ala Gln Gly Gly Gly Gly Glu Pro Arg Arg
  1               5                  10                  15

Thr Glu Gly Val Gly Pro Gly Val Pro Gly Glu Val Glu Met Val Lys
                20                  25                  30

Gly Gln Pro Phe Asp Val Gly Pro Arg Tyr Thr Gln Leu Gln Tyr Ile
            35                  40                  45

Gly Glu Gly Ala Tyr Gly Met Val Ser Ser Ala Tyr Asp His Val Arg
 50                  55                  60

Lys Thr Arg Val Ala Ile Lys Lys Ile Ser Pro Phe Glu His Gln Thr
65                  70                  75                  80

Tyr Cys Gln Arg Thr Leu Arg Glu Ile Gln Ile Leu Leu Arg Phe Arg
                85                  90                  95

His Glu Asn Val Ile Gly Ile Arg Asp Ile Leu Arg Ala Ser Thr Leu
            100                 105                 110

Glu Ala Met Arg Asp Val Tyr Ile Val Gln Asp Leu Met Glu Thr Asp
        115                 120                 125

Leu Tyr Lys Leu Leu Lys Ser Gln Gln Leu Ser Asn Asp His Ile Cys
130                 135                 140

Tyr Phe Leu Tyr Gln Ile Leu Arg Gly Leu Lys Tyr Ile His Ser Ala
145                 150                 155                 160

Asn Val Leu His Arg Asp Leu Lys Pro Ser Asn Leu Leu Ile Asn Thr
                165                 170                 175

Thr Cys Asp Leu Lys Ile Cys Asp Phe Gly Leu Ala Arg Ile Ala Asp
            180                 185                 190

Pro Glu His Asp His Thr Gly Phe Leu Thr Glu Tyr Val Ala Thr Arg
        195                 200                 205

Trp Tyr Arg Ala Pro Glu Ile Met Leu Asn Ser Lys Gly Tyr Thr Lys
210                 215                 220

Ser Ile Asp Ile Trp Ser Val Gly Cys Ile Leu Ala Glu Met Leu Ser
225                 230                 235                 240

Asn Arg Pro Ile Phe Pro Gly Lys His Tyr Leu Asp Gln Leu Asn His
                245                 250                 255

Ile Leu Gly Ile Leu Gly Ser Pro Ser Gln Glu Asp Leu Asn Cys Ile
            260                 265                 270

Ile Asn Met Lys Ala Arg Asn Tyr Leu Gln Ser Leu Pro Ser Lys Thr
        275                 280                 285

Lys Val Ala Trp Ala Lys Leu Phe Pro Lys Ser Asp Ser Lys Ala Leu
290                 295                 300

Asp Leu Leu Asp Arg Met Leu Thr Phe Asn Pro Asn Lys Arg Ile Thr
305                 310                 315                 320
```

-continued

Val Glu Glu Ala Leu Ala His Pro Tyr Leu Glu Gln Tyr Tyr Asp Pro
            325                 330                 335

Thr Asp Glu Pro Val Ala Glu Pro Phe Thr Phe Ala Met Glu Leu
            340                 345                 350

Asp Asp Leu Pro Lys Glu Arg Leu Lys Glu Leu Ile Phe Gln Glu Thr
            355                 360                 365

Ala Arg Phe Gln Pro Gly Val Leu Glu Ala Pro
    370                 375

<210> SEQ ID NO 24
<211> LENGTH: 480
<212> TYPE: PRT
<213> ORGANISM: Homo sapiens

<400> SEQUENCE: 24

Met Ser Asp Val Ala Ile Val Lys Glu Gly Trp Leu His Lys Arg Gly
  1               5                  10                  15

Glu Tyr Ile Lys Thr Trp Arg Pro Arg Tyr Phe Leu Leu Lys Asn Asp
             20                  25                  30

Gly Thr Phe Ile Gly Tyr Lys Glu Arg Pro Gln Asp Val Asp Gln Arg
         35                  40                  45

Glu Ala Pro Leu Asn Asn Phe Ser Val Ala Gln Cys Gln Leu Met Lys
     50                  55                  60

Thr Glu Arg Pro Arg Pro Asn Thr Phe Ile Ile Arg Cys Leu Gln Trp
 65                  70                  75                  80

Thr Thr Val Ile Glu Arg Thr Phe His Val Glu Thr Pro Glu Glu Arg
                 85                  90                  95

Glu Glu Trp Thr Thr Ala Ile Gln Thr Val Ala Asp Gly Leu Lys Lys
            100                 105                 110

Gln Glu Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300

Thr Met Lys Thr Phe Cys Gly Thr Pro Glu Tyr Leu Ala Pro Glu Val
305                 310                 315                 320

-continued

```
Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr Ala Gln Met Ile Thr
        435                 440                 445

Ile Thr Pro Pro Asp Gln Asp Asp Ser Met Glu Cys Val Asp Ser Glu
    450                 455                 460

Arg Arg Pro His Phe Pro Gln Phe Ser Tyr Ser Ala Ser Gly Thr Ala
465                 470                 475                 480

<210> SEQ ID NO 25
<211> LENGTH: 655
<212> TYPE: PRT
<213> ORGANISM: Homo sapiens

<400> SEQUENCE: 25

Met Ala Glu Ala Pro Gln Val Val Glu Ile Asp Pro Asp Phe Glu Pro
1               5                   10                  15

Leu Pro Arg Pro Arg Ser Cys Thr Trp Pro Leu Pro Arg Pro Glu Phe
            20                  25                  30

Ser Gln Ser Asn Ser Ala Thr Ser Ser Pro Ala Pro Ser Gly Ser Ala
        35                  40                  45

Ala Ala Asn Pro Asp Ala Ala Ala Gly Leu Pro Ser Ala Ser Ala Ala
    50                  55                  60

Ala Val Ser Ala Asp Phe Met Ser Asn Leu Ser Leu Leu Glu Glu Ser
65                  70                  75                  80

Glu Asp Phe Pro Gln Ala Pro Gly Ser Val Ala Ala Val Ala Ala Ala
                85                  90                  95

Ala Ala Ala Ala Ala Thr Gly Gly Leu Cys Gly Asp Phe Gln Gly Pro
            100                 105                 110

Glu Ala Gly Cys Leu His Pro Ala Pro Gln Pro Pro Pro Pro Gly Pro
        115                 120                 125

Leu Ser Gln His Pro Pro Val Pro Pro Ala Ala Ala Gly Pro Leu Ala
    130                 135                 140

Gly Gln Pro Arg Lys Ser Ser Ser Ser Arg Arg Asn Ala Trp Gly Asn
145                 150                 155                 160

Leu Ser Tyr Ala Asp Leu Ile Thr Lys Ala Ile Glu Ser Ser Ala Glu
                165                 170                 175

Lys Arg Leu Thr Leu Ser Gln Ile Tyr Glu Trp Met Val Lys Ser Val
            180                 185                 190

Pro Tyr Phe Lys Asp Lys Gly Asp Ser Asn Ser Ser Ala Gly Trp Lys
        195                 200                 205

Asn Ser Ile Arg His Asn Leu Ser Leu His Ser Lys Phe Ile
    210                 215                 220
```

```
Arg Val Gln Asn Glu Gly Thr Gly Lys Ser Ser Trp Trp Met Leu Asn
225                 230                 235                 240

Pro Glu Gly Gly Lys Ser Gly Lys Ser Pro Arg Arg Ala Ala Ser
            245                 250                 255

Met Asp Asn Asn Ser Lys Phe Ala Lys Ser Arg Ser Arg Ala Ala Lys
                260                 265                 270

Lys Lys Ala Ser Leu Gln Ser Gly Gln Glu Gly Ala Gly Asp Ser Pro
            275                 280                 285

Gly Ser Gln Phe Ser Lys Trp Pro Ala Ser Pro Gly Ser His Ser Asn
            290                 295                 300

Asp Asp Phe Asp Asn Trp Ser Thr Phe Arg Pro Arg Thr Ser Ser Asn
305                 310                 315                 320

Ala Ser Thr Ile Ser Gly Arg Leu Ser Pro Ile Met Thr Glu Gln Asp
                325                 330                 335

Asp Leu Gly Glu Gly Asp Val His Ser Met Val Tyr Pro Pro Ser Ala
            340                 345                 350

Ala Lys Met Ala Ser Thr Leu Pro Ser Leu Ser Glu Ile Ser Asn Pro
            355                 360                 365

Glu Asn Met Glu Asn Leu Leu Asp Asn Leu Asn Leu Leu Ser Ser Pro
370                 375                 380

Thr Ser Leu Thr Val Ser Thr Gln Ser Ser Pro Gly Thr Met Met Gln
385                 390                 395                 400

Gln Thr Pro Cys Tyr Ser Phe Ala Pro Pro Asn Thr Ser Leu Asn Ser
                405                 410                 415

Pro Ser Pro Asn Tyr Gln Lys Tyr Thr Tyr Gly Gln Ser Ser Met Ser
                420                 425                 430

Pro Leu Pro Gln Met Pro Ile Gln Thr Leu Gln Asp Asn Lys Ser Ser
            435                 440                 445

Tyr Gly Gly Met Ser Gln Tyr Asn Cys Ala Pro Gly Leu Leu Lys Glu
            450                 455                 460

Leu Leu Thr Ser Asp Ser Pro Pro His Asn Asp Ile Met Thr Pro Val
465                 470                 475                 480

Asp Pro Gly Val Ala Gln Pro Asn Ser Arg Val Leu Gly Gln Asn Val
                485                 490                 495

Met Met Gly Pro Asn Ser Val Met Ser Thr Tyr Gly Ser Gln Ala Ser
            500                 505                 510

His Asn Lys Met Met Asn Pro Ser Ser His Thr His Pro Gly His Ala
            515                 520                 525

Gln Gln Thr Ser Ala Val Asn Gly Arg Pro Leu Pro His Thr Val Ser
            530                 535                 540

Thr Met Pro His Thr Ser Gly Met Asn Arg Leu Thr Gln Val Lys Thr
545                 550                 555                 560

Pro Val Gln Val Pro Leu Pro His Pro Met Gln Met Ser Ala Leu Gly
                565                 570                 575

Gly Tyr Ser Ser Val Ser Ser Cys Asn Gly Tyr Gly Arg Met Gly Leu
            580                 585                 590

Leu His Gln Glu Lys Leu Pro Ser Asp Leu Asp Gly Met Phe Ile Glu
            595                 600                 605

Arg Leu Asp Cys Asp Met Glu Ser Ile Ile Arg Asn Asp Leu Met Asp
            610                 615                 620

Gly Asp Thr Leu Asp Phe Asn Phe Asp Asn Val Leu Pro Asn Gln Ser
625                 630                 635                 640

Phe Pro His Ser Val Lys Thr Thr Thr His Ser Trp Val Ser Gly
```

<210> SEQ ID NO 26
<211> LENGTH: 1038
<212> TYPE: PRT
<213> ORGANISM: Homo sapiens

<400> SEQUENCE: 26

```
Met Gln Pro Glu Glu Gly Thr Gly Trp Leu Leu Glu Leu Leu Ser Glu
 1               5                  10                  15
Val Gln Leu Gln Gln Tyr Phe Leu Arg Leu Arg Asp Asp Leu Asn Val
            20                  25                  30
Thr Arg Leu Ser His Phe Glu Tyr Val Lys Asn Glu Asp Leu Glu Lys
        35                  40                  45
Ile Gly Met Gly Arg Pro Gly Gln Arg Leu Trp Glu Ala Val Lys
    50                  55                  60
Arg Arg Lys Ala Leu Cys Lys Arg Lys Ser Trp Met Ser Lys Val Phe
 65                  70                  75                  80
Ser Gly Lys Arg Leu Glu Ala Glu Phe Pro Pro His Ser Gln Ser
                85                  90                  95
Thr Phe Arg Lys Thr Ser Pro Ala Pro Gly Gly Pro Ala Gly Glu Gly
            100                 105                 110
Pro Leu Gln Ser Leu Thr Cys Leu Ile Gly Glu Lys Asp Leu Arg Leu
        115                 120                 125
Leu Glu Lys Leu Gly Asp Gly Ser Phe Gly Val Val Arg Arg Gly Glu
    130                 135                 140
Trp Asp Ala Pro Ser Gly Lys Thr Val Ser Val Ala Val Lys Cys Leu
145                 150                 155                 160
Lys Pro Asp Val Leu Ser Gln Pro Glu Ala Met Asp Asp Phe Ile Arg
                165                 170                 175
Glu Val Asn Ala Met His Ser Leu Asp His Arg Asn Leu Ile Arg Leu
            180                 185                 190
Tyr Gly Val Val Leu Thr Pro Pro Met Lys Met Val Thr Glu Leu Ala
        195                 200                 205
Pro Leu Gly Ser Leu Leu Asp Arg Leu Arg Lys His Gln Gly His Phe
    210                 215                 220
Leu Leu Gly Thr Leu Ser Arg Tyr Ala Val Gln Val Ala Glu Gly Met
225                 230                 235                 240
Gly Tyr Leu Glu Ser Lys Arg Phe Ile His Arg Asp Leu Ala Ala Arg
                245                 250                 255
Asn Leu Leu Ala Thr Arg Asp Leu Val Lys Ile Gly Asp Phe Gly
            260                 265                 270
Leu Met Arg Ala Leu Pro Gln Asn Asp Asp His Tyr Val Met Gln Glu
        275                 280                 285
His Arg Lys Val Pro Phe Ala Trp Cys Ala Pro Glu Ser Leu Lys Thr
    290                 295                 300
Arg Thr Phe Ser His Ala Ser Asp Thr Trp Met Phe Gly Val Thr Leu
305                 310                 315                 320
Trp Glu Met Phe Thr Tyr Gly Gln Glu Pro Trp Ile Gly Leu Asn Gly
                325                 330                 335
Ser Gln Ile Leu His Lys Ile Asp Lys Glu Gly Glu Arg Leu Pro Arg
            340                 345                 350
Pro Glu Asp Cys Pro Gln Asp Ile Tyr Asn Val Met Val Gln Cys Trp
        355                 360                 365
Ala His Lys Pro Glu Asp Arg Pro Thr Phe Val Ala Leu Arg Asp Phe
```

-continued

```
                370                 375                 380
Leu Leu Glu Ala Gln Pro Thr Asp Met Arg Ala Leu Gln Asp Phe Glu
385                 390                 395                 400

Glu Pro Asp Lys Leu His Ile Gln Met Asn Asp Val Ile Thr Val Ile
                405                 410                 415

Glu Gly Arg Ala Glu Asn Tyr Trp Trp Arg Gly Gln Asn Thr Arg Thr
                420                 425                 430

Leu Cys Val Gly Pro Phe Pro Arg Asn Val Val Thr Ser Val Ala Gly
                435                 440                 445

Leu Ser Ala Gln Asp Ile Ser Gln Pro Leu Gln Asn Ser Phe Ile His
                450                 455                 460

Thr Gly His Gly Asp Ser Asp Pro Arg His Cys Trp Gly Phe Pro Asp
465                 470                 475                 480

Arg Ile Asp Glu Leu Tyr Leu Gly Asn Pro Met Asp Pro Pro Asp Leu
                485                 490                 495

Leu Ser Val Glu Leu Ser Thr Ser Arg Pro Pro Gln His Leu Gly Gly
                500                 505                 510

Val Lys Lys Pro Thr Tyr Asp Pro Val Ser Glu Asp Gln Asp Pro Leu
                515                 520                 525

Ser Ser Asp Phe Lys Arg Leu Gly Leu Arg Lys Pro Gly Leu Pro Arg
                530                 535                 540

Gly Leu Trp Leu Ala Lys Pro Ser Ala Arg Val Pro Gly Thr Lys Ala
545                 550                 555                 560

Ser Arg Gly Ser Gly Ala Glu Val Thr Leu Ile Asp Phe Gly Glu Glu
                565                 570                 575

Pro Val Val Pro Ala Leu Arg Pro Cys Ala Pro Ser Leu Ala Gln Leu
                580                 585                 590

Ala Met Asp Ala Cys Ser Leu Leu Asp Glu Thr Pro Pro Gln Ser Pro
                595                 600                 605

Thr Arg Ala Leu Pro Arg Pro Leu His Pro Thr Pro Val Val Asp Trp
                610                 615                 620

Asp Ala Arg Pro Leu Pro Pro Pro Ala Tyr Asp Asp Val Ala Gln
625                 630                 635                 640

Asp Glu Asp Asp Phe Glu Ile Cys Ser Ile Asn Ser Thr Leu Val Gly
                645                 650                 655

Ala Gly Val Pro Ala Gly Pro Ser Gln Gly Thr Asn Tyr Ala Phe
                660                 665                 670

Val Pro Glu Gln Ala Arg Pro Pro Pro Leu Glu Asp Asn Leu Phe
                675                 680                 685

Leu Pro Pro Gln Gly Gly Gly Lys Pro Pro Ser Ser Ala Gln Thr Ala
                690                 695                 700

Glu Ile Phe Gln Ala Leu Gln Gln Glu Cys Met Arg Gln Leu Gln Ala
705                 710                 715                 720

Pro Ala Gly Ser Pro Ala Pro Ser Pro Ser Gly Gly Asp Asp Lys
                725                 730                 735

Pro Gln Val Pro Pro Arg Val Pro Ile Pro Pro Arg Pro Thr Arg Pro
                740                 745                 750

His Val Gln Leu Ser Pro Ala Pro Pro Gly Glu Glu Thr Ser Gln
                755                 760                 765

Trp Pro Gly Pro Ala Ser Pro Pro Arg Val Pro Pro Arg Glu Pro Leu
                770                 775                 780

Ser Pro Gln Gly Ser Arg Thr Pro Ser Pro Leu Val Pro Pro Gly Ser
785                 790                 795                 800
```

```
Ser Pro Leu Pro Pro Arg Leu Ser Ser Pro Gly Lys Thr Met Pro
            805                 810                 815

Thr Thr Gln Ser Phe Ala Ser Asp Pro Lys Tyr Ala Thr Pro Gln Val
            820                 825                 830

Ile Gln Ala Pro Gly Pro Arg Ala Gly Pro Cys Ile Leu Pro Ile Val
            835                 840                 845

Arg Asp Gly Lys Lys Val Ser Ser Thr His Tyr Tyr Leu Leu Pro Glu
850                 855                 860

Arg Pro Ser Tyr Leu Glu Arg Tyr Gln Arg Phe Leu Arg Glu Ala Gln
865                 870                 875                 880

Ser Pro Glu Glu Pro Thr Pro Leu Pro Val Pro Leu Leu Leu Pro Pro
            885                 890                 895

Pro Ser Thr Pro Ala Pro Ala Ala Pro Thr Ala Thr Val Arg Pro Met
            900                 905                 910

Pro Gln Ala Ala Leu Asp Pro Lys Ala Asn Phe Ser Thr Asn Asn Ser
            915                 920                 925

Asn Pro Gly Ala Arg Pro Pro Pro Arg Ala Thr Ala Arg Leu Pro
            930                 935                 940

Gln Arg Gly Cys Pro Gly Asp Gly Pro Glu Ala Gly Arg Pro Ala Asp
945                 950                 955                 960

Lys Ile Gln Met Ala Met Val His Gly Val Thr Thr Glu Glu Cys Gln
                965                 970                 975

Ala Ala Leu Gln Cys His Gly Trp Ser Val Gln Arg Ala Ala Gln Tyr
            980                 985                 990

Leu Lys Val Glu Gln Leu Phe Gly Leu Gly Leu Arg Pro Arg Gly Glu
            995                 1000                1005

Cys His Lys Val Leu Glu Met Phe Asp Trp Asn Leu Glu Gln Ala Gly
            1010                1015                1020

Cys His Leu Leu Gly Ser Trp Gly Pro Ala His His Lys Arg
1025                1030                1035

<210> SEQ ID NO 27
<211> LENGTH: 403
<212> TYPE: PRT
<213> ORGANISM: Homo sapiens

<400> SEQUENCE: 27

Met Asp Arg Ser Lys Glu Asn Cys Ile Ser Gly Pro Val Lys Ala Thr
1               5                   10                  15

Ala Pro Val Gly Gly Pro Lys Arg Val Leu Val Thr Gln Gln Phe Pro
                20                  25                  30

Cys Gln Asn Pro Leu Pro Val Asn Ser Gly Gln Ala Gln Arg Val Leu
            35                  40                  45

Cys Pro Ser Asn Ser Ser Gln Arg Val Pro Leu Gln Ala Gln Lys Leu
50                  55                  60

Val Ser Ser His Lys Pro Val Gln Asn Gln Lys Gln Lys Gln Leu Gln
65                  70                  75                  80

Ala Thr Ser Val Pro His Pro Val Ser Arg Pro Leu Asn Asn Thr Gln
                85                  90                  95

Lys Ser Lys Gln Pro Leu Pro Ser Ala Pro Glu Asn Asn Pro Glu Glu
            100                 105                 110

Glu Leu Ala Ser Lys Gln Lys Asn Glu Glu Ser Lys Lys Arg Gln Trp
        115                 120                 125

Ala Leu Glu Asp Phe Glu Ile Gly Arg Pro Leu Gly Lys Gly Lys Phe
    130                 135                 140
```

```
Gly Asn Val Tyr Leu Ala Arg Glu Lys Gln Ser Lys Phe Ile Leu Ala
145                 150                 155                 160

Leu Lys Val Leu Phe Lys Ala Gln Leu Glu Lys Ala Gly Val Glu His
                165                 170                 175

Gln Leu Arg Arg Glu Val Glu Ile Gln Ser His Leu Arg His Pro Asn
            180                 185                 190

Ile Leu Arg Leu Tyr Gly Tyr Phe His Asp Ala Thr Arg Val Tyr Leu
        195                 200                 205

Ile Leu Glu Tyr Ala Pro Leu Gly Thr Val Tyr Arg Glu Leu Gln Lys
    210                 215                 220

Leu Ser Lys Phe Asp Glu Gln Arg Thr Ala Thr Tyr Ile Thr Glu Leu
225                 230                 235                 240

Ala Asn Ala Leu Ser Tyr Cys His Ser Lys Arg Val Ile His Arg Asp
                245                 250                 255

Ile Lys Pro Glu Asn Leu Leu Leu Gly Ser Ala Gly Glu Leu Lys Ile
            260                 265                 270

Ala Asp Phe Gly Trp Ser Val His Ala Pro Ser Ser Arg Arg Thr Thr
        275                 280                 285

Leu Cys Gly Thr Leu Asp Tyr Leu Pro Pro Glu Met Ile Glu Gly Arg
290                 295                 300

Met His Asp Glu Lys Val Asp Leu Trp Ser Leu Gly Val Leu Cys Tyr
305                 310                 315                 320

Glu Phe Leu Val Gly Lys Pro Pro Phe Glu Ala Asn Thr Tyr Gln Glu
                325                 330                 335

Thr Tyr Lys Arg Ile Ser Arg Val Glu Phe Thr Phe Pro Asp Phe Val
            340                 345                 350

Thr Glu Gly Ala Arg Asp Leu Ile Ser Arg Leu Leu Lys His Asn Pro
        355                 360                 365

Ser Gln Arg Pro Met Leu Arg Glu Val Leu Glu His Pro Trp Ile Thr
370                 375                 380

Ala Asn Ser Ser Lys Pro Ser Asn Cys Gln Asn Lys Glu Ser Ala Ser
385                 390                 395                 400

Lys Gln Ser

<210> SEQ ID NO 28
<211> LENGTH: 536
<212> TYPE: PRT
<213> ORGANISM: Homo sapiens

<400> SEQUENCE: 28

Met Gly Ser Asn Lys Ser Lys Pro Lys Asp Ala Ser Gln Arg Arg Arg
1               5                   10                  15

Ser Leu Glu Pro Ala Glu Asn Val His Gly Ala Gly Gly Gly Ala Phe
                20                  25                  30

Pro Ala Ser Gln Thr Pro Ser Lys Pro Ala Ser Ala Asp Gly His Arg
            35                  40                  45

Gly Pro Ser Ala Ala Phe Ala Pro Ala Ala Glu Pro Lys Leu Phe
        50                  55                  60

Gly Gly Phe Asn Ser Ser Asp Thr Val Thr Ser Pro Gln Arg Ala Gly
65                  70                  75                  80

Pro Leu Ala Gly Gly Val Thr Thr Phe Val Ala Leu Tyr Asp Tyr Glu
                85                  90                  95

Ser Arg Thr Glu Thr Asp Leu Ser Phe Lys Lys Gly Glu Arg Leu Gln
            100                 105                 110

Ile Val Asn Asn Thr Glu Gly Asp Trp Trp Leu Ala His Ser Leu Ser
```

```
            115                 120                 125
Thr Gly Gln Thr Gly Tyr Ile Pro Ser Asn Tyr Val Ala Pro Ser Asp
130                 135                 140

Ser Ile Gln Ala Glu Glu Trp Tyr Phe Gly Lys Ile Thr Arg Arg Glu
145                 150                 155                 160

Ser Glu Arg Leu Leu Leu Asn Ala Glu Asn Pro Arg Gly Thr Phe Leu
                165                 170                 175

Val Arg Glu Ser Glu Thr Thr Lys Gly Ala Tyr Cys Leu Ser Val Ser
            180                 185                 190

Asp Phe Asp Asn Ala Lys Gly Leu Asn Val Lys His Tyr Lys Ile Arg
        195                 200                 205

Lys Leu Asp Ser Gly Gly Phe Tyr Ile Thr Ser Arg Thr Gln Phe Asn
    210                 215                 220

Ser Leu Gln Gln Leu Val Ala Tyr Tyr Ser Lys His Ala Asp Gly Leu
225                 230                 235                 240

Cys His Arg Leu Thr Thr Val Cys Pro Thr Ser Lys Pro Gln Thr Gln
                245                 250                 255

Gly Leu Ala Lys Asp Ala Trp Glu Ile Pro Arg Glu Ser Leu Arg Leu
            260                 265                 270

Glu Val Lys Leu Gly Gln Gly Cys Phe Gly Glu Val Trp Met Gly Thr
        275                 280                 285

Trp Asn Gly Thr Thr Arg Val Ala Ile Lys Thr Leu Lys Pro Gly Thr
    290                 295                 300

Met Ser Pro Glu Ala Phe Leu Gln Glu Ala Gln Val Met Lys Lys Leu
305                 310                 315                 320

Arg His Glu Lys Leu Val Gln Leu Tyr Ala Val Val Ser Glu Glu Pro
                325                 330                 335

Ile Tyr Ile Val Thr Glu Tyr Met Ser Lys Gly Ser Leu Leu Asp Phe
            340                 345                 350

Leu Lys Gly Glu Thr Gly Lys Tyr Leu Arg Leu Pro Gln Leu Val Asp
        355                 360                 365

Met Ala Ala Gln Ile Ala Ser Gly Met Ala Tyr Val Glu Arg Met Asn
    370                 375                 380

Tyr Val His Arg Asp Leu Arg Ala Ala Asn Ile Leu Val Gly Glu Asn
385                 390                 395                 400

Leu Val Cys Lys Val Ala Asp Phe Gly Leu Ala Arg Leu Ile Glu Asp
                405                 410                 415

Asn Glu Tyr Thr Ala Arg Gln Gly Ala Lys Phe Pro Ile Lys Trp Thr
            420                 425                 430

Ala Pro Glu Ala Ala Leu Tyr Gly Arg Phe Thr Ile Lys Ser Asp Val
        435                 440                 445

Trp Ser Phe Gly Ile Leu Leu Thr Glu Leu Thr Thr Lys Gly Arg Val
    450                 455                 460

Pro Tyr Pro Gly Met Val Asn Arg Glu Val Leu Asp Gln Val Glu Arg
465                 470                 475                 480

Gly Tyr Arg Met Pro Cys Pro Pro Glu Cys Pro Glu Ser Leu His Asp
                485                 490                 495

Leu Met Cys Gln Cys Trp Arg Lys Glu Pro Glu Glu Arg Pro Thr Phe
            500                 505                 510

Glu Tyr Leu Gln Ala Phe Leu Glu Asp Tyr Phe Thr Ser Thr Glu Pro
        515                 520                 525

Gln Tyr Gln Pro Gly Glu Asn Leu
    530                 535
```

```
<210> SEQ ID NO 29
<211> LENGTH: 168
<212> TYPE: PRT
<213> ORGANISM: Homo sapiens

<400> SEQUENCE: 29

Met Phe Gln Ile Pro Glu Phe Glu Pro Ser Glu Gln Glu Asp Ser Ser
 1               5                  10                  15

Ser Ala Glu Arg Gly Leu Gly Pro Ser Pro Ala Gly Asp Gly Pro Ser
            20                  25                  30

Gly Ser Gly Lys His His Arg Gln Ala Pro Gly Leu Leu Trp Asp Ala
        35                  40                  45

Ser His Gln Gln Glu Gln Pro Thr Ser Ser His His Gly Gly Ala
    50                  55                  60

Gly Ala Val Glu Ile Arg Ser Arg His Ser Ser Tyr Pro Ala Gly Thr
65                  70                  75                  80

Glu Asp Asp Glu Gly Met Gly Glu Glu Pro Ser Pro Phe Arg Gly Arg
                85                  90                  95

Ser Arg Ser Ala Pro Pro Asn Leu Trp Ala Ala Gln Arg Tyr Gly Arg
            100                 105                 110

Glu Leu Arg Arg Met Ser Asp Glu Phe Val Asp Ser Phe Lys Lys Gly
        115                 120                 125

Leu Pro Arg Pro Lys Ser Ala Gly Thr Ala Thr Gln Met Arg Gln Ser
    130                 135                 140

Ser Ser Trp Thr Arg Val Phe Gln Ser Trp Trp Asp Arg Asn Leu Gly
145                 150                 155                 160

Arg Gly Ser Ser Ala Pro Ser Gln
                165

<210> SEQ ID NO 30
<211> LENGTH: 136
<212> TYPE: PRT
<213> ORGANISM: Homo sapiens

<400> SEQUENCE: 30

Met Ala Arg Thr Lys Gln Thr Ala Arg Lys Ser Thr Gly Gly Lys Ala
 1               5                  10                  15

Pro Arg Lys Gln Leu Ala Thr Lys Ala Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Cys Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135

<210> SEQ ID NO 31
<211> LENGTH: 919
<212> TYPE: PRT
```

<213> ORGANISM: Homo sapiens

<400> SEQUENCE: 31

| | | | | | | | | | | | | | | |
|---|---|---|---|---|---|---|---|---|---|---|---|---|---|---|
| Met | Glu | Val | Gln | Leu | Gly | Leu | Gly | Arg | Val | Tyr | Pro | Arg | Pro | Ser |
| 1 | | | | 5 | | | | | 10 | | | | | 15 |
| Lys | Thr | Tyr | Arg | Gly | Ala | Phe | Gln | Asn | Leu | Phe | Gln | Ser | Val | Arg | Glu |
| | | | 20 | | | | | 25 | | | | | 30 | | |
| Val | Ile | Gln | Asn | Pro | Gly | Pro | Arg | His | Pro | Glu | Ala | Ala | Ser | Ala | Ala |
| | | | 35 | | | | | 40 | | | | | 45 | | |
| Pro | Pro | Gly | Ala | Ser | Leu | Leu | Leu | Leu | Gln | Gln | Gln | Gln | Gln | Gln |
| | 50 | | | | | 55 | | | | | 60 | | | | |
| Gln | Gln | Gln | Gln | Gln | Gln | Gln | Gln | Gln | Gln | Gln | Gln | Gln | Glu | Thr |
| 65 | | | | | 70 | | | | | 75 | | | | | 80 |
| Ser | Pro | Arg | Gln | Gln | Gln | Gln | Gln | Gly | Glu | Asp | Gly | Ser | Pro | Gln |
| | | | | 85 | | | | | 90 | | | | | 95 |
| Ala | His | Arg | Arg | Gly | Pro | Thr | Gly | Tyr | Leu | Val | Leu | Asp | Glu | Glu | Gln |
| | | | 100 | | | | | 105 | | | | | 110 | | |
| Gln | Pro | Ser | Gln | Pro | Gln | Ser | Ala | Leu | Glu | Cys | His | Pro | Glu | Arg | Gly |
| | | | 115 | | | | | 120 | | | | | 125 | | |
| Cys | Val | Pro | Glu | Pro | Gly | Ala | Ala | Val | Ala | Ala | Ser | Lys | Gly | Leu | Pro |
| | 130 | | | | | 135 | | | | | 140 | | | | |
| Gln | Gln | Leu | Pro | Ala | Pro | Pro | Asp | Glu | Asp | Ser | Ala | Ala | Pro | Ser |
| 145 | | | | | 150 | | | | | 155 | | | | | 160 |
| Thr | Leu | Ser | Leu | Leu | Gly | Pro | Thr | Phe | Pro | Gly | Leu | Ser | Ser | Cys | Ser |
| | | | | 165 | | | | | 170 | | | | | 175 | |
| Ala | Asp | Leu | Lys | Asp | Ile | Leu | Ser | Glu | Ala | Ser | Thr | Met | Gln | Leu | Leu |
| | | | 180 | | | | | 185 | | | | | 190 | | |
| Gln | Gln | Gln | Gln | Gln | Glu | Ala | Val | Ser | Glu | Ser | Ser | Ser | Gly | Arg |
| | | | 195 | | | | | 200 | | | | | 205 | | |
| Ala | Arg | Glu | Ala | Ser | Gly | Ala | Pro | Thr | Ser | Ser | Lys | Asp | Asn | Tyr | Leu |
| | 210 | | | | | 215 | | | | | 220 | | | | |
| Gly | Gly | Thr | Ser | Thr | Ile | Ser | Asp | Asn | Ala | Lys | Glu | Leu | Cys | Lys | Ala |
| 225 | | | | | 230 | | | | | 235 | | | | | 240 |
| Val | Ser | Val | Ser | Met | Gly | Leu | Gly | Val | Glu | Ala | Leu | Glu | His | Leu | Ser |
| | | | | 245 | | | | | 250 | | | | | 255 | |
| Pro | Gly | Glu | Gln | Leu | Arg | Gly | Asp | Cys | Met | Tyr | Ala | Pro | Leu | Leu | Gly |
| | | | 260 | | | | | 265 | | | | | 270 | | |
| Val | Pro | Pro | Ala | Val | Arg | Pro | Thr | Pro | Cys | Ala | Pro | Leu | Ala | Glu | Cys |
| | | 275 | | | | | 280 | | | | | 285 | | | |
| Lys | Gly | Ser | Leu | Leu | Asp | Asp | Ser | Ala | Gly | Lys | Ser | Thr | Glu | Asp | Thr |
| | 290 | | | | | 295 | | | | | 300 | | | | |
| Ala | Glu | Tyr | Ser | Pro | Phe | Lys | Gly | Gly | Tyr | Thr | Lys | Gly | Leu | Glu | Gly |
| 305 | | | | | 310 | | | | | 315 | | | | | 320 |
| Glu | Ser | Leu | Gly | Cys | Ser | Gly | Ser | Ala | Ala | Gly | Ser | Ser | Gly | Thr |
| | | | | 325 | | | | | 330 | | | | | 335 | |
| Leu | Glu | Leu | Pro | Ser | Thr | Leu | Ser | Leu | Tyr | Lys | Ser | Gly | Ala | Leu | Asp |
| | | | 340 | | | | | 345 | | | | | 350 | | |
| Glu | Ala | Ala | Ala | Tyr | Gln | Ser | Arg | Asp | Tyr | Tyr | Asn | Phe | Pro | Leu | Ala |
| | | | 355 | | | | | 360 | | | | | 365 | | |
| Leu | Ala | Gly | Pro | Pro | Pro | Pro | Pro | Pro | His | Pro | His | Ala | Arg |
| | 370 | | | | | 375 | | | | | 380 | | | | |
| Ile | Lys | Leu | Glu | Asn | Pro | Leu | Asp | Tyr | Gly | Ser | Ala | Trp | Ala | Ala |
| 385 | | | | | 390 | | | | | 395 | | | | | 400 |
| Ala | Ala | Gln | Cys | Arg | Tyr | Gly | Asp | Leu | Ala | Ser | Leu | His | Gly | Ala | Gly |

-continued

```
                405                 410                 415
Ala Ala Gly Pro Gly Ser Gly Ser Pro Ser Ala Ala Ser Ser Ser
                420                 425                 430

Trp His Thr Leu Phe Thr Ala Glu Glu Gly Gln Leu Tyr Gly Pro Cys
        435                 440                 445

Gly Gly Gly Gly Gly Gly Gly Gly Gly Gly Gly Gly Gly
        450                 455                 460

Gly Gly Gly Gly Gly Gly Gly Glu Ala Gly Val Ala Pro Tyr
465                 470                 475                 480

Gly Tyr Thr Arg Pro Pro Gln Gly Leu Ala Gly Gln Glu Ser Asp Phe
                485                 490                 495

Thr Ala Pro Asp Val Trp Tyr Pro Gly Gly Met Val Ser Arg Val Pro
            500                 505                 510

Tyr Pro Ser Pro Thr Cys Val Lys Ser Glu Met Gly Pro Trp Met Asp
            515                 520                 525

Ser Tyr Ser Gly Pro Tyr Gly Asp Met Arg Leu Glu Thr Ala Arg Asp
            530                 535                 540

His Val Leu Pro Ile Asp Tyr Tyr Phe Pro Pro Gln Lys Thr Cys Leu
545                 550                 555                 560

Ile Cys Gly Asp Glu Ala Ser Gly Cys His Tyr Gly Ala Leu Thr Cys
                565                 570                 575

Gly Ser Cys Lys Val Phe Phe Lys Arg Ala Ala Glu Gly Lys Gln Lys
            580                 585                 590

Tyr Leu Cys Ala Ser Arg Asn Asp Cys Thr Ile Asp Lys Phe Arg Arg
            595                 600                 605

Lys Asn Cys Pro Ser Cys Arg Leu Arg Lys Cys Tyr Glu Ala Gly Met
            610                 615                 620

Thr Leu Gly Ala Arg Lys Leu Lys Lys Leu Gly Asn Leu Lys Leu Gln
625                 630                 635                 640

Glu Glu Gly Glu Ala Ser Ser Thr Thr Ser Pro Thr Glu Glu Thr Thr
                645                 650                 655

Gln Lys Leu Thr Val Ser His Ile Glu Gly Tyr Glu Cys Gln Pro Ile
            660                 665                 670

Phe Leu Asn Val Leu Glu Ala Ile Glu Pro Gly Val Val Cys Ala Gly
            675                 680                 685

His Asp Asn Asn Gln Pro Asp Ser Phe Ala Ala Leu Leu Ser Ser Leu
        690                 695                 700

Asn Glu Leu Gly Glu Arg Gln Leu Val His Val Val Lys Trp Ala Lys
705                 710                 715                 720

Ala Leu Pro Gly Phe Arg Asn Leu His Val Asp Asp Gln Met Ala Val
                725                 730                 735

Ile Gln Tyr Ser Trp Met Gly Leu Met Val Phe Ala Met Gly Trp Arg
            740                 745                 750

Ser Phe Thr Asn Val Asn Ser Arg Met Leu Tyr Phe Ala Pro Asp Leu
        755                 760                 765

Val Phe Asn Glu Tyr Arg Met His Lys Ser Arg Met Tyr Ser Gln Cys
770                 775                 780

Val Arg Met Arg His Leu Ser Gln Glu Phe Gly Trp Leu Gln Ile Thr
785                 790                 795                 800

Pro Gln Glu Phe Leu Cys Met Lys Ala Leu Leu Leu Phe Ser Ile Ile
                805                 810                 815

Pro Val Asp Gly Leu Lys Asn Gln Lys Phe Phe Asp Glu Leu Arg Met
            820                 825                 830
```

```
Asn Tyr Ile Lys Glu Leu Asp Arg Ile Ile Ala Cys Lys Arg Lys Asn
            835                 840                 845
Pro Thr Ser Cys Ser Arg Arg Phe Tyr Gln Leu Thr Lys Leu Leu Asp
        850                 855                 860
Ser Val Gln Pro Ile Ala Arg Glu Leu His Gln Phe Thr Phe Asp Leu
865                 870                 875                 880
Leu Ile Lys Ser His Met Val Ser Val Asp Phe Pro Glu Met Met Ala
                885                 890                 895
Glu Ile Ile Ser Val Gln Val Pro Lys Ile Leu Ser Gly Lys Val Lys
            900                 905                 910
Pro Ile Tyr Phe His Thr Gln
            915

<210> SEQ ID NO 32
<211> LENGTH: 794
<212> TYPE: PRT
<213> ORGANISM: Homo sapiens

<400> SEQUENCE: 32

Met Ala Gly Trp Ile Gln Ala Gln Gln Leu Gln Gly Asp Ala Leu Arg
1               5                   10                  15
Gln Met Gln Val Leu Tyr Gly Gln His Phe Pro Ile Glu Val Arg His
            20                  25                  30
Tyr Leu Ala Gln Trp Ile Glu Ser Gln Pro Trp Asp Ala Ile Asp Leu
        35                  40                  45
Asp Asn Pro Gln Asp Arg Ala Gln Ala Thr Gln Leu Leu Glu Gly Leu
    50                  55                  60
Val Gln Glu Leu Gln Lys Lys Ala Glu His Gln Val Gly Glu Asp Gly
65                  70                  75                  80
Phe Leu Leu Lys Ile Lys Leu Gly His Tyr Ala Thr Gln Leu Gln Lys
                85                  90                  95
Thr Tyr Asp Arg Cys Pro Leu Glu Leu Val Arg Cys Ile Arg His Ile
            100                 105                 110
Leu Tyr Asn Glu Gln Arg Leu Val Arg Glu Ala Asn Asn Cys Ser Ser
        115                 120                 125
Pro Ala Gly Ile Leu Val Asp Ala Met Ser Gln Lys His Leu Gln Ile
    130                 135                 140
Asn Gln Thr Phe Glu Glu Leu Arg Leu Val Thr Gln Asp Thr Glu Asn
145                 150                 155                 160
Glu Leu Lys Lys Leu Gln Gln Thr Gln Glu Tyr Phe Ile Ile Gln Tyr
                165                 170                 175
Gln Glu Ser Leu Arg Ile Gln Ala Gln Phe Ala Gln Leu Ala Gln Leu
            180                 185                 190
Ser Pro Gln Glu Arg Leu Ser Arg Glu Thr Ala Leu Gln Gln Lys Gln
        195                 200                 205
Val Ser Leu Glu Ala Trp Leu Gln Arg Glu Ala Gln Thr Leu Gln Gln
    210                 215                 220
Tyr Arg Val Glu Leu Ala Glu Lys His Gln Lys Thr Leu Gln Leu Leu
225                 230                 235                 240
Arg Lys Gln Gln Thr Ile Ile Leu Asp Asp Glu Leu Ile Gln Trp Lys
                245                 250                 255
Arg Arg Gln Gln Leu Ala Gly Asn Gly Gly Pro Pro Glu Gly Ser Leu
            260                 265                 270
Asp Val Leu Gln Ser Trp Cys Glu Lys Leu Ala Glu Ile Ile Trp Gln
        275                 280                 285
```

```
Asn Arg Gln Gln Ile Arg Arg Ala Glu His Leu Cys Gln Gln Leu Pro
    290                 295                 300

Ile Pro Gly Pro Val Glu Met Leu Ala Glu Val Asn Ala Thr Ile
305                 310                 315                 320

Thr Asp Ile Ile Ser Ala Leu Val Thr Ser Thr Phe Ile Ile Glu Lys
                    325                 330                 335

Gln Pro Pro Gln Val Leu Lys Thr Gln Thr Lys Phe Ala Ala Thr Val
                340                 345                 350

Arg Leu Leu Val Gly Gly Lys Leu Asn Val His Met Asn Pro Pro Gln
            355                 360                 365

Val Lys Ala Thr Ile Ile Ser Glu Gln Gln Ala Lys Ser Leu Leu Lys
    370                 375                 380

Asn Glu Asn Thr Arg Asn Glu Cys Ser Gly Glu Ile Leu Asn Cys
385                 390                 395                 400

Cys Val Met Glu Tyr His Gln Ala Thr Gly Thr Leu Ser Ala His Phe
                    405                 410                 415

Arg Asn Met Ser Leu Lys Arg Ile Lys Arg Ala Asp Arg Arg Gly Ala
                420                 425                 430

Glu Ser Val Thr Glu Glu Lys Phe Thr Val Leu Phe Glu Ser Gln Phe
            435                 440                 445

Ser Val Gly Ser Asn Glu Leu Val Phe Gln Val Lys Thr Leu Ser Leu
    450                 455                 460

Pro Val Val Ile Val His Gly Ser Gln Asp His Asn Ala Thr Ala
465                 470                 475                 480

Thr Val Leu Trp Asp Asn Ala Phe Ala Glu Pro Gly Arg Val Pro Phe
                    485                 490                 495

Ala Val Pro Asp Lys Val Leu Trp Pro Gln Leu Cys Glu Ala Leu Asn
                500                 505                 510

Met Lys Phe Lys Ala Glu Val Gln Ser Asn Arg Gly Leu Thr Lys Glu
            515                 520                 525

Asn Leu Val Phe Leu Ala Gln Lys Leu Phe Asn Asn Ser Ser Ser His
    530                 535                 540

Leu Glu Asp Tyr Ser Gly Leu Ser Val Ser Trp Ser Gln Phe Asn Arg
545                 550                 555                 560

Glu Asn Leu Pro Gly Trp Asn Tyr Thr Phe Trp Gln Trp Phe Asp Gly
                    565                 570                 575

Val Met Glu Val Leu Lys Lys His His Lys Pro His Trp Asn Asp Gly
                580                 585                 590

Ala Ile Leu Gly Phe Val Asn Lys Gln Gln Ala His Asp Leu Leu Ile
            595                 600                 605

Asn Lys Pro Asp Gly Thr Phe Leu Leu Arg Phe Ser Asp Ser Glu Ile
    610                 615                 620

Gly Gly Ile Thr Ile Ala Trp Lys Phe Asp Ser Pro Glu Arg Asn Leu
625                 630                 635                 640

Trp Asn Leu Lys Pro Phe Thr Thr Arg Asp Phe Ser Ile Arg Ser Leu
                    645                 650                 655

Ala Asp Arg Leu Gly Asp Leu Ser Tyr Leu Ile Tyr Val Phe Pro Asp
                660                 665                 670

Arg Pro Lys Asp Glu Val Phe Ser Lys Tyr Tyr Thr Pro Val Leu Ala
            675                 680                 685

Lys Ala Val Asp Gly Tyr Val Lys Pro Gln Ile Lys Gln Val Val Pro
    690                 695                 700

Glu Phe Val Asn Ala Ser Ala Asp Ala Gly Gly Ser Ser Ala Thr Tyr
705                 710                 715                 720
```

Met Asp Gln Ala Pro Ser Pro Ala Val Cys Pro Gln Ala Pro Tyr Asn
            725                 730                 735

Met Tyr Pro Gln Asn Pro Asp His Val Leu Asp Gln Asp Gly Glu Phe
            740                 745                 750

Asp Leu Asp Glu Thr Met Asp Val Ala Arg His Val Glu Glu Leu Leu
            755                 760                 765

Arg Arg Pro Met Asp Ser Leu Asp Ser Arg Leu Ser Pro Pro Ala Gly
            770                 775                 780

Leu Phe Thr Ser Ala Arg Gly Ser Leu Ser
785                 790

<210> SEQ ID NO 33
<211> LENGTH: 847
<212> TYPE: PRT
<213> ORGANISM: Homo sapiens

<400> SEQUENCE: 33

Met Ser Leu Trp Gly Leu Val Ser Lys Met Pro Pro Glu Lys Val Gln
1               5                   10                  15

Arg Leu Tyr Val Asp Phe Pro Gln His Leu Arg His Leu Leu Gly Asp
            20                  25                  30

Trp Leu Glu Ser Gln Pro Trp Glu Phe Leu Val Gly Ser Asp Ala Phe
        35                  40                  45

Cys Cys Asn Leu Ala Ser Ala Leu Leu Ser Asp Thr Val Gln His Leu
    50                  55                  60

Gln Ala Ser Val Gly Glu Gln Gly Glu Gly Ser Thr Ile Leu Gln His
65                  70                  75                  80

Ile Ser Thr Leu Glu Ser Ile Tyr Gln Arg Asp Pro Leu Lys Leu Val
                85                  90                  95

Ala Thr Phe Arg Gln Ile Leu Gln Gly Glu Lys Lys Ala Val Met Glu
            100                 105                 110

Gln Phe Arg His Leu Pro Met Pro Phe His Trp Lys Gln Glu Glu Leu
        115                 120                 125

Lys Phe Lys Thr Gly Leu Arg Arg Leu Gln His Arg Val Gly Glu Ile
    130                 135                 140

His Leu Leu Arg Glu Ala Leu Gln Lys Gly Ala Glu Ala Gly Gln Val
145                 150                 155                 160

Ser Leu His Ser Leu Ile Glu Thr Pro Ala Asn Gly Thr Gly Pro Ser
                165                 170                 175

Glu Ala Leu Ala Met Leu Leu Gln Glu Thr Thr Gly Glu Leu Glu Ala
            180                 185                 190

Ala Lys Ala Leu Val Leu Lys Arg Ile Gln Ile Trp Lys Arg Gln Gln
        195                 200                 205

Gln Leu Ala Gly Asn Gly Ala Pro Phe Glu Glu Ser Leu Ala Pro Leu
    210                 215                 220

Gln Glu Arg Cys Glu Ser Leu Val Asp Ile Tyr Ser Gln Leu Gln Gln
225                 230                 235                 240

Glu Val Gly Ala Ala Gly Gly Glu Leu Glu Pro Lys Thr Arg Ala Ser
                245                 250                 255

Leu Thr Gly Arg Leu Asp Glu Val Leu Arg Thr Leu Val Thr Ser Cys
            260                 265                 270

Phe Leu Val Glu Lys Gln Pro Pro Gln Val Leu Lys Thr Gln Thr Lys
        275                 280                 285

Phe Gln Ala Gly Val Arg Phe Leu Leu Gly Leu Arg Phe Leu Gly Ala
    290                 295                 300

-continued

```
Pro Ala Lys Pro Pro Leu Val Arg Ala Asp Met Val Thr Glu Lys Gln
305                 310                 315                 320

Ala Arg Glu Leu Ser Val Pro Gln Gly Pro Gly Ala Gly Ala Glu Ser
            325                 330                 335

Thr Gly Glu Ile Ile Asn Asn Thr Val Pro Leu Glu Asn Ser Ile Pro
            340                 345                 350

Gly Asn Cys Cys Ser Ala Leu Phe Lys Asn Leu Leu Leu Lys Lys Ile
            355                 360                 365

Lys Arg Cys Glu Arg Lys Gly Thr Glu Ser Val Thr Glu Glu Lys Cys
370                 375                 380

Ala Val Leu Phe Ser Ala Ser Phe Thr Leu Gly Pro Gly Lys Leu Pro
385                 390                 395                 400

Ile Gln Leu Gln Ala Leu Ser Leu Pro Leu Val Val Ile Val His Gly
                405                 410                 415

Asn Gln Asp Asn Asn Ala Lys Ala Thr Ile Leu Trp Asp Asn Ala Phe
            420                 425                 430

Ser Glu Met Asp Arg Val Pro Phe Val Val Ala Glu Arg Val Pro Trp
            435                 440                 445

Glu Lys Met Cys Glu Thr Leu Asn Leu Lys Phe Met Ala Glu Val Gly
            450                 455                 460

Thr Asn Arg Gly Leu Leu Pro Glu His Phe Leu Phe Leu Ala Gln Lys
465                 470                 475                 480

Ile Phe Asn Asp Asn Ser Leu Ser Met Glu Ala Phe Gln His Arg Ser
                485                 490                 495

Val Ser Trp Ser Gln Phe Asn Lys Glu Ile Leu Leu Gly Arg Gly Phe
            500                 505                 510

Thr Phe Trp Gln Trp Phe Asp Gly Val Leu Asp Leu Thr Lys Arg Cys
            515                 520                 525

Leu Arg Ser Tyr Trp Ser Asp Arg Leu Ile Ile Gly Phe Ile Ser Lys
530                 535                 540

Gln Tyr Val Thr Ser Leu Leu Asn Glu Pro Asp Gly Thr Phe Leu
545                 550                 555                 560

Leu Arg Phe Ser Asp Ser Glu Ile Gly Gly Ile Thr Ile Ala His Val
                565                 570                 575

Ile Arg Gly Gln Asp Gly Ser Pro Gln Ile Glu Asn Ile Gln Pro Phe
            580                 585                 590

Ser Ala Lys Asp Leu Ser Ile Arg Ser Leu Gly Asp Arg Ile Arg Asp
            595                 600                 605

Leu Ala Gln Leu Lys Asn Leu Tyr Pro Lys Lys Pro Lys Asp Glu Ala
610                 615                 620

Phe Arg Ser His Tyr Lys Pro Glu Gln Met Gly Lys Asp Gly Arg Gly
625                 630                 635                 640

Tyr Val Pro Ala Thr Ile Lys Met Thr Val Glu Arg Asp Gln Pro Leu
                645                 650                 655

Pro Thr Pro Glu Leu Gln Met Pro Thr Met Val Pro Ser Tyr Asp Leu
            660                 665                 670

Gly Met Ala Pro Asp Ser Ser Met Ser Met Gln Leu Gly Pro Asp Met
            675                 680                 685

Val Pro Gln Val Tyr Pro Pro His Ser His Ser Ile Pro Pro Tyr Gln
            690                 695                 700

Gly Leu Ser Pro Glu Glu Ser Val Asn Val Leu Ser Ala Phe Gln Glu
705                 710                 715                 720

Pro His Leu Gln Met Pro Pro Ser Leu Gly Gln Met Ser Leu Pro Phe
```

```
                    725                 730                 735
Asp Gln Pro His Pro Gln Gly Leu Leu Pro Cys Gln Pro Gln Glu His
            740                 745                 750

Ala Val Ser Ser Pro Asp Pro Leu Leu Cys Ser Asp Val Thr Met Val
            755                 760                 765

Glu Asp Ser Cys Leu Ser Gln Pro Val Thr Ala Phe Pro Gln Gly Thr
            770                 775                 780

Trp Ile Gly Glu Asp Ile Phe Pro Pro Leu Pro Pro Thr Glu Gln
785                 790                 795                 800

Asp Leu Thr Lys Leu Leu Leu Glu Gly Gln Gly Glu Ser Gly Gly Gly
                805                 810                 815

Ser Leu Gly Ala Gln Pro Leu Leu Gln Pro Ser His Tyr Gly Gln Ser
                820                 825                 830

Gly Ile Ser Met Ser His Met Asp Leu Arg Ala Asn Pro Ser Trp
                835                 840                 845

<210> SEQ ID NO 34
<211> LENGTH: 433
<212> TYPE: PRT
<213> ORGANISM: Homo sapiens

<400> SEQUENCE: 34

Met Ala Leu Arg Val Thr Arg Asn Ser Lys Ile Asn Ala Glu Asn Lys
1               5                   10                  15

Ala Lys Ile Asn Met Ala Gly Ala Lys Arg Val Pro Thr Ala Pro Ala
            20                  25                  30

Ala Thr Ser Lys Pro Gly Leu Arg Pro Arg Thr Ala Leu Gly Asp Ile
        35                  40                  45

Gly Asn Lys Val Ser Glu Gln Leu Gln Ala Lys Met Pro Met Lys Lys
    50                  55                  60

Glu Ala Lys Pro Ser Ala Thr Gly Lys Val Ile Asp Lys Lys Leu Pro
65                  70                  75                  80

Lys Pro Leu Glu Lys Val Pro Met Leu Val Pro Val Pro Val Ser Glu
                85                  90                  95

Pro Val Pro Glu Pro Glu Pro Glu Pro Glu Pro Val Lys Glu
            100                 105                 110

Glu Lys Leu Ser Pro Glu Pro Ile Leu Val Asp Thr Ala Ser Pro Ser
        115                 120                 125

Pro Met Glu Thr Ser Gly Cys Ala Pro Ala Glu Glu Asp Leu Cys Gln
    130                 135                 140

Ala Phe Ser Asp Val Ile Leu Ala Val Asn Asp Val Asp Ala Glu Asp
145                 150                 155                 160

Gly Ala Asp Pro Asn Leu Cys Ser Glu Tyr Val Lys Asp Ile Tyr Ala
                165                 170                 175

Tyr Leu Arg Gln Leu Glu Glu Glu Gln Ala Val Arg Pro Lys Tyr Leu
            180                 185                 190

Leu Gly Arg Glu Val Thr Gly Asn Met Arg Ala Ile Leu Ile Asp Trp
        195                 200                 205

Leu Val Gln Val Gln Met Lys Phe Arg Leu Leu Gln Glu Thr Met Tyr
    210                 215                 220

Met Thr Val Ser Ile Ile Asp Arg Phe Met Gln Asn Asn Cys Val Pro
225                 230                 235                 240

Lys Lys Met Leu Gln Leu Val Gly Val Thr Ala Met Phe Ile Ala Ser
                245                 250                 255

Lys Tyr Glu Glu Met Tyr Pro Pro Glu Ile Gly Asp Phe Ala Phe Val
```

-continued

```
                        260                 265                 270
Thr Asp Asn Thr Tyr Thr Lys His Gln Ile Arg Gln Met Glu Met Lys
            275                 280                 285

Ile Leu Arg Ala Leu Asn Phe Gly Leu Gly Arg Pro Leu Pro Leu His
        290                 295                 300

Phe Leu Arg Arg Ala Ser Lys Ile Gly Glu Val Asp Val Glu Gln His
305                 310                 315                     320

Thr Leu Ala Lys Tyr Leu Met Glu Leu Thr Met Leu Asp Tyr Asp Met
                325                 330                 335

Val His Phe Pro Pro Ser Gln Ile Ala Ala Gly Ala Phe Cys Leu Ala
            340                 345                 350

Leu Lys Ile Leu Asp Asn Gly Glu Trp Thr Pro Thr Leu Gln His Tyr
        355                 360                 365

Leu Ser Tyr Thr Glu Glu Ser Leu Leu Pro Val Met Gln His Leu Ala
    370                 375                 380

Lys Asn Val Val Met Val Asn Gln Gly Leu Thr Lys His Met Thr Val
385                 390                 395                 400

Lys Asn Lys Tyr Ala Thr Ser Lys His Ala Lys Ile Ser Thr Leu Pro
                405                 410                 415

Gln Leu Asn Ser Ala Leu Val Gln Asp Leu Ala Lys Ala Val Ala Lys
            420                 425                 430

Val
```

CELLULAR ASSAY EMPLOYING DETECTABLE PROTEIN

1. CROSS REFERENCE

The instant application claims the benefit of U.S. provisional application No. 61/172,680, filed Apr. 24, 2009, the disclosure of which is incorporated herein by reference in its entirety, and is a national stage application of PCT application PCT/US2010/032160, the disclosure of which is incorporated herein by reference in its entirety.

2. FIELD

The subject matter provided herein relates to the field of detection of protein modification, including methods for screening and identifying compounds that modulate the activity of proteins involved in various cellular processes.

3. SUMMARY

Provided herein are assays useful, for example, for determining the activity of a protein involved in a cellular process. In some embodiments, the activity of the protein is assessed using a nucleic acid tag, and in particular, by detecting the presence of a nucleic acid tag. Such assays can be used, for example, to study the effects of test compounds as modulators, e.g., inhibitors, agonists and antagonists, of protein activity.

Thus, in one aspect, provided herein is a method of detecting a protein modified by a cellular process of interest comprising the steps of: (a) contacting a detectable protein comprising a target protein and a nucleic-acid interacting motif with (i) an antibody that binds the target protein that has been modified by the cellular process of interest, and (ii) a nucleic acid oligomer comprising a nucleic acid sequence that binds the nucleic-acid interacting motif; and (b) detecting the presence of the nucleic acid oligomer that is bound to the detectable protein which is also bound by the antibody; wherein the presence of the bound nucleic acid oligomer of step (b) indicates the presence of a protein modified by the cellular process of interest. In some embodiments, the detectable protein is contacted with the antibody before the detectable protein is contacted with the nucleic acid oligomer in step (a). In some embodiments, the detectable protein is contacted with the antibody after the detectable protein is contacted with the nucleic acid oligomer in step (a). In some embodiments, the detectable protein is concurrently contacted with the antibody and the nucleic acid oligomer in step (a).

In some embodiments, the cellular process is selected from acylation, acetylation, deacetylation, formylation, alkylation, methylation, phosphorylation, dephosphorylation, sulfation, oxidation, reduction, hydroxylation, deamidation, carboxylation, disulfide formation, prenylation, glycation, glycosylation, ubiquitination, sumoylation, proteolysis, racemization and isomerization. In a particular embodiment, the cellular process is phosphorylation.

In some embodiments, the target protein is a kinase substrate. In some embodiments, the modified target protein is phosphorylated at one or more residues, and the antibody is an anti-phospho antibody. In some embodiments, the modified target protein is phosphorylated at one or more tyrosine residues, and the antibody is an anti-phosphotyrosine antibody. In some embodiments, the modified target protein is phosphorylated at one or more serine residues, and the antibody is an anti-phosphoserine antibody. In some embodiments, the modified target protein is phosphorylated at one or more threonine residues, and the antibody is an anti-phosphothreonine antibody.

In some embodiments, the target protein is a G-coupled protein receptor, an ion channel protein, a nuclear receptor protein, a transcription factor, a kinase, a cytokine, a growth factor, a hormone, an enzyme, an antibody or a small chain variable fragment (scFv).

In some embodiments, the nucleic acid-interacting motif is a DNA-binding domain. In some embodiments, the DNA-binding domain is a NF-κB DNA binding domain, cro repressor DNA binding domain, lac repressor DNA binding domain, GAL4 DNA binding domain, GCN4 DNA binding domain, Lex-A DNA binding domain, Opaque-2 DNA binding domain or TGA1a DNA binding domain. In particular embodiments, the nucleic acid-interacting motif comprises the amino acid sequence depicted in SEQ ID NO:5 or SEQ ID NO:6.

In some embodiments, the oligomer is between about 50 and 500 nucleotides in length.

In another aspect, provided herein is a method of identifying a test compound which modulates a cellular process, wherein the cellular process modifies a target protein, said method comprising the steps of: (a) contacting a cell or cell lysate comprising a detectable protein with test compound, wherein the detectable protein comprises the target protein and a nucleic-acid interacting motif; (b) contacting the detectable protein with: (i) an antibody that specifically binds to the target protein that has been modified as a result of the cellular process; and (ii) a nucleic acid oligomer comprising a nucleic acid sequence that binds the nucleic-acid interacting motif; and (c) detecting an amount of nucleic acid oligomer bound to the detectable protein that is also bound by the antibody; wherein an increase or decrease in the amount of bound nucleic acid oligomer of step (c) detected in the presence of said test compound relative to the amount of bound nucleic acid oligomer detected in the absence of said test compound indicates that the test compound modulates the cellular process.

In some embodiments, an increase in the amount of bound nucleic acid oligomer of step (c) detected in the presence of said test compound relative to the amount of bound nucleic acid oligomer detected in the absence of said test compound indicates that the test compound agonizes the cellular process. In some embodiments, a decrease in the amount of bound nucleic acid oligomer of step (c) detected in the presence of said test compound relative to the amount of bound nucleic acid oligomer detected in the absence of said test compound indicates that the test compound inhibits the cellular process.

In some embodiments, step (a) comprises contacting a cell comprising the detectable protein with test compound. In some embodiments, the cell transiently expresses the detectable protein. In some embodiments, the cell stably expresses the detectable protein.

In some embodiments, the cellular process is selected from acylation, acetylation, deacetylation, formylation, alkylation, methylation, phosphorylation, dephosphorylation, sulfation, oxidation, reduction, hydroxylation, deamidation, carboxylation, disulfide formation, prenylation, glycation, glycosylation, ubiquitination, sumoylation, proteolysis, racemization and isomerization. In a particular embodiment, the cellular process is phosphorylation.

In some embodiments, the target protein is a kinase substrate. In some embodiments, the modified target protein is phosphorylated at one or more tyrosine residues, and the antibody is an anti-phosphotyrosine antibody. In some embodiments, the modified target protein is phosphorylated at one or more serine residues, and the antibody is an anti-phosphoserine antibody. In some embodiments, the modified target protein is phosphorylated at one or more threonine residues, and the antibody is an anti-phosphothreonine antibody.

In some embodiments, the target protein is a G-coupled protein receptor, an ion channel protein, a nuclear receptor protein, a transcription factor, a kinase, a cytokine, a growth factor, a hormone, an enzyme, an antibody or a small chain variable fragment (scFv).

In some embodiments, the nucleic acid-interacting motif is a DNA-binding domain. In some embodiments, the DNA-binding domain is a NF-κB DNA binding domain, cro repressor DNA binding domain, lac repressor DNA binding domain, GAL4 DNA binding domain, GCN4 DNA binding domain, Lex-A DNA binding domain, Opaque-2 DNA binding domain or TGA1a DNA binding domain. In particular embodiments, the nucleic acid-interacting motif comprises the amino acid sequence depicted in SEQ ID NO:5 or SEQ ID NO:6.

In some embodiments, the oligomer is between about 50 and 500 nucleotides in length.

In some embodiments, the kinase substrate is Mek1, wherein the antibody specifically binds to phosphorylated Mek1, and step (a) further comprises preparing a positive control sample whereby the cell or cell lysate comprising the detectable protein is contacted with a Braf inhibitor instead of test compound. Within these embodiments, contact with a Braf inhibitor preferably results in a decrease in the amount of bound nucleic acid oligomer detected in step (c), relative to the amount of bound nucleic acid oligomer detected in the absence of inhibitor, thereby indicating that the Braf inhibitor inhibits Braf kinase activity, e.g., inhibits the phosphorylation of MEK1. In some embodiments, the Braf inhibitor is selected from BAY-43-9006, PLX-4720, Chir-265.

In some embodiments, the kinase substrate is Akt1 and the antibody binds to phosphorylated Akt. In some embodiments, the antibody binds to Akt1 phosphorylated at Ser473 or Thr308. In some embodiments, the antibody binds to Akt1 phosphorylated at Thr308. In some embodiments, the antibody binds to Akt1 phosphorylated at Ser473.

In some embodiments, the kinase substrate is FRAP1 or PDPK1, wherein the antibody specifically binds to phosphorylated FRAP1 or phosphorylated PDPK1, respectively, and step (a) further comprises preparing a positive control sample whereby the cell or cell lysate comprising the detectable protein is contacted with a PIK3CA inhibitor instead of test compound. Within these embodiments, contact with a PIK3CA inhibitor preferably results in a decrease in the amount of bound nucleic acid oligomer detected in step (c), relative to the amount of bound nucleic acid oligomer detected in the absence of inhibitor, thereby indicating that the PIK3CA inhibitor inhibits PIK3CA kinase activity, e.g., inhibits the phosphorylation of FRAP1 or PDPK1, respectively. In some embodiments, the PIK3CA inhibitor is selected from PI103, ZSTK-474, wortmannin and PIK-93.

In some embodiments, the kinase substrate is AKT1, wherein the antibody specifically binds to phosphorylated AKT1, and step (a) further comprises preparing a positive control sample whereby the cell or cell lysate comprising the detectable protein is contacted with a PDPK1, FRAP1 or mTOR inhibitor instead of test compound. Within these embodiments, contact with a PDPK1, FRAP1 or mTOR inhibitor preferably results in a decrease in the amount of bound nucleic acid oligomer detected in step (c), relative to the amount of bound nucleic acid oligomer detected in the absence of inhibitor, thereby indicating that the PDPK1, FRAP1 or mTOR inhibitor inhibits PDPK1, FRAP1 or mTOR kinase activity, e.g., inhibits the phosphorylation of AKT1. In some embodiments, the PDPK1 inhibitor is BX-795.

In some embodiments, the kinase substrate is FOXO1 and the antibody specifically binds to phosphorylated FOXO1. In some embodiments, the antibody binds to FOXO1 phosphorylated at Thr24.

In some embodiments, step (a) further comprises preparing a positive control sample whereby the cell or cell lysate comprising a detectable protein is contacted with an AKT1 inhibitor instead of test compound. In some embodiments, the Akt1 inhibitor is GSK-690693.

In some embodiments, the methods provided herein comprise contacting the cell or cell lysate comprising a detectable protein with at least two concentrations of test compound and calculating the $IC_{50}$ of the test compound.

In some embodiments, the nucleic acid oligomer comprises (a) a first nucleic acid sequence that is a PCR amplification sequence, and (b) a second nucleic acid sequence that binds the nucleic acid-interacting motif, wherein the first nucleic acid sequence is heterologous to the second nucleic acid sequence.

In some embodiments, the methods provided herein comprise qPCR amplifying the nucleic acid oligomer that is bound to the detectable protein. In some embodiments, the nucleic acid oligomer is radiolabeled, fluorescently labeled or biotinylated.

In some embodiments of the methods provided herein, the antibody is immobilized on a solid support. In some embodiments, the antibody is immobilized on a multiwell plate.

In yet another aspect, provided herein is a kit comprising: a cell comprising a detectable protein, wherein the detectable protein comprises a target protein that can be modified by a cellular process, a nucleic-acid interacting motif; and a nucleic acid oligomer comprising a nucleic acid sequence that binds the nucleic-acid interacting motif In some embodiments, the kit further comprises an antibody that binds the target protein that has been modified by the cellular process of interest. In some embodiments, the cellular process is phosphorylation, and the modified target protein is a phosphorylated target protein.

4. BRIEF DESCRIPTION OF THE FIGURES

FIG. 1 provides a schematic diagram depicting a cellular assay which utilizes a detectable protein comprising a target protein and a nucleic-acid interacting motif, an antibody which binds to the target protein that has been modified by a cellular process, and a nucleic acid oligomer comprising a nucleic acid sequence that binds the nucleic-acid interacting motif.

Figure 2:
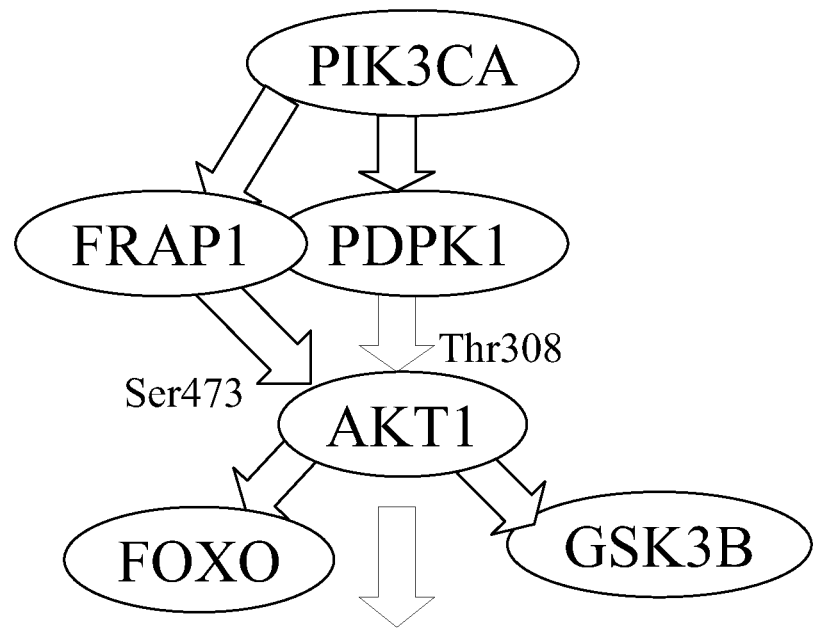

FIG. 2 provides a diagram of the PIK3CA signaling pathway.

FIG. 3 to FIG. 7 provide dose response curves for various compounds, where the x-axis represents compound concentration in nM and the y-axis represents the signal generated by qPCR which is in probe equivalent units (PEU).

Figure 3:
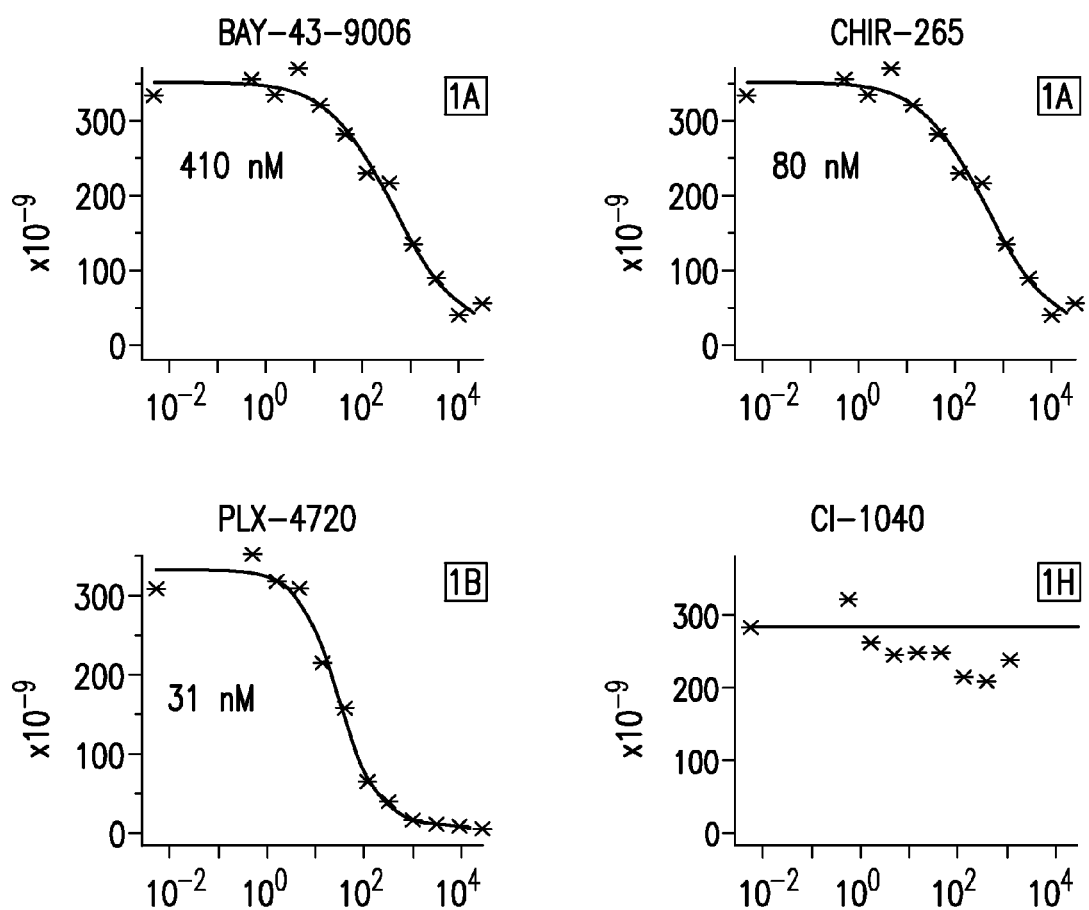

FIG. 3 provides the dose response curves for BAY-43-9006, PLX-4720, Chir-265 and CI-1040 obtained from the phospho-Mek1 binding assay.

Figure 4:
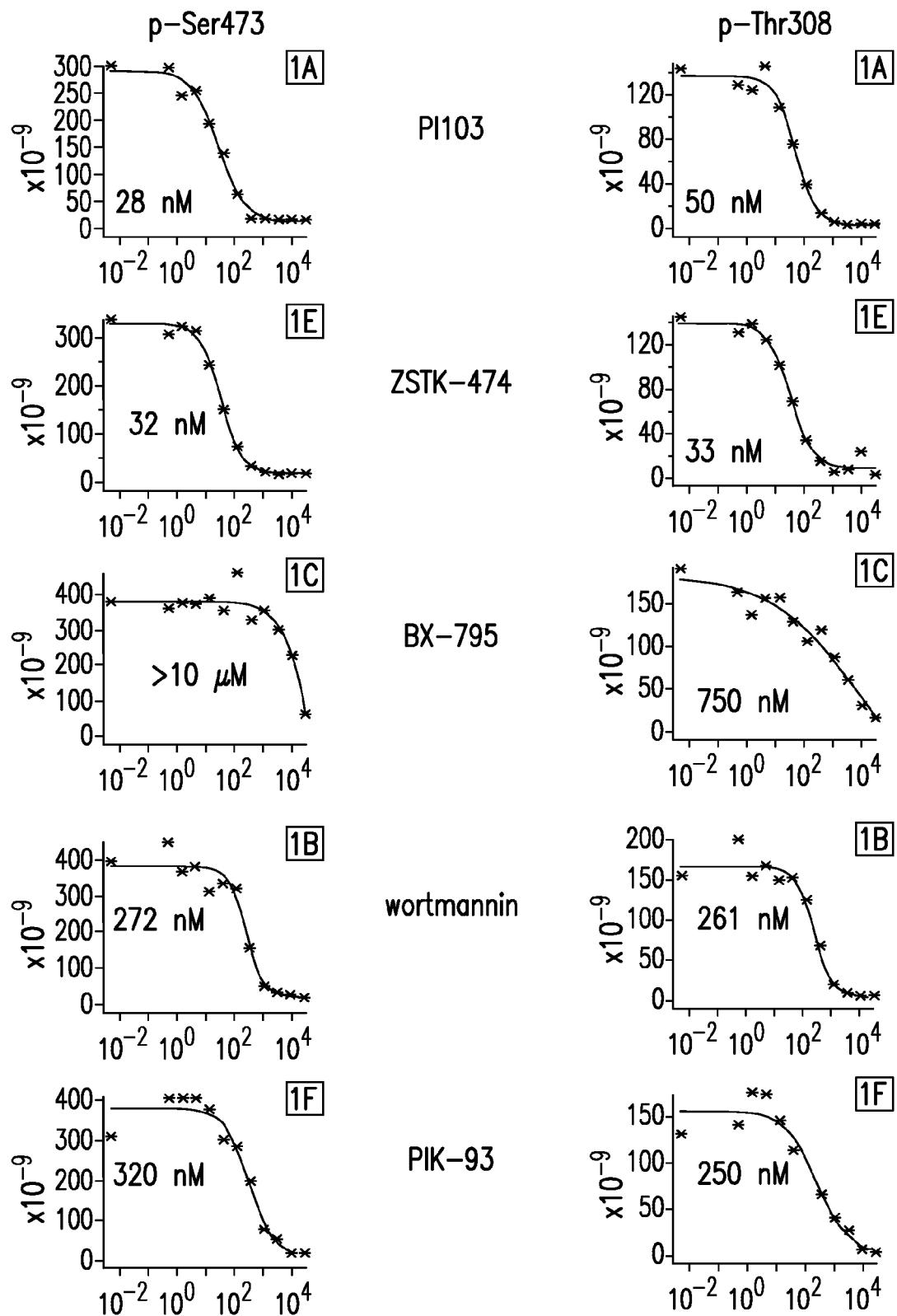

FIG. 4 provides the dose response curves for PI103, ZSTK-474, BX-795, wortmannin and PIK93 obtained from the phospho-Akt (Ser473) binding assay and the phosphor-Akt (Thr308) binding assay.

Figure 5:
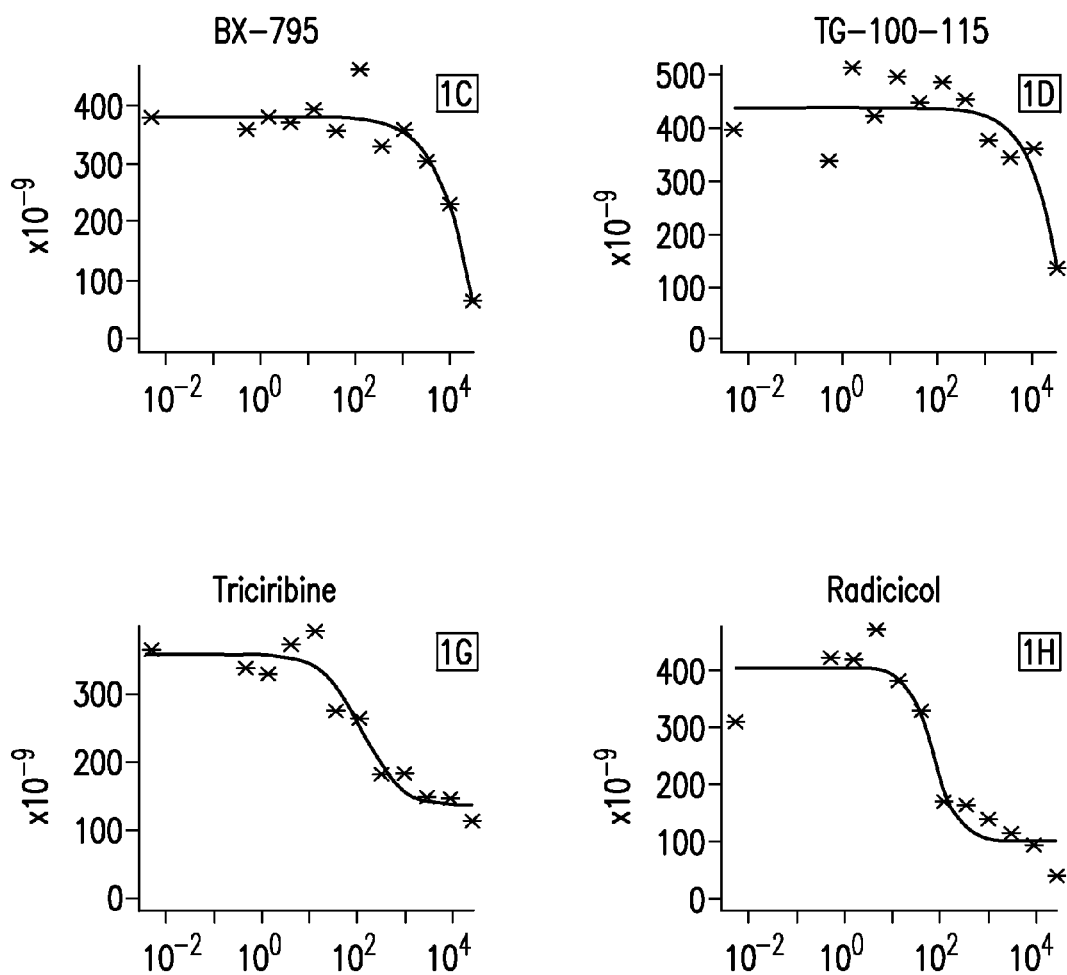

FIG. 5 provides the dose response curves for BX-795, TG-100-115, radicicol and triciribine in the phospho-Akt1 (Ser473) assay.

Figure 6:
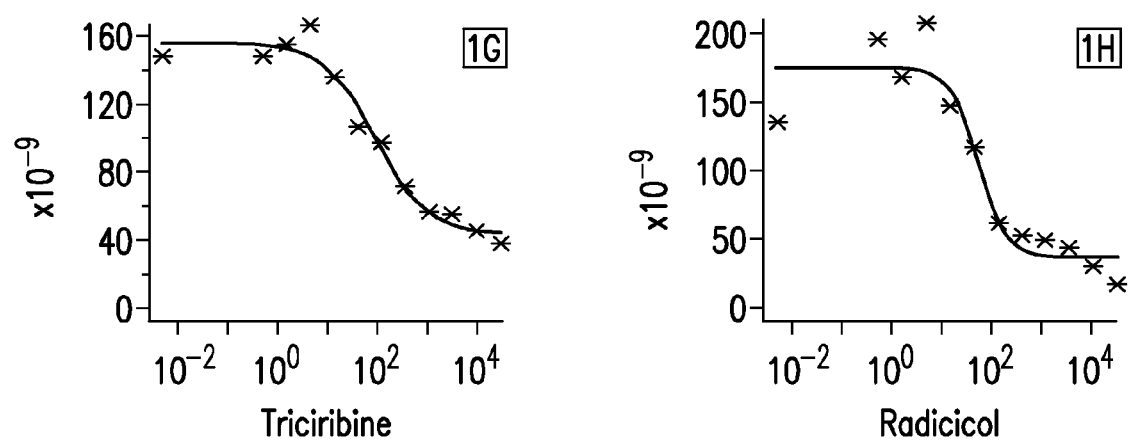

FIG. 6 provides the dose response curves for radicicol and triciribine in the phospho-Akt1 (Thr308) assay.

Figure 7:
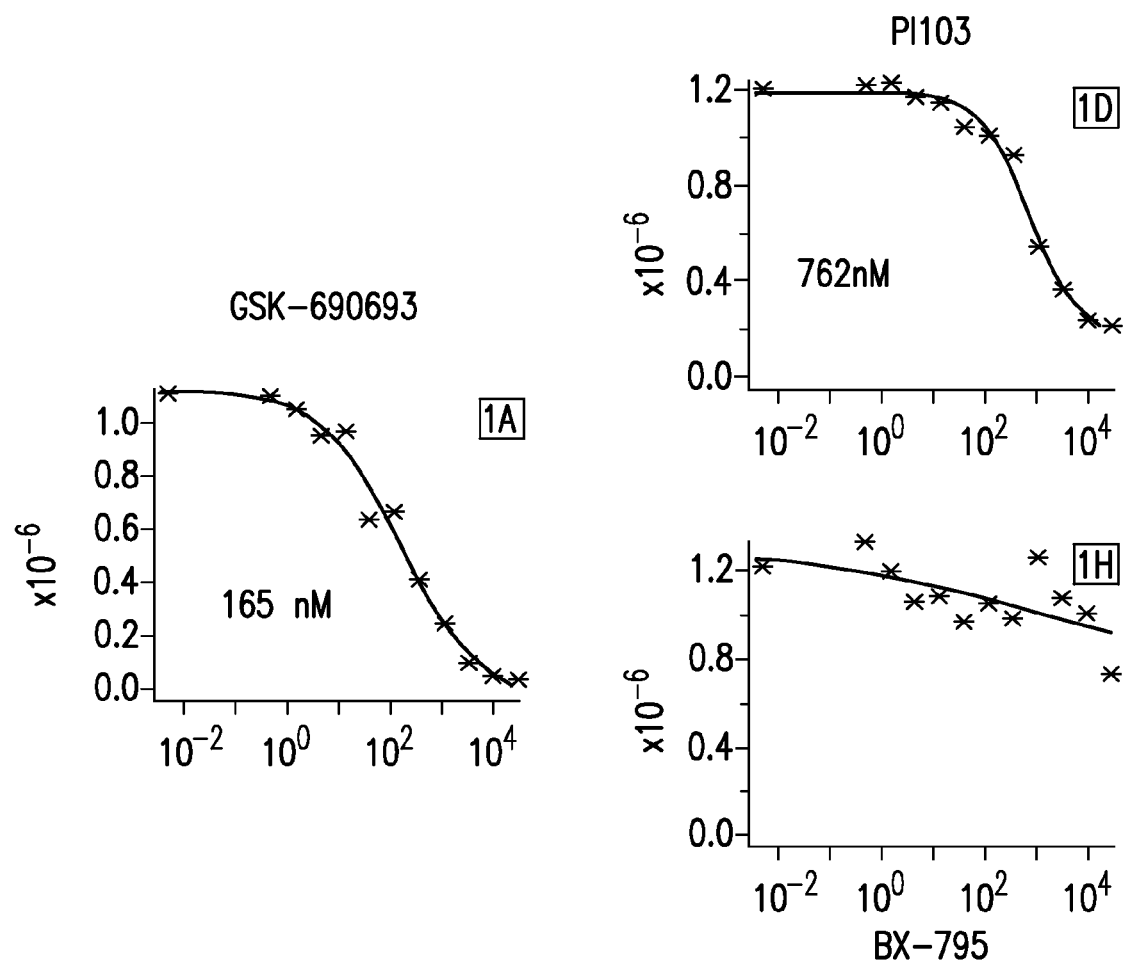

FIG. 7 provides the dose response curves for GSK-690693, PI103 and BX-795, in the AKT1-phospho-FOXO (T24) assay.

5. DETAILED DESCRIPTION OF THE EMBODIMENTS

5.1 Terminology

As used herein, the term "target protein" refers to any protein of interest that can be modified by as a result of a cellular process such as those described herein. In some embodiments, the target protein is modified by a protein having enzymatic or catalytic activity.

As used herein, the term "cellular process" and "cellular process of interest" is used interchangeably and refers to any event that occurs in a cell that results in the modification of a cellular protein. In some embodiments, the cellular process occurs during the course of processes which living cells undergo, for example, during uptake, transport, receptor binding, metabolism, fusion, biochemical response, cell detachment, cell migration, cell growth, necrosis and apoptosis. In other embodiments, the cellular process occurs during oncogenesis, transformation and/or metastasis. In some embodiments, a cellular process results in the modification of a protein, e.g., a target protein by a protein having a catalytic or enzymatic activity. In other embodiments, a cellular process results in enzymatic or non-enzymatic protein modification. In certain embodiments, the enzymatic or non-enzymatic protein modification is a covalent modification. In other embodiments, a cellular process results in enzymatic non-covalent protein modification including but not limited to proteolysis, racemization or isomerization. In other embodiments, a cellular process results in non-covalent modification such as protein homo- or hetero-dimerization or other binding events involving ligands, growth factors, hormones, cytokines, allosteric modulators, co-factors, co-enzymes and second messengers. Exemplary cellular processes include, but are not limited to, acylation, acetylation, deacetylation, formylation, alkylation, methylation, phosphorylation, dephosphorylation, sulfation, oxidation, reduction, hydroxylation, deamidation, carboxylation, disulfide formation, prenylation, glycation, glycosylation, ubiquitination, sumoylation, proteolysis, racemization and isomerization. Thus, as used herein, a protein that is modified by a cellular process is a protein which undergoes a modification that includes, but is not limited to, acylation, acetylation, deacetylation, formylation, alkylation, methylation, phosphorylation, dephosphorylation, sulfation, oxidation, reduction, hydroxylation, deamidation, carboxylation, disulfide formation, prenylation, glycation, glycosylation, ubiquitination, sumoylation, proteolysis, racemization and isomerization, as a result of the cellular process.

As used herein, the term "antibody" and "immunoglobulin" or "Ig" may be used interchangeably. "Antibodies" as used herein can be of any type (e.g., IgG, IgE, IgM, IgD, IgA and IgY), any class (e.g., IgG1, IgG2, IgG3, IgG4, IgA1 and IgA2), or any subclass (e.g., IgG2a and IgG2b) of immunoglobulin molecule, or any antigen-recognition (or antigen-binding) fragments thereof. The antibodies may be monoclonal or polyclonal and may be of any species of origin, including, but not limited to, mouse, rat, rabbit, horse, or human, or may be chimeric antibodies. See, e.g., Walker et al., Molec. Immunol. 1989; 26: 403-411; Morrision et al., Proc. Nat'l. Acad. Sci. 1984; 81: 6851; Neuberger et al., Nature 1984; 312: 604. The antibodies may be recombinant monoclonal antibodies produced according to the methods disclosed in U.S. Pat. No. 4,474,893 (Reading) or U.S. Pat. No. 4,816,567 (Cabilly et al.). The antibodies may also be chemically constructed by specific antibodies made according to the method disclosed in U.S. Pat. No. 4,676,980 (Segel et al.). Antibodies of the invention include, but are not limited to, synthetic antibodies, monoclonal antibodies, recombinantly produced antibodies, multispecific antibodies (including bi-specific antibodies), human antibodies, humanized antibodies, chimeric antibodies, intrabodies, single-chain Fvs (scFv) (e.g., including monospecific, bispecific, etc.), camelized antibodies, Fab fragments, F(ab')$_2$ fragments, disulfide-linked Fvs (sdFv), anti-idiotypic (anti-Id) antibodies, and epitope-binding fragments of any of the above. In particular, antibodies of the present invention include immunoglobulin molecules and immunologically active portions of immunoglobulin molecules, i.e., antigen binding domains or molecules that contain an antigen-binding site that immunospecifically binds to, e.g., a modified protein of interest. In certain embodiments, the antibody is an IgG antibody, such as a monoclonal IgG antibody.

As used herein, the term "anti-phospho antibody" refer to antibodies and antibody fragments that specifically bind to the phosphorylated form of a protein antigen or epitope, including a kinase antigen or epitope (e.g., an epitope comprising a phosphotyrosine, phosphothreonine or phosphoserine), but do not specifically bind to the non-phosphorylated form of the protein antigen or epitope. An antibody or a fragment that specifically binds to an antigen may be cross-reactive with related antigens. In one embodiment, an anti-phospho antibody is an antibody or antibody fragment that specifically binds to a kinase antigen and does not cross-react with other antigens. An antibody or antibody fragment that specifically binds to a kinase antigen can be identified, for example, by immunoassays, BlAcore, or other techniques known to those of skill in the art. An antibody or antibody fragment binds specifically to an antigen when it binds to the antigen with higher affinity than to any cross-reactive antigen as determined using experimental techniques, such as RIAs and ELISAs. Typically, a specific or selective reaction will be at least twice the background signal or noise and more typically more than 10 times background. In one embodiment, the anti-phospho antibody is an anti-phosphotyrosine antibody (also referred to as "anti-pTyr" or "anti-pY") that specifically binds to a one or more phosphorylated tyrosine residues of a protein or enzyme, including one or more phosphorylated tyrosine residues of a kinase. In one embodiment, the anti-phospho antibody is an anti-phosphoserine antibody (also referred to as "anti-pSer" or "anti-pS") that specifically binds to one or more phosphorylated serine residues of a protein or enzyme, including one or more phosphorylated serine residues of a kinase. In one embodiment, the anti-phospho antibody is an anti-phosphothreonine antibody (also referred to as "anti-pThr" or "anti-pT") that specifically binds to one or more phosphorylated threonine residues of a protein or enzyme, including one or more phosphorylated threonine residues of a kinase. In certain embodiments, the anti-phospho antibody immunospecifically binds to one or more of phosphorylated tyrosine (Y), serine (S) or threonine (T) residues at one or more specific positions of the kinase. In another certain embodiment, the anti-phospho antibody specifically binds to only one phosphorylated amino acid residue of a protein.

"Compound" or "test compound" refers to one or more organic chemical compounds, inorganic chemical compounds, synthetic nucleic acids, natural nucleic acids, synthetic polypeptides, natural polypeptides, peptide fragments and/or proteins. The terms "compound" or "test compounds" as used herein also includes experimental small molecules, FDA-approved small molecule therapeutics, antibodies developed for antibody-directed therapy and other therapeutic agents.

5.2 Methods of Identifying Proteins Modulated by a Cellular Process

The following embodiments provided herein are exemplary and are not limiting. The methods disclosed herein have a range of applications. The compositions and methods provided herein may be used in vitro and/or in vivo.

In one aspect, provided herein is a method of detecting a target protein modified by a cellular process of interest comprising the steps of: (a) contacting a detectable protein comprising the target protein and a nucleic-acid interacting motif with (i) an antibody that binds the target protein that has been modified by the cellular process of interest, and (ii) a nucleic acid oligomer comprising a nucleic acid sequence that binds the nucleic-acid interacting motif; and (b) detecting the presence of the nucleic acid oligomer that is bound to the detectable protein which is also bound by the antibody; wherein the presence of the nucleic acid oligomer of step (b) indicates the presence of the target protein that has been modified by the cellular process of interest. In some embodiments, the detectable protein is contacted with the antibody before the detectable protein is contacted with the nucleic acid oligomer in step (a). In some embodiments, the detectable protein is contacted with the antibody after the detectable protein is contacted with the nucleic acid oligomer in step (a). In some embodiments, the detectable protein is concurrently contacted with the antibody and the nucleic acid oligomer in step (a).

In some embodiments, the cellular process is selected from acylation, acetylation, deacetylation, formylation, alkylation, methylation, phosphorylation, dephosphorylation, sulfation, oxidation, reduction, hydroxylation, deamidation, carboxylation, disulfide formation, prenylation, glycation, glycosylation, ubiquitination, sumoylation, proteolysis, racemization and isomerization. In a particular embodiment, the cellular process is phosphorylation.

In some embodiments, the target protein is a kinase substrate. In some embodiments, the modified target protein is phosphorylated at one or more residues, and the antibody is an anti-phospho antibody. In some embodiments, the modified target protein is phosphorylated at one or more tyrosine residues, and the antibody is an anti-phosphotyrosine antibody. In some embodiments, the modified target protein is phosphorylated at one or more serine residues, and the antibody is an anti-phosphoserine antibody. In some embodiments, the modified target protein is phosphorylated at one or more threonine residues, and the antibody is an anti-phosphothreonine antibody.

In some embodiments, the target protein is a G-coupled protein receptor, an ion channel protein, a nuclear receptor protein, a transcription factor, a kinase, a cytokine, a growth factor, a hormone, an enzyme, an antibody or a small chain variable fragment (scFv).

In some embodiments, the nucleic acid-interacting motif is a DNA-binding domain. In some embodiments, the DNA-binding domain is a NF-κB DNA binding domain, cro repressor DNA binding domain, lac repressor DNA binding domain, GAL4 DNA binding domain, GCN4 DNA binding domain, Lex-A DNA binding domain, Opaque-2 DNA binding domain or TGA1a DNA binding domain. In particular embodiments, the nucleic acid-interacting motif comprises the amino acid sequence depicted in SEQ ID NO:5 or SEQ ID NO:6.

In some embodiments, the oligomer is between about 50 and 500 nucleotides in length.

In another aspect, provided herein is a method of identifying a test compound which modulates a cellular process, wherein the cellular process modifies a target protein, said method comprising the steps of: (a) contacting a cell or cell lysate comprising a detectable protein with test compound, wherein the detectable protein comprises the target protein and a nucleic-acid interacting motif; (b) contacting the detectable protein with: (i) an antibody that specifically binds to the target protein that has been modified as a result of the cellular process; and (ii) a nucleic acid oligomer comprising a nucleic acid sequence that binds the nucleic-acid interacting motif; and (c) detecting an amount of nucleic acid oligomer bound to the detectable protein that is also bound by the antibody; wherein an increase or decrease in the amount of bound nucleic acid oligomer of step (c) detected in the presence of said test compound relative to the amount of bound nucleic acid oligomer detected in the absence of said test compound indicates that the test compound modulates the cellular process.

In some embodiments, an increase in the amount of bound nucleic acid oligomer of step (c) detected in the presence of said test compound relative to the amount of bound nucleic acid oligomer detected in the absence of said test compound indicates that the test compound agonizes the cellular process. In some embodiments, a decrease in the amount of bound nucleic acid oligomer of step (c) detected in the presence of said test compound relative to the amount of bound nucleic acid oligomer detected in the absence of said test compound indicates that the test compound inhibits the cellular process.

In some embodiments, step (a) comprises contacting a cell comprising the detectable protein. In some embodiments, the cell transiently expresses the detectable protein. In some embodiments, the cell stably expresses the detectable protein.

In some embodiments, the cellular process is selected from acylation, acetylation, deacetylation, formylation, alkylation, methylation, phosphorylation, dephosphorylation, sulfation, oxidation, reduction, hydroxylation, deamidation, carboxylation, disulfide formation, prenylation, glycation, glycosylation, ubiquitination, sumoylation, proteolysis, racemization and isomerization. In a particular embodiment, the cellular process is phosphorylation.

In some embodiments, the target protein is a kinase substrate. In some embodiments, the modified target protein is phosphorylated at one or more tyrosine residues, and the antibody is an anti-phosphotyrosine antibody. In some embodiments, the modified target protein is phosphorylated at one or more serine residues, and the antibody is an anti-phosphoserine antibody. In some embodiments, the modified target protein is phosphorylated at one or more threonine residues, and the antibody is an anti-phosphothreonine antibody.

In some embodiments, the target protein is a G-coupled protein receptor, an ion channel protein, a nuclear receptor protein, a transcription factor, a kinase, a cytokine, a growth factor, a hormone, an enzyme, an antibody or a small chain variable fragment (scFv).

In some embodiments, the nucleic acid-interacting motif is a DNA-binding domain. In some embodiments, the DNA-binding domain is a NF-κB DNA binding domain, cro repressor DNA binding domain, lac repressor DNA binding domain, GAL4 DNA binding domain, GCN4 DNA binding domain, Lex-A DNA binding domain, Opaque-2 DNA binding domain or TGA1a DNA binding domain. In particular embodiments, the nucleic acid-interacting motif comprises the amino acid sequence depicted in SEQ ID NO:5 or SEQ ID NO:6.

In some embodiments, the oligomer is between about 50 and 500 nucleotides in length.

In some embodiments, the kinase substrate is, wherein the antibody specifically binds to phosphorylated Mek1, and step (a) further comprises preparing a positive control sample whereby the cell or cell lysate comprising the detectable protein is contacted with a Braf inhibitor instead of test compound. Within these embodiments, contact with a Braf inhibitor preferably results in a decrease in the amount of bound nucleic acid oligomer detected in step (c), relative to the amount of bound nucleic acid oligomer detected in the absence of inhibitor, thereby indicating that the Braf inhibitor inhibits Braf kinase activity, e.g., inhibits the phosphorylation of MEK1. In some embodiments, the Braf inhibitor is selected from BAY-43-9006, PLX-4720, Chir-265.

In some embodiments, the kinase substrate is Akt1 and the antibody binds to phosphorylated Akt. In some embodiments, the antibody binds to Akt1 phosphorylated at Ser473 or Thr308. In some embodiments, the antibody binds to Akt1 phosphorylated at Thr308. In some embodiments, the antibody binds to Akt1 phosphorylated at Ser473.

In some embodiments, the kinase substrate is FRAP1 or PDPK1, wherein the antibody specifically binds to phosphorylated FRAP1 or phosphorylated PDPK1, respectively, and step (a) further comprises preparing a positive control sample whereby the cell or cell lysate comprising the detectable protein is contacted with a PIK3CA inhibitor instead of test compound. Within these embodiments, contact with a PIK3CA inhibitor preferably results in a decrease in the amount of bound nucleic acid oligomer detected in step (c), relative to the amount of bound nucleic acid oligomer detected in the absence of inhibitor, thereby indicating that the PIK3CA inhibitor inhibits PIK3CA kinase activity, e.g., inhibits the phosphorylation of FRAP1 or PDPK1, respectively. In some embodiments, the PIK3CA inhibitor is selected from PI103, ZSTK-474, wortmannin and PIK-93.

In some embodiments, the kinase substrate is AKT1, wherein the antibody specifically binds to phosphorylated AKT1, and step (a) further comprises preparing a positive control sample whereby the cell or cell lysate comprising the detectable protein is contacted with a PDPK1, FRAP1 or mTOR inhibitor instead of test compound. Within these embodiments, contact with a PDPK1, FRAP1 or mTOR inhibitor preferably results in a decrease in the amount of bound nucleic acid oligomer detected in step (c), relative to the amount of bound nucleic acid oligomer detected in the absence of inhibitor, thereby indicating that the PDPK1, FRAP1 or mTOR inhibitor inhibits PDPK1, FRAP1 or mTOR kinase activity, e.g., inhibits the phosphorylation of AKT1. In some embodiments, the PDPK1 inhibitor is BX-795.

In some embodiments, the kinase substrate is FOXO1 and the antibody specifically binds to phosphorylated FOXO1. In some embodiments, the antibody binds to FOXO1 phosphorylated at Thr24.

In some embodiments, step (a) further comprises preparing a positive control sample whereby the cell or cell lysate comprising a detectable protein is contacted with an AKT1 inhibitor instead of test compound. In some embodiments, the Akt1 inhibitor is GSK-690693.

In some embodiments, the nucleic acid oligomer comprises (a) a first nucleic acid sequence that is a PCR amplification sequence, and (b) a second nucleic acid sequence that binds the nucleic acid-interacting motif, wherein the first nucleic acid sequence is heterologous to the second nucleic acid sequence.

In some embodiments, the method further comprises performing a control experiment to determine whether the test compound competes for binding of the target protein with the antibody that specifically binds to the modified form of the target protein. In preferred embodiments, the methods provided herein are used to identify test compounds that do not compete for binding of the target protein with antibody which specifically binds to the modified form of the target protein.

In some embodiments, the step of detecting an amount of nucleic acid oligomer bound to the detectable protein comprises qPCR amplifying the nucleic acid oligomer that is bound to the detectable protein. In some embodiments, the nucleic acid oligomer is radiolabeled, fluorescently labeled or biotinylated.

In one embodiment, the target protein is modified through a cellular process that takes place inside a cell. In another embodiment, the detectable protein comprising the DNA binding domain and the target protein is obtained from a cell lysate. In another embodiment, the detectable protein comprising the DNA binding domain and the target protein is chemically synthesized. In particular embodiments, the detectable protein comprising the DNA binding domain and the target protein is modified in a cell-free system.

In another aspect, provided herein is a method of identifying a test compound which modulates an enzymatic activity, wherein the enzymatic activity modifies a target protein, said method comprising the steps of: (a) contacting a cell or cell lysate comprising a detectable protein with test compound, wherein the detectable protein comprises the target protein and a nucleic-acid interacting motif; (b) contacting the detectable protein with: (i) an antibody that specifically binds to a target protein that has been modified as a result of the enzymatic activity; and (ii) a nucleic acid oligomer comprising a nucleic acid sequence that binds the nucleic-acid interacting motif; and (c) detecting an amount of nucleic acid oligomer bound to the detectable protein that is also bound by the antibody; wherein an increase or decrease in the amount of bound nucleic acid oligomer of step (c) detected in the presence of said test compound relative to the amount of bound nucleic acid oligomer detected in the absence of said test compound indicates that the test compound modulates the enzymatic activity.

In another aspect, provided herein is a method of identifying a compound that inhibits enzymatic activity, said method comprising the steps of: (a) contacting a cell or cell lysate comprising a detectable protein with test compound, wherein the detectable protein comprises the target protein and a nucleic-acid interacting motif; (b) contacting the detectable protein with: (i) an antibody that specifically binds to the target protein that has been modified as a result of the enzymatic activity; and (ii) a nucleic acid oligomer comprising a nucleic acid sequence that binds the nucleic-acid interacting motif; and (c) detecting an amount of nucleic acid oligomer bound to the detectable protein that is also bound by the antibody; wherein an decrease in the amount of bound nucleic acid oligomer of step (c) detected in the presence of said test compound relative to the amount of bound nucleic acid oligomer detected in the absence of said test compound indicates that the test compound inhibits the enzymatic activity.

In some embodiments, the enzymatic activity is selected from acylation, acetylation, deacetylation, formylation, alkylation, methylation, phosphorylation, dephosphorylation, sulfation, oxidation, reduction, hydroxylation, deamidation, carboxylation, disulfide formation, prenylation, glycosylation, ubiquitination, sumoylation, proteolysis, racemization and isomerization. In a particular embodiment, the enzymatic activity is kinase activity. In a particular embodiment, the enzymatic activity is phosphorylation. In another embodiment, the enzymatic activity is phosphatase activity. In another embodiment, the enzymatic activity is methyl transferase activity. In another embodiment, the enzymatic activity is acetyl transferase activity.

In yet another aspect, provided herein is a method of measuring a compound's $IC_{50}$ against an enzyme, said method comprising the steps of: (a) preparing at least one sample in the absence of the compound and a plurality of samples in the presence of increasing amounts of the compound, wherein each sample is derived from a plurality of cells or cell lysate(s) comprising a detectable protein, wherein the detectable protein comprises a nucleic acid interacting motif and an enzyme substrate; (b) contacting the detectable protein with an antibody that binds the enzyme substrate that has been modified by the cellular process; (c) separating the antibody-bound detectable protein from unbound detectable protein and unbound antibody; (d) contacting the antibody-bound detectable protein to a nucleic acid oligomer that binds to the nucleic acid interacting motif; and (e) detecting the amount of bound nucleic acid oligomer for each sample prepared in step (a); wherein the compound concentration at which the amount of the bound nucleic acid oligomer detected is half the amount of bound nucleic acid oligomer detected in the sample prepared in the absence of compound is the compound's $IC_{50}$ against the enzyme.

Any of the methods described herein can be run in either singleplex or multiplex format. In one exemplary multiplex format, a test compound is screened and tested for its modulatory properties against multiple proteins of interest, each involved in a cellular process of interest, from a panel of such proteins simultaneously. Where multiple proteins are being assayed simultaneously or sequentially, nucleic acid oligomers unique to a protein that is modified by each protein of interest can be used to distinguish the activity of each protein of interest.

5.2.1 Detectable Proteins

In certain embodiments, the protein of interest is a chimeric fusion between a target protein and a heterologous nucleic-acid interacting motif In such chimeric fusions, at least two gene sequences representing each half of the chimera can be fused in-frame, cloned into the appropriate vector and expressed in a host cell of choice. Alternatively, the target protein may be otherwise synthetically linked (e.g., using a polypeptide linker) to the nucleic-acid interacting motif In certain embodiments, the target protein is amino-terminal to the nucleic-acid interacting motif (e.g., DNA-binding protein). In other embodiments, the target protein is carboxy-terminal to the nucleic-acid interacting motif (e.g., DNA-binding protein). The linkage can be direct or indirect. In certain embodiments, the target protein and/or the nucleic-acid interacting motif (e.g., DNA-binding protein) retain the respective activity of the wildtype protein. In certain embodiments, the nucleic acid-interacting motif and a target protein are derived from the same organism, such as a human.

5.2.1.1 Target Protein

As used herein, the term "target protein" refers to any protein of interest that can be modified by as a result of a cellular process such as those described herein. In some embodiments, the target protein is modified by a protein having enzymatic or catalytic activity. In some embodiments, the target protein is a substrate for a kinase, transferase, oxidoreductase, hydrolase, ligase, isomerase or lyase. In one embodiment, the target protein is a human polypeptide or protein. In some embodiments, the target protein may be modified by cleavage, by the addition or removal of functional groups or by undergoing isomerization. In certain embodiments, the target protein is a substrate of a transferase having transferase activities, such as an acyltransferase, glycosyltransferase, amidotransferase or sulfurtransferase. In some embodiments, the target protein is a G-coupled protein receptor, an ion channel protein, a nuclear receptor protein, a transcription factor, a kinase, a cytokine, a growth factor, a hormone, an enzyme, an antibody or a small chain variable fragment (scFv). In another embodiment, the target protein is a substrate for a hydrolase, peptidase, protease or phosphatase. In some embodiments, the target protein is a substrate for a kinase. In some embodiments, the target protein is a substrate for a lipid kinase, such as a lipid kinase of the P13K family (e.g., mTOR). In some embodiments, the target protein is a substrate for a protein kinase (see, e.g., Manning (2002) Science 298:1912). In some embodiments, the target protein is a substrate for a tyrosine kinase, or a serine/threonine kinase. In some embodiments, the target protein is a substrate for a human non-receptor tyrosine kinase, for example, a non-receptor tyrosine kinase that is a member of the ABL, ACK, CSK, MATK, FAK, PYK2, FES, FRK, JAK, SRC-A, SRC-B, TEC, and/or SYK families. In other embodiments, the target protein is a substrate for a human receptor tyrosine kinase, for example, a receptor tyrosine kinase that is member of the ALK, AXL, DDR, EGFR, EPH, FGFR, INSR, MET, MUSK, PDGFR, PTK7, RET, ROR, ROS, RYK, TIE, TRK, VEGFR, AATYK, and/or SuRTK106 families. In some embodiments, the target protein is a substrate for PIK3CA, FRAP1, PDPK1, AKT1, BRaf, or MEK1. In particular embodiments, the target protein is a histone (e.g., histone H3). In particular embodiments, the target protein is pro-apoptotic protein (e.g., BAD). In particular embodiments, the target protein is a transcription factor (e.g., STAT5a, STAT6). In particular embodiments, the target protein is a cyclin (e.g. Cyclin B1). In particular embodiments, the target protein is a receptor (e.g., androgen receptor).

In certain embodiments, the target protein is an enzyme that is modified by autophosphorylation. In certain embodiments, the target protein is a kinase that is modified by auto-phosphorylation. Examples of kinases that autophosphorylate include but is not limited to CSF1R, Kit, Axl, EGFR, Flt3, AuroraA, Brk, Jak2, Jak3, Fak, Src and Tnk2.

In certain embodiments, the target protein is a catalytically inactive enzyme that is capable of being modified as a substrate, but is not able to affect downstream activation. In specific embodiments, the target protein is a kinase that is capable of being phosphorylated but which has a mutation in the catalytic residue of the kinase domain rendering the kinase inactive.

In certain embodiments, a nucleic acid encoding the detectable protein is cloned into a plasmid expression vector and transiently transfected into a cell line, resulting in transient expression of the detectable protein. In certain embodiment, a nucleic acid encoding the detectable protein is cloned into a plasmid expression vector and stably transfected into a cell line, resulting in stable expression of the detectable protein. In certain embodiments, a nucleic acid encoding the detectable protein is cloned into a constitutive plasmid expression vector and transfected into a cell line, resulting in constitutive expression of the detectable protein. In specific embodiments, constitutive expression is under the control of a CMV promoter. In certain embodiments, the nucleic acid encoding the detectable protein is cloned into an inducible plasmid expression vector and transfected into a cell line, resulting in inducible expression of the detectable protein. In specific embodiments, inducible expression is under the control of a CMV promoter containing operator sites. In a more specific embodiment, the operator sites are tetracycline operator 2 sites. In yet another embodiment, the inducible plasmid expression vector is a tetracycline-regulated expression vector.

5.2.1.2 Nucleic Acid Interacting Motif

Nucleic-acid interacting motifs, e.g., DNA-binding domains are known in the art, and exemplary sequences suitable for use in the methods provided herein are provided in Table 1. Nucleic-acid interacting motifs may include the DNA-binding domain of transcription factors, including transcriptional activators and repressors. Examples of suitable DNA-binding domains include NF-κB (eukaryotic), cro repressor (λ bacteriophage), lac repressor (yeast), GAL4 (yeast), GCN4 (yeast), Lex-A (*E. coli*), Opaque-2 (maize) and TGA1a (tobacco). Suitable DNA-binding domains can also include synthetic DNA-binding domains constructed by combining different pieces of naturally occurring and/or engineered DNA-binding motifs, such as synthetic zinc fingers, leucine zippers, winged helix, helix-loop-helix, homeodomain and POU domain. In other embodiments, the nucleic acid interaction motif may be a full-length, partial-length or a functional fragment of a DNA-metabolizing enzyme, such as DNA ligases, DNA repair enzymes, restriction enzymes or DNA methyltransferases.

Suitability of the DNA-binding domain may depend of the association times of a particular DNA-binding domain to its target sequence. For example, NF-κB is considered to form a strong association with its target DNA sequence, with a dissociation half-life of over 4 hours. (See Speight et al. (2001) Chem. Biol. 8:951-965).

In certain embodiments, the nucleic acid interacting motif is present in tandem repeat to permit cis dimerization. In another particular embodiment, the NF-κB motif is present in tandem repeat to permit NF-κB cis dimerization.

5.2.1.3 Methods of Making Detectable Proteins

As discussed herein, a detectable protein comprises a target protein linked to a nucleic-acid interacting motif, and can optionally comprise a signal peptide if the target protein is a membrane protein. Detectable proteins provided herein can be made using any of a variety of methods, e.g., recombinant or synthetic methods, well known to those of skill in the art.

In one aspect, a detectable protein can be made using standard recombinant DNA techniques. For example, a polynucleotide comprising the coding sequence of a detectable protein, e.g., the coding sequence for a target protein joined in-frame with the coding sequence of a nucleic-acid interacting motif in an expression vector, e.g., a plasmid vector, can be expressed in any suitable cell, e.g., a bacterial or mammalian cell.

In certain embodiments, a cell is used to express a single detectable protein. In other embodiments, a cell is engineered to express greater than one form of detectable protein, e.g., is engineered to express a detectable protein comprising a first target protein, and also a detectable protein comprising a different target protein.

In certain embodiments, in addition to the coding sequence of a target protein and the nucleic-acid interacting motif, the coding sequence further comprises the amino acid sequence of a signal peptide. The signal peptide is a short amino acid sequence that directs a newly synthesized protein into the endoplasmic reticulum (ER) to become a lysosomal protein, secretory protein or membrane protein that spans the plasma membrane. In one embodiment, where the target protein is a lysosomal protein, a secretory protein or a membrane protein, a signal peptide is employed to direct the target protein to its final destination. The location of the signal peptide can be placed in any position that does not interfere with the expression or activity of the target protein, the nucleic-acid interacting motif. For example, the coding sequence of the signal peptide can be placed upstream (5') or downstream (3') of the coding sequence of the target protein such that the signal peptide is amino or carboxy to the target protein in the expressed detectable protein, respectively. Likewise, the coding sequence of the signal peptide can be placed upstream (5') or downstream (3') of the coding sequence of the nucleic-acid interacting motif such that the signal peptide is amino or carboxy to the nucleic-acid interacting motif in the expressed detectable protein, respectively. In certain embodiments, the signal peptide is an internal signal sequence that is found within the target protein sequence. In one embodiment, the fusion protein comprises, from the amino to carboxy terminus, the signal peptide, the target protein, an optional linker sequence and the nucleic acid interacting motif In particular embodiments, the signal peptide is present at the amino terminal end of the detectable protein. In particular embodiments, the detectable protein comprises, from the amino to carboxy terminus, a signal peptide, the target protein, and the nucleic-acid interacting motif. In particular embodiments, the detectable protein comprises, from the amino to carboxy terminus, a signal peptide, the target protein, and the nucleic-acid interacting motif, wherein the target protein is a receptor. In particular embodiments, a linker sequence is present between the target protein and the nucleic acid interacting motif In certain embodiments, the linker sequence is 10-20 amino acids long. In certain embodiments, the linker sequence is 16, 17 or 18 amino acids long. In other embodiments, the linker sequence is a flexible linker. In yet another embodiment, the linker sequence is an enzymatic cleavage site that may be recognized by a protease. In such an embodiment, the target protein may be cleaved from the nucleic acid motif by a protease. A non-limiting example of such a cleavage site is the sequence recognized and cleaved by the tobacco etch virus (TEV) protease.

In certain embodiments, the detectable protein comprises a target protein linked to the amino terminus of a nucleic-acid interacting motif In such embodiments, the coding sequence of the detectable protein is arranged accordingly. Thus, in one embodiment, the coding sequence of the target protein is positioned in-frame with the coding sequence of the nucleic-acid interacting motif such that the carboxy-most amino acid residue of the target protein is adjacent to the amino-most amino acid residue of the nucleic-acid interacting motif in the expressed detectable protein. In an alternate embodiment, the coding sequence of the target protein is positioned in-frame with the coding sequence of an amino acid linker sequence, which is, in turn, positioned in-frame with the coding sequence of the nucleic-acid interacting motif In such an embodiment, the amino acid sequence of the target protein is also linked to the amino terminus of the nucleic-acid interacting motif, but is linked via the linker sequence.

Likewise, in certain embodiments, the detectable protein comprises a target protein linked to the carboxy terminus of a nucleic-acid interacting motif In such embodiments, the coding sequence of the detectable protein is arranged accordingly. Thus, in one embodiment, the coding sequence of the nucleic-acid interacting motif is positioned in-frame with the coding sequence of the target protein such that the carboxy-most amino acid residue of the nucleic-acid interacting motif is adjacent to the amino-most amino acid residue of the target protein in the expressed detectable protein. In an alternate embodiment, the coding sequence of the nucleic-acid interacting motif is positioned in-frame with the coding sequence of an amino acid linker sequence, which is, in turn, positioned in-frame with the coding sequence of the target protein. In such an embodiment, the amino acid sequence of the target protein is also linked to the carboxy terminus of the nucleic-acid interacting motif, but is linked via the linker sequence.

Techniques for construction of expression vectors and expression of genes in cells comprising the expression vectors are well known in the art. See, e.g., Sambrook et al., 2001, Molecular Cloning—A Laboratory Manual, $3^{rd}$ edition, Cold Spring Harbor Laboratory, Cold Spring Harbor, N.Y., and Ausubel et al., eds., Current Edition, Current Protocols in Molecular Biology, Greene Publishing Associates and Wiley Interscience, NY.

Useful promoters for use in expression vectors include, but are not limited to, an arabinose promoter, a metallothionein promoter, a constitutive adenovirus major late promoter, a dexamethasone-inducible MMTV promoter, a SV40 promoter, a MRP pol III promoter, a constitutive MPSV promoter, a tetracycline-inducible CMV promoter (such as the human immediate-early CMV promoter), and a constitutive CMV promoter. Inducible promoters also find utility in practicing the methods described herein, such as a promoter containing the tet responsive element (TRE) in the tet-on or tet-off system, e.g., the T-REx™ system (Invitrogen Cat No. K1020-02), the metallothienein promoter which can be upregulated by addition of certain metal salts and rapamycin inducible promoters (Rivera et al., 1996, Nature Med, 2(9): 1028-1032; Ye et al., 2000, Science 283: 88-91; Sawyer T K et al., 2002, Mini Rev Med Chem. 2(5):475-88). Large numbers of suitable regulatable vectors and promoters for use in practicing the current invention are known to those of skill in the art and many are commercially available.

The expression vectors should contain expression and replication signals compatible with the cell in which the detectable proteins are expressed. Expression vectors useful for constructs encoding detectable proteins include viral vectors such as retroviruses, adenoviruses and adenoassociated viruses, plasmid vectors, cosmids, and the like. Viral and plasmid vectors are preferred for transfecting the expression vectors into mammalian cells. For example, the expression vector pcDNA1 (Invitrogen, San Diego, Calif.), in which the expression control sequence comprises the CMV promoter, provides good rates of transfection and expression into such cells.

Detectable proteins can also be made, for example, using chemical synthetic methods, or a combination of synthetic and recombinant methods. For example, detectable proteins can be synthetically produced using standard polypeptide synthesis techniques well known by those of skill in the art. Alternatively, portions of a detectable protein can be purified, or recombinantly expressed using, e.g., techniques such as those described herein, and the portions can be linked using synthetic techniques to yield complete detectable proteins.

In embodiments in which portions of a detectable protein are expressed or purified and then linked, the linkage can be via covalent, e.g., peptide bond, or non-covalent linkage, and can be direct or via a linker moiety, e.g., a linker moiety that links a target protein with a nucleic-acid interacting motif.

Any of a variety of linkages can be utilized, including, but not limited to ether, ester, thioether, thioester, amide, imide, disulfide, peptide, or other linkages. Linkage can be likewise be via any of a variety of functional groups, for example, sulfhydryl (—S), carboxylic acid (COOH) or free amine (—NH2) groups. The skilled artisan can routinely select the appropriate linkage, optional linker, and method for attaching the linking the portions of the detectable protein based, for example, on the physical and chemical properties of the elements, e.g., the nucleic-acid interacting motif and/or the target protein, of the detectable protein.

In embodiments where a linker is utilized, the linker can directly link portions of the detectable protein, e.g., a nucleic-acid interacting motif and a target protein polypeptide. In other embodiments, the linker itself can comprises two or more molecules that associate to link portions of the detectable protein, e.g., a nucleic-acid interacting motif and a target protein For example, linkage may be via a biotin molecule attached, e.g., to a nucleic-acid interacting motif and streptavidin attached to the target protein polypeptide. Exemplary linkers include, but are not limited to, straight or branched-chain carbon linkers, heterocyclic carbon linkers, substituted carbon linkers, unsaturated carbon linkers, aromatic carbon linkers, peptide linkers, etc.

In embodiments where a linker is used to connect the nucleic-acid interacting motif to the target protein polypeptide, the linkers can be attached to the nucleic-acid interacting motif and/or the target protein polypeptide by any means or method known by one of skill in the art without limitation.

Furthermore, portions of the detectable protein to be linked, e.g., a nucleic-acid interacting motif and a target protein, can be derivatized as appropriate to facilitate linkage to another portion of the detectable protein, or to a linker. Such derivatization can be accomplished, for example, by attaching a suitable derivative or derivatives such as those available from Pierce Chemical Company, Rockford, Ill. Alternatively, derivatization may involve chemical treatment of one or more portions of the detectable protein to be linked, e.g., a nucleic-acid interacting motif and/or a target protein. For example, the skilled artisan can routinely generate free sulfhydryl groups on proteins to provide a reactive moiety for making a disulfide, thioether, thioester, etc. linkage. See, e.g., U.S. Pat. No. 4,659,839.

Any of the linking methods described herein can be used to link portions of detectable proteins, e.g., a nucleic-acid interacting motif and a target protein, in various configurations. For example, the carboxy terminus of the nucleic-acid interacting motif may be linked, directly or indirectly, to the amino terminus of the target protein polypeptide. In some embodiments, the carboxy terminus of the target protein may be linked to the amino terminus of the nucleic-acid interacting motif, either directly or indirectly. In other embodiments, the amino terminus of the nucleic-acid interacting motif may be linked, either directly or indirectly, to the amino terminus of the target protein. In other embodiments, the carboxy terminus of the nucleic-acid interacting motif may be linked, either directly or indirectly, to the carboxy terminus of the target protein. As discussed above, as used herein, "linked to" an amino terminus or a carboxy terminus does not necessarily connote a direct linkage to the amino-most, or carboxy-most amino acid of the polypeptide, but can also be via a linker, e.g., an amino acid sequence of one or more residues, e.g., 2, 3, 4, 5, 10, 15, 20, 25, or more amino acid residues. It is noted that any detectable protein made via methods described above can be utilized as part of the methods described herein.

5.2.2 Antibodies

Antibodies for use in the methods and kits provided herein include, but are not limited to, polyclonal antibodies, synthetic antibodies, monoclonal antibodies, recombinantly produced antibodies, multispecific antibodies (including bi-specific antibodies), human antibodies, humanized antibodies, mouse antibodies, goat antibodies, rabbit antibodies, chimeric antibodies, intrabodies, single-chain Fvs (scFv) (e.g., including monospecific, bispecific, etc.), camelized antibodies, Fab fragments, F(ab')$_2$ fragments, disulfide-linked Fvs (sdFv), anti-idiotypic (anti-Id) antibodies, and epitope-binding fragments of any of the above.

In particular embodiments, antibodies for use in the methods and kits provided herein include immunoglobulin molecules and immunologically active portions of immunoglobulin molecules. The immunoglobulin molecules provided herein can be of any type (e.g., IgG, IgE, IgM, IgD, IgA and IgY), class (e.g., IgG1, IgG2, IgG3, IgG4, IgA1 and IgA2) or subclass of immunoglobulin molecule.

The antibodies that can be used include variants and derivatives of immunoglobulins, including but not limited to fragments that retain the ability to specifically bind to an epitope. Preferred fragments include Fab fragments (an antibody fragment that contains the antigen-binding domain and comprises a light chain and part of a heavy chain bridged by a disulfide bond); Fab' (an antibody fragment containing a single antibinding domain comprising an Fab and an additional portion of the heavy chain through the hinge region); F(ab')$_2$ (two Fab' molecules joined by interchain disulfide bonds in the hinge regions of the heavy chains; the Fab' molecules may be directed toward the same or different epitopes); a bispecific Fab (a Fab molecule having two antigen binding domains, each of which may be directed to a different epitope); a single chain Fab chain comprising a variable region, also known as, a sFv (the variable, antigen-binding determinative region of a single light and heavy chain of an antibody linked together by a chain of 10-25 amino acids); a disulfide-linked Fv, or dsFv (the variable, antigen-binding determinative region of a single light and heavy chain of an antibody linked together by a disulfide bond); a camelized VH (the variable, antigen-binding determinative region of a single heavy chain of an antibody in which some amino acids at the VH interface are those found in the heavy chain of naturally occurring camel antibodies); a bispecific sFv (a sFv or a dsFv molecule having two antigen-binding domains, each of which may be directed to a different epitope); a diabody (a dimerized sFv formed when the VH domain of a first sFv assembles with the VL domain of a second sFv and the VL domain of the first sFv assembles with the VH domain of the second sFv; the two antigen-binding regions of the diabody may be directed towards the same or different epitopes); and a triabody (a trimerized sFv, formed in a manner similar to a diabody, but in which three antigen-binding domains are created in a single complex; the three antigen binding domains may be directed towards the same or different epitopes). Antibodies that are derivatives of immunoglobulins also include one or more CDR sequences of an antibody combining site. The CDR sequences may be linked together on a scaffold when two or more CDR sequences are present. In certain embodiments, the antibody to be used in the invention comprises a single-chain Fv ("scFv"). scFvs are antibody fragments comprising the VH and VL domains of an antibody, wherein these domains are present in a single polypeptide chain. Generally, the scFv polypeptide further comprises a polypeptide linker between the VH and VL domains which enables the scFv to form the desired structure for antigen binding. For a review of scFvs see Pluckthun in The Pharmacology of Monoclonal Antibodies, vol. 113, Rosenburg and Moore eds. Springer-Verlag, New York, pp. 269-315 (1994).

Antibodies for use in the methods and kits provided herein may be from any animal origin including birds and mammals (e.g., human, murine, donkey, sheep, rabbit, goat, guinea pig, camel, horse, or chicken). In certain embodiments of the methods and kits provided herein, the antibodies of the invention are human or humanized monoclonal antibodies. As used herein, "human" antibodies include antibodies having the amino acid sequence of a human immunoglobulin and include antibodies isolated from human immunoglobulin libraries or from mice that express antibodies from human genes.

In certain embodiments, an antibody that specifically binds to a target protein that has been modified by a cellular process does not bind or cross react with the unmodified form of the target protein. Antibodies having specificity for a particular protein modification, e.g., for particular modified residues, are well known in the art. Thus, any antibody known in the art having specificity for a protein modification, including but not limited to, acylation, acetylation, deacetylation, formylation, alkylation, methylation, phosphorylation, dephosphorylation, sulfation, oxidation, reduction, hydroxylation, deamidation, carboxylation, disulfide formation, prenylation, glycation, glycosylation, ubiquitination, sumoylation, proteolysis, racemization and isomerization, can be used in the methods provided herein. In some embodiments, the antibody used in the methods herein is an anti-phospho antibody. In another embodiment, the antibody used in the methods herein is an anti-methyl antibody. In another embodiment, the antibody used in the methods herein is an anti-acetyl antibody.

In particular embodiments where the target protein is Histone H3, useful antibodies that specifically bind to modified forms of Histone H3 include, but are not limited to anti-acetyl histone H3 (Lys5), (Epitomics, Novus Biologicals); anti-acetyl histone H3 (Lys12) (Novus Biologicals); anti-acetyl histone H3 (BioVision, EMD Biosciences); anti-acetyl histone H3 (Lys9), (Active Motif, USBIO, Novus Biological); anti-acetyl histone H3 (Lys14), anti-acetyl histone H3 (Lys18), (Active Motif, USBIO, Epitmoics); anti-acetyl histone H3 (Lys24) (Santa Cruz Biotechnology); anti-acetyl histone H3 (Lys23), anti-acetyl histone H3 (Lys27), anti- acetyl histone H3 (Lys56), (Active Motif), Epitomics); anti-acetyl histone H3 (Lys9/Lys14) (Cell Signaling Technology, Santa Cruz Biotechnology); anti-acetyl histone H3 (Lys9/Lys18) (USBIO); anti-panmethyl histone H3 (Lys9) (Cell Signaling Technology, Active Motif, USBIO); anti-monomethyl histone H3 (Lys9), anti-monomethyl histone H3 (Lys56), anti-monomethyl histone H3 (Lys79) (Active Motif); anti-phospho monomethyl histone H3 (Lys4) (Cell Signaling Technology); anti-dimethyl histone H3 (Lys4), anti-dimethyl histone H3 (Lys9), histone H3 (Lys27), anti-dimethyl histone H3 (Lys79), (Cell Signaling Technology, Active Motif, USBIO); anti-dimethyl histone H3 (Lys80) (Santa Cruz Biotechnology); anti-dimethyl histone H3 (Lys56), (Cell Signaling Technology, Active Motif); (Cell Signaling Technology); anti-dimethyl histone H3 (Lys36), (Active Motif); anti-trimethyl histone H3 (Lys9), anti-trimethyl histone H3 (Lys27) (Active Motif); anti-trimethyl histone H3 (Lys4) (Epitomics); anti-phospho(Thr80) anti-trimethyl (Thr79) histone H3 (USBIO); anti-phospho(Thr3) anti-methyl (Lys4) histone H3 (Lifespan Biosciences); anti-acetyl (Lys9) anti-phospho (Ser10) histone H3 (USBIO); anti-acetyl (Lys15) anti-phospho (Ser11) histone H3 (Santa Cruz Biotechnology); and anti-phospho histone H3 (Ser28) (Santa Cruz Biotechnology).

In particular embodiments where the target protein is Cyclin B1, useful antibodies that specifically bind to modified forms of Cyclin B1 include, but are not limited to anti-phospho cyclin B1 (Ser 126) (Rockland, Meridian Life Science); and anti-phospho cyclin B1 (Ser 133) (Cell Signaling Technology).

In particular embodiments where the target protein is BAD, useful antibodies that specifically bind to modified forms of BAD include, but are not limited to anti-phospho BAD (Ser 112), (Immuno-Biological Laboratories, Assay Designs, Cell Signaling Technology, IMGENEX, MBL International); anti-phospho BAD (Ser 136), (Immuno-Biological Laboratories, Assay Designs); and anti-phospho BAD (Ser 155), (Immuno-Biological Laboratories, IMGENEX).

In particular embodiments where the target protein is STAT5A, useful antibodies that specifically bind to modified forms of STAT5A include, but are not limited to anti-phospho STATS (Tyr694) (Rockland, ECM Biosciences, Cell Signaling Technology, Abgent, Immuno-Biological Laboratories, USBIO, LifeSpan Biosciences, MBL International,; RayBiotech, Biotrend, IMGENEX, AnaSpec, Abcam, EMD Biosciences); anti-phospho STATS (Tyr695/Tyr699) (RayBiotech); anti-phospho STAT5A (Ser 127/Ser128); anti-phopsho STAT5A (Ser 780) (Abgent); anti-phopsho STAT5A (Ser 780) (IMGENEX); and anti-phospho STAT5A/B.

In particular embodiments where the target protein is STAT6, useful antibodies that specifically bind to modified forms of STAT6 include, but are not limited to anti-phospho STAT6 (Thr641) (Cell Signaling Technology, R&D Systems, Biotrend, MBL International, RayBiotech, IMGENEX, Biovision, Millipore, EMD Biosciences); and anti-phospho STAT6 (Thr645) (IMGENEX, Abcam).

Other antibodies for detection of protein modification include anti-farnesyl antibodies (Sigma) and anti-O-glycation antibodies (Millipore, Acris Antibodies GmbH, GeneTex, Fitgerald Industries Internationl). Custom monoclonal or polyclonal antibodies that recognize and bind to specific protein modifications may be prepared.

In some embodiments, the assay methods are carried out using solid phase assay formats. In specific embodiments of the methods and kits provided herein, the antibody is immobilized on a solid support. As used herein, a "solid support" is, without limitation, any column (or column material), bead, test tube, microtiter dish, particle (for example, magnetic, agarose or sepharose beads), microchip (for example, glass, fiberglass, latex, silicon, silicon-glass, or gold chip), or membrane (for example, the membrane of a liposome or vesicle), a plastic material (for example, polystyrene or polyvinylchloride, or sensor chip (for example, those used with a BlAcore system) to which an antibody may be bound, either directly or indirectly (for example, through other binding partner intermediates such as other antibodies, Protein A or Protein G), or in which an antibody may be embedded (for example, through a receptor or channel). In particular embodiments, the antibody is indirectly immobilized via the immobilization of Protein G on the solid support.

Antibodies used in the assay methods can be "captured" using any standard procedure, for example, by biotinylation of the antibody, followed by capture of biotinylated antibody using immobilized streptavidin (for example, streptavidin immobilized on magnetic beads or a column). Target proteins that bind to the antibody (and nucleic acid oligomers, which bind to the detectable protein) will remain bound to the solid support, while unbound binding reagents (e.g., target proteins and nucleic acid oligomers) can be washed away. Following capture of bound target protein, a nucleic acid oligomer that has bound the target via binding to the nucleic acid interacting motif of the detectable protein can routinely be detected, e.g., by performing a PCR reaction using primers which hybridize to the nucleic acid oligomer. In certain embodiments, the PCR reaction is carried out using standard quantitative methods (for example, using Taq Man by Perkin-Elmer). In some embodiments, multiple protein of interest-nucleic acid oligomer complexes are retained by the solid support, in which case the individual members of the isolated pool can be identified, such as through the amplification of each unique nucleic acid oligomer, which is specific for a particular protein of interest, e.g., in a panel.

In certain embodiments, the solid support to which the antibody is bound is a magnetic bead. In certain embodiments, the antibody is a biotinylated antibody that is immobilized onto a streptavidin-coated bead (e.g., Invitrogen's Dynabeads™ M280. In certain embodiments, the biotinylated antibody is a secondary antibody that is used to capture a primary antibody that in turn is used to recognize and bind to the modified target protein. In certain embodiments, the antibody is immobilized onto a protein G bead (Invitrogen's Dynabeads™ Protein G). In certain embodiments, the antibody is immobilized onto a protein A bead (Invitrogen's Dynabeads™ Protein A). In some embodiments, the antibody is immobilized by being bound to a secondary antibody that is immobilized on a solid surface (e.g., Dynabeads® M-280 Sheep anti-Mouse IgG (Invitrogen); Dynabeads® M-280 Sheep anti-Rabbit IgG (Invitrogen).

In certain embodiments, where elution of the antibody-target protein complex is desired, for example for the PCR detection of the nucleic acid oligomer, elution of the protein complex may be carried out using commercially available elution buffers. In certain embodiments, where the antibody-target protein complex is immobilized using a protein G bead, the elution may be carried out using phenyl phosphate or using a commercially available low pH buffer. In certain embodiments, the immobilized antibody, e.g., either primary antibody or secondary antibody, contains a scissile linker capable of being cleaved chemically or enzymatically. In one embodiment, the scissile linker is capable of being cleaved by a phosphine or dithiol mediated reduction. In a particular embodiment, the phosphine is tris-(2-carboxyethyl) phosphine (TCEP).

In certain embodiments, the antibody is immobilized in a well of a plate with a plurality of wells, such as a multi-well plate or a multi-domain multi-well plate. The use of multi-well assay plates allows for the parallel processing and analysis of multiple samples distributed in multiple wells of a plate. Multi-well assay plates (also known as microplates or microtiter plates) can take a variety of forms, sizes and shapes (e.g., 96-, 384-, 1536-, or 9600-well plates; round- or flat-bottom multi-well plates). The methods provided herein, when carried out in standardized plate formats can take advantage of readily available equipment for storing and moving these plates as well as readily available equipment for rapidly dispensing liquids in and out of the plates (e.g., multi-well pipettes, plate washers and the like). Exemplary multi-well plate formats that can be used in the methods provided herein include those found on 96-well plates (12×8 array of wells), 384-well plates (24×16 array of wells) and 1536-well plate (48×32 array of well). Other formats that may be used in the methods provided herein include, but are not limited to, single or multi-well plates comprising a plurality of domains.

5.2.3 Nucleic Acid Oligomer

As used herein, a nucleic acid oligomer binds a nucleic acid-interacting motif of a target protein. In certain embodiments, a nucleic acid oligomer comprises (a) a first nucleic acid sequence that is a PCR amplification sequence ("or amplicons") having a reporter function, and (b) a second nucleic acid sequence that binds the nucleic acid-interacting motif having a protein capture or "tagging" function. In particular embodiments, the first nucleic acid sequence is heterologous to, that is, is not normally found contiguous to, the second nucleic acid sequence. A detectable protein comprising a target protein and a nucleic acid-interacting motif, such as a DNA-binding protein, may be captured or "tagged" by the nucleic acid oligomer through, for example, a DNA-protein complex formation.

In one embodiment, the nucleic acid oligomer comprises an amplicon linked to a target DNA sequence specifically recognizable by a DNA-binding protein (e.g., NFκB, cro repressor, GAL4, GCN4, LexA, Opaque-2 and TGA1a). In another embodiment, the nucleic acid oligomer comprises an amplicon linked to the cognate DNA sequence for the DNA-binding domain of a transcription factor. In one embodiment, the second nucleic acid sequence comprises a recognition sequence for either a naturally-occurring or synthetic DNA-binding protein. In specific embodiments, the first nucleic acid sequence comprising the PCR amplification sequence is separate and distinct from the second nucleic acid comprising the nucleic acid-interacting motif In such embodiments, the nucleic acid oligomer is capable of binding or otherwise linking to a protein of interest having a DNA-binding component specifically recognizing the nucleic acid oligomer. The nucleic acid oligomer may then be detected and/or quantified using, e.g., quantitative PCR (qPCR) or the nucleic acid oligomer may be PCR-amplified and detected by mass spectrometry. In some embodiments, a second reporter function is employed during the PCR amplification step. In one specific embodiment, during the PCR amplification step, the nucleic acid oligomer undergoes a primer extension step at which time a second reporter function such as a fluorescent tag becomes attached to the nucleic acid oligomer.

In one embodiment, the nucleic-acid oligomer is detected and/or quantified by qPCR. Nucleic acid oligomer detection by qPCR has the advantage of being not only a reliable quantitative detection method but also a highly sensitive and highly selective detection method. Because of the highly sensitive nature of the qPCR detection method, this method enables the detection of very small amounts of the target protein and reduces the need for scarce and expensive assay components, such as recombinant proteins. Because of the highly specific nature of the qPCR detection method, qPCR also enables the detection of specific DNA sequences in complex heterogeneous mixtures, and obviates the need for any sort of purification steps normally done to protein samples to either improve or enhance protein detection.

The amplifiable sequence hybridizes or is capable of hybridizing to a PCR primer in a sequence-specific manner. In certain embodiments, the nucleic acid oligomer comprises a plurality of amplicons, for example, two, three, four, five, six, seven, eight, nine, ten or more amplicons. In some embodiments, the plurality of amplicons are tandem repeats of a single amplicon. In certain embodiments, the amplicon is amplifiable by quantitative PCR which permits quantification of the protein tagged by such a nucleic acid oligomer. In a specific amplification method, amplification of a PCR sequence includes combining the nucleic acid containing the PCR amplification template, PCR primer and qPCR probe in a standard PCR reaction mixture (generally, a mixture having a final concentration of 10 mM Tris—HCl (pH 8.3 at 25° C.), 1-4 mM $MgCl_2$ 0.1-1 mM dNTP), and treating the sample first under Hot Start conditions (for example, heating to 95° C. for 5 minutes) to minimize nonspecific annealing or mispriming, followed by a denaturation step (for example, 95° C. for 45 seconds), followed by an annealing step (55° C. for 1 minute), and followed by an extension step (72° C. for 1 minute), with up to forty rounds of the consecutive steps of denaturation, annealing and extension, to complete the amplification of the qPCR signal.

In one embodiment, the length of the nucleic acid oligomer is between about 50 and about 100, about 50 and about 200, about 50 and about 300, about 50 and about 400, about 50 and about 500, about 100 and about 200, about 100 and about 300, about 100 and about 400, about 100 and about 500, about 200 and about 300, about 200 and about 400, about 200 and about 500, about 300 and about 400, about 300 and about 500, or about 400 and about 500 nucleotides in length.

As used herein, a reporter function refers to a feature of the nucleic acid oligomer that allows it to be visualized or otherwise detected or quantified and which therefore allows for the captured or "tagged" protein to be indirectly visualized or otherwise detected or quantified. In certain embodiments, the reporter function of a nucleic acid oligomer is detected by nucleic acid-based readouts, including but not limited to PCR, qPCR (Applied Biosystems Inc./ABI, BioTrove), DNA microarray (Affymetrix's GeneChip®), bead array (Illumina's BeadArray Technology, Luminex's xMAP technology), DNA capillary array or capillary electrophoresis (Applied Biosystems Inc./ABI, Beckman Coulter's GenomeLab™ GeXP Genetic Analysis System), nanotechnology (Nanostring®'s nCounter™ Analysis System), DNA sequencing (454, Illumina's Solexa, Life Technology's SOLiD™ System Sequencing, Applied Biosciences Inc./ABI) and by mass spectrometry (Sequenom ®, BioTrove).

In certain embodiments, the reporter function of the nucleic acid oligomer comes from the radiolabeling, fluorescent labeling or biotinylation of the nucleic acid oligomer. The nucleic acid oligomer may be single- or double-stranded DNA, single- or double-stranded RNA, DNA-RNA hybrid, RNA-RNA hybrid, or their native or synthetic derivatives, analogs and fragments thereof In some embodiments, the nucleic acid oligomer is DNA, and the reporter function label can be introduced to the DNA, for example, by any standard enzymatic reaction, such as nick translation, or by terminal labeling, with $^{32}P$, $^{125}I$ or biotin-labeled deoxynucleotide triphosphates (dNTPs), or the label can be introduced as an intercalating agent. There are many fluorescent or luminescent groups that are commercially available and can be used to label the nucleic acid oligomer. Some examples of fluorescent labels that can be used to label the nucleic acid oligomer are fluorescein, rhodamine and coumarin and their commercial derivatives such as Texas Red® and Alexa Fluor®. Examples of luminescent groups are lanthanide complexes and luminescent nanoparticles. In one embodiment, the nucleic acid oligomer does not initially have a reporter function, but a reporter function is added before the nucleic acid detection step.

Exemplary nucleic acid oligomers and nucleic acid interacting motif pairs are shown in Table 1. DNA-binding protein may include, for example, the DNA-binding domain of transcription factors, including transcriptional activators and repressors. Examples of suitable DNA-binding domains include NF-κB (eukaryotic), cro repressor (λbacteriophage), lac repressor (*E. coli*), GAL4 (yeast), GCN4 (yeast), Lex-A (*E. coli*), Opaque-2 (maize) and TGA1a (tobacco). Suitability of the DNA-binding domain may also depend of the association times of a particular DNA-binding domain to its target sequence. For example, NF-κB is considered to form a strong association with its target DNA sequence, with a dissociation half-life of over 4 hours. (See Speight et al. (2001) *Chem. Biol.* 8:951-965). Suitable DNA-binding domains also include synthetic DNA-binding domains constructed by combining different pieces of naturally occurring and/or engineered DNA-binding motifs, such as synthetic zinc fingers, leucine zippers, winged helix, helix-loop-helix, homeodomain and POU domain. The detectable protein may be captured or "tagged" through the recognition of the DNA-binding-domain to a certain binding recognition sequence of the nucleic acid oligomer. In another embodiment of the invention, the nucleic acid interacting motif may be a full-length, partial-length or a functional fragment of a DNA-metabolizing enzyme described herein, such as DNA ligases, DNA repair enzymes, restriction enzymes or DNA methyltransferases.

TABLE 1

Exemplary Nucleic Acid Oligomer, Nucleic Acid Interacting Motif and Nucleic Acid Interacting Motif Recognition Sequences

| | |
|---|---|
| Nucleic acid oligomers for NF-κB binding | TTGTGAATTGCTGACCGTAGATGTCAACTTTGACCATCA GACAACGTTTCTCCATTCCAATTATGCGAGAATCCT<u>AGG GAATTCCCC</u>TAGATCGCATG (SEQ ID NO: 1). In this embodiment, the amplicon sequence is the sequence preceding the underlined region. The NFκB recognition sequence is the underlined region. CGGCGTAAAAACGAATACCATGTCTCTCATCGCTCGACT CATTCTTTCCAAAATTTCGCGGAACCAGG<u>GGGAATTCCC</u> CTAGATCGCATG (SEQ ID NO: 2). In this embodiment, the amplicon sequence is the sequence preceding the underlined region. The NFκB recognition sequence is the underlined region. AAACAATGAGACACCAGGGATTAGATATCAGTACAATG TGCTTCCACA AAGGATCACCAGCAATATTCCAAA<u>GGGAATTCCCC</u>TAG ATCGCATG (SEQ ID NO: 3). In this embodiment, the amplicon sequence is the sequence preceding the underlined region. The NFκB recognition sequence is the underlined region. |
| Nucleic acid oligomers for GAL4 binding | CATGCGACAGCGGAGTTACGTCCAGAAGGACAACATCT TTGACATCGCCTCTTGAATTGCTGCACCAAGGGCTACTG <u>CCGGAGTACTGTCCTCCG</u>CTAGATCGCATG (SEQ ID NO: 4). In this embodiment, the amplicon sequence is the sequence preceding the underlined region. The GAL4 recognition sequence is the underlined region. |
| NF-κB DNA binding domain | MAGPYLQILEQPKQRGFRFRYVCEGPSHGGLPGASSEKNK KSYPQVKICNYVGPAKVIVQLVTNGKNIHLHAHSLVGKHC EDGICTVTAGPKDMVVGFANLGILHVTKKKVFETLEARM TEACIRGYNPGLLVHPDLAYLQAEGGGDRQLGDREKELIR QAALQQTKEMDLSVVRLMFTAFLPDSTGSFTRRLEPVVSD AIYDSKAPNASNLKIVRMDRTAGCVTGGEEIYLLCDKVQK DDIQIRFYEEEENGGVWEGFGDFSPTDVHRQFAIVFKTPKY KDINITKPASVFVQLRRKSDLETSEPKPFLYYPEIKDKEEVD (SEQ ID NO: 5) |
| GAL4 DNA binding domain | MKLLSSIEQACDICRLKKLKCSKEKPKCAKCLKNNWECRY SPKTKRSPLTRAHLTEVESRLERLEQLFLLIFPREDLDMILK MDSLQDIKALLTGLFVQDNVNKDAVTDRLASVETDMPLT LRQHRISATSSSEESSNKGQRQLTVS (SEQ ID NO: 6) |
| NFκB recognition sequence | GGGAATTCCC (SEQ ID NO: 7) |
| NF-κB recognition sequence | GGGAAATTCCC (SEQ ID NO: 8) |
| NF-κB recognition sequence | GGGACTTTCC (SEQ ID NO: 9) |
| NF-κB consensus sequence | GGGRNNYYCC (SEQ ID NO: 10) (R = purine; Y = pyrimidine) (N = any nucleotide) |
| Gal4 recognition sequence | CGGAGTACTGTCCTCCG (SEQ ID NO: 11) |
| Gal4 consensus sequence | CGGNNNNNNNNNNNNCCG (SEQ ID NO: 12) (N = any nucleotide) |
| RelA/c-Rel consensus sequence | HGGARNYYCC (SEQ ID NO: 13) (H = A, C or T; R = purine; Y = pyrimidine) |
| Cro repressor recognition sequence | TCTATCACCGCGGGTGATAAA (SEQ ID NO: 14) |
| Lac repressor recognition sequence | GAATTGTGAGCGCTCACAATT (SEQ ID NO: 15) |
| GCN4 recognition sequence | AGTGACTCAT (SEQ ID NO: 16) |
| Opaque-2 recognition sequence | TGTCATTCCACGTAGATGAAAA (SEQ ID NO: 17) |
| Opaque-2 recognition sequence | TCCACGTAGA (SEQ ID NO: 18) |
| Lex-A recognition sequence | CTGTATATATATACAG (SEQ ID NO: 19) |

TABLE 1-continued

Exemplary Nucleic Acid Oligomer, Nucleic Acid Interacting Motif and Nucleic Acid Interacting Motif Recognition Sequences

| | |
|---|---|
| TGA1a recognition sequence | GACGTC (SEQ ID NO: 20) |
| EGR-1 or Zif 268 recognition sequence | GCGTGGGCGT (SEQ ID NO: 21) |

5.2.4 Cells

Cells to be used in the methods provided herein may be primary cells, secondary cells or immortalized cells, of any cell type and origin. In some embodiments, cells are of mammalian origin, including human. In some embodiments, cells are of different cell types. In other embodiments, cells are from a substantially homogeneous population of cells. The methods of the invention allow analysis of large numbers of cell samples contained, for example, in 42-, 96-, 384-, or 1536-well assay plates.

The methods provided herein may be carried out using any cell types that can be grown in standard tissue culture plastic ware. Such cell types include all normal and transformed cells derived from any recognized sources, for example, mammalian, plant, bacterial, viral or fungal. In particular embodiments, cells are of mammalian (human or animal, such as rodent or simian) origin. In some embodiments, the cells are of human origin. In some embodiments, the cells are of rodent origin. In some embodiments, the cells are of murine origin. In some embodiments, mammalian cells may be of any organ or tissue origin (e.g., brain, liver, lung, heart, kidney, skin, muscle, bone, bone marrow or blood) and of any cell types. Suitable cell types for use in the methods provided herein include, but are not limited to, fibroblasts, basal cells, epithelial cells, endothelial cells, platelets, lymphocytes, T-cells, B-cells, natural killer cells, reticulocytes, granulocytes, monocytes, mast cells, neurocytes, neuroblasts, cytomegalic cells, dendritic cells, macrophages, blastomeres, endothelial cells, tumor cells, interstitial cells, Kupffer cells, Langerhans cells, littoral cells, tissue cells such as muscle cells and adipose cells, enucleated cells, and the like.

Selection of a particular cell type and/or cell line to develop a particular assay in accordance with the methods described herein can readily be performed by one of ordinary skill in the art, and will be governed by several factors such as the nature of the cellular process to be studied and the intended purpose of the assay. For example, selection of the cell line will depend in part on whether the protein being studied that acts on the substrate (the transfected detectable target protein) is endogenously present in the cell. In some embodiments, an assay developed for primary screening (i.e., first round(s) of screening) of test compounds that modulate a cellular process may be performed using established stable cell lines, which are commercially available and usually relatively easy to grow. In other embodiments where an assay is to be used later in the drug development process, the assay may be performed using primary or secondary cells, which are often more difficult to obtain, maintain, and/or to grow than immortalized cells but which represent better experimental models for in vivo situations.

In some embodiments, the methods described herein comprise a step of starving the cells before contacting the cells with test compound. Cell starvation may be particularly useful when the cellular process to be assayed is phosphorylation by one or more protein kinases, and the protein kinase(s) of interest are not constitutively active. Starving interrupts the normal cycle of cellular growth and division, places the cells in a resting (inactivated) state, and brings the cells' phosphorylation level to a baseline. Starving the cells may be performed by any suitable method, for example by culturing the cells in a medium without serum or growth supplements.

In some embodiments of the methods described herein, the cells may be genetically engineered to express the detectable protein comprising the target protein and the nucleic acid interacting motif. Expression vectors can be introduced into the host cell for expression by any method known to one of skill in the art without limitation. Such methods include, but are not limited to, e.g., direct uptake of the molecule by a cell from solution; or facilitated uptake through lipofection using, e.g., liposomes or immunoliposomes; particle-mediated transfection; etc. See, e.g., U.S. Pat. No. 5,272,065; Goeddel et al., eds, 1990, Methods in Enzymology, vol. 185, Academic Press, Inc., CA; Krieger, 1990, Gene Transfer and Expression—A Laboratory Manual, Stockton Press, NY; Sambrook et al., 1989, Molecular Cloning—A Laboratory Manual, Cold Spring Harbor Laboratory, NY; and Ausubel et al., eds., Current Edition, Current Protocols in Molecular Biology, Greene Publishing Associates and Wiley Interscience, NY. Useful promoters for use in expression vectors include, but are not limited to, a metallothionein promoter, a constitutive adenovirus major late promoter, a dexamethasone-inducible MMTV promoter, a SV40 promoter, a MRP pol III promoter, a constitutive MPSV promoter, an RSV promoter, a tetracycline-inducible CMV promoter (such as the human immediate-early CMV promoter), and a constitutive CMV promoter. The expression vectors should contain expression and replication signals compatible with the cell in which the detectable protein is to be expressed. Expression vectors useful for expressing the detectable proteins described herein include viral vectors such as retroviruses, adenoviruses and adenoassociated viruses, plasmid vectors, cosmids, and the like.

Any mammalian cell known by one of skill in the art to be useful for expressing a recombinant polypeptide, for example, Chinese hamster ovary (CHO) cells, HeLa cells, A375 cells, HEK293 or LnCap cells, can be used to express the detectable protein comprising the target protein and the nucleic acid interacting motif. When the target protein is expressed in the appropriate host cell, it can exhibit post-translational modification that is present in native protein and is therefore expected to have the structure and function of a native protein.

5.3 Kits

Also provided herein is a kit for screening candidate molecules or test compounds that modulates a cellular process, wherein the cellular process modifies a target protein. Such a kit may comprise the cell line transfected with the detectable target protein that serves as the detectable substrate in the cellular assay. Such a kit may further comprise an antibody which specifically binds to a target protein that has been modified as a result of the cellular process. The antibody is optionally immobilized onto a solid support or a container, such as a well in a multiwell plate. In some embodiments, the kit further comprises a detectable nucleic acid oligomer; and a target protein capable of being "tagged" by the nucleic acid oligomer. Where the nucleic acid oligomer is detectable by qPCR, the kit may additionally include a PCR primer capable of recognizing a PCR initiation sequence in the nucleic acid oligomer. Such a kit may be used to carry out the methods of identifying test compounds which modulate a cellular process as described above.

In another embodiment, the kit may be used for detecting the presence of a target protein that has been modified as a result of a cellular process. Such a kit may be used as a diagnostic kit for testing biological samples for the presence of a certain molecule, whether a chemical compound, peptide or protein, that modulates the cellular process, or induces a cellular process that results in the modification of the target protein. In one example, the kit comprises an antibody, which specifically binds to a target protein that has been modified as a result of the cellular process, immobilized to a solid surface; a detectable protein comprising a target protein and a nucleic acid interacting motif capable of being tagged by the nucleic acid oligomer; and a detectable nucleic acid oligomer. The kit may optionally further comprise a PCR primer capable of recognizing a PCR initiation sequence in the nucleic acid oligomer to allow for qPCR amplification.

6. EXAMPLES 6.1 Example 1: Construction of NF-κB and Kinase Fusion Protein

Expression Vector for Constitutive Expression:

The following genetic elements were cloned into the backbone of a generic bacterial plasmid pGEM by gene synthesis followed by restriction digest and subsequent ligation using standard molecular biology techniques. Listed from 5'end to 3'end, they are:

the CMV (Cytomegalovirus) enhancer/promoter region to allow strong, constitutive expression in many cell types;

a chimeric intron composed of the first intron of the human β-globin gene and the intron that is between the leader and the body of an immunoglobulin gene heavy chain variable region (transfection studies have demonstrated that the presence of an intron flanking the cDNA insert frequently increases the level of gene expression);

the DNA-binding domain of the yeast GAL4 or the human NF-κB transcriptional activators (see Table 1) fused in-frame with the TEV (Tobacco Etch Virus) protease recognition sequence followed by a multiple cloning region with several unique restriction sites;

the SV40 (Simian Virus 40) late polyadenylation signal for enhanced mRNA stability and translation;

the pMB1 origin of replication for propagation in $E.\ coli$; and the Ampicillin resistance ($Amp^R$) gene for selection/propagation in $E.\ coli$.

Expression Vector for Inducible Expression:

pcDNA™5/TO (Invitrogen Cat No. K1020-01) which is designed to be used with the T-REx™ system (Invitrogen Cat No. K1020-02) was also used to clone the proteins listed in 5.1.1 in order to be able to control the level of expression of detectable protein in a cell so as not to perturb the cell system. This vector contains two tetracycline operator 2 ($TetO_2$) sites within the CMV promoter which allows for tetracycline-regulated expression. The $TetO_2$ sites serves as binding sites for four Tet repressor molecules expressed in the pcDNA™6/TR. Binding of the Tet repressor represses expression of the detectable protein in the absence of tetracycline. Addition of tetracycline leads to derepression and expression of the detectable protein. The expression of the detectable protein may be controlled either by adjusting the amount of tetracycline present in the cells or by adjusting the ratio of pcDNA™5/TO and pcDNA™6/TR being co-transfected into the cell.

6.1.1 Cloning of Proteins

The sequences encoding full length human kinase Mek1 (GenBank Accession No. NP_002746.1) (SEQ ID NO.: 22), full length human Erk1 (Ref Seq. P27361) (SEQ ID NO.: 23), full length human kinase Akt1 (GenBank Accession No. NP_005154.2) (SEQ ID NO.: 24), full length human transcription factor FKHR/FOXO1 (GenBank Accession No. NP_002006) (SEQ ID NO.: 25), amino acids 1-787 of human Ack1/Tnk2 (Ref Seq Q07912) (SEQ ID NO.: 26), the full length Aurora Kinase A (Ref Seq O14965) (SEQ ID NO.: 27), the full length human Src (Ref Seq P12931) (SEQ ID NO.: 28), the full length human pro-apoptotic protein BAD (Ref Seq CAG46757) (SEQ ID NO.: 29), the full length human histone H3 (Ref Seqs P68431 and Q71DJ3) (SEQ ID NO.: 30), amino acids 142-540 of the human androgen receptor (AR) (Ref Seq P10275) (SEQ ID NO.: 31), the full length human transcription factor STAT5A (P42229) (SEQ ID NO.: 32), the full length transcription factor STAT6 (P42226) (SEQ ID NO.: 33) and full length cyclin B1 (Ref Seq 14635) (SEQ ID NO.: 34) were obtained from reverse translation, and each fused in-frame with the sequence encoding amino acids 35-36 (MetAla) and amino acids 41-359 of the human DNA-binding domain NF-κB (SEQ ID NO: 5), also obtained from reverse translation. Corresponding catalytically inactive kinases were also cloned, by introducing to the above wild type sequence, a mutation to the catalytic residue of the kinase domain. Thus, the sequences encoding the following missense mutations (with specific amino substitutions described in parenthesis) encoding full length human Mek1 (K97A), full length Erk1 (K71R), full length Akt1 (K179A), full length Ack1/Tnk2 (K158R), full length Aurora kinase A/AurKA (K162R), full length Src (K298R) and amino acids 142-540 of the androgen receptor/AR (Y534F) were obtained from reverse translation and each fused in-frame with the sequence encoding SEQ ID NO:5, also obtained from reverse translation. The catalytically inactive kinases were constructed to be passive acceptors of phosphate groups that would not exert downstream effects and that would therefore only minimally perturb the host's cell system.

Sequences were cloned by restriction digestion followed by ligation using standard molecular cloning protocols. The sequence of the clones was verified by ABI sequencing.

The level and quality of expression of every DNA construct were analyzed by SDS-PAGE/Western blotting using antibodies raised against GAL4 and NF-κB (Santa Cruz Biotechnology).

6.1.2 Construction of Nucleic Acid Oligomer

Random sequences were generated and used to design the amplicon sequence using the software Primer Express® (ABI). The amplicon sequence was BLAST searched against the human kinome, and against other amplicon sequences and selected based on least similarity to the sequences in the BLAST search. The selected amplicon sequence was sent to ABI and the appropriate primer and qPCR fluorescent probe were prepared by ABI. The amplicon sequence was further modified by the addition of the GAL4 or NF-κB recognition sites, to create the complete nucleic acid oligomer. The oligonucleotide was cloned into bacterial plasmid, and the oligomer was replicated using PCR.

6.2 Example 2: Phospho-Mek1 Cellular Assay

In this cellular assay, compounds were tested for their ability to inhibit Braf, by measuring the phosphorylation of Mek1, a direct kinase substrate of Braf. A375 cells expressing the constitutively active Braf V600E mutation were plated at a density of 3e5 cells/mL in a 10 cm plate and transfected with expression plasmid encoding detectable protein (16 μg) in 1 mL OPTI-MEM buffer (GIBCO/Invitrogen) with 40 μL Lipofectamine 2000 (Invitrogen) and incubated at 37° C. for 18-22 h. On the following day, media was removed and cells washed with PBS, trypsinized then quenched with M3 media (DMEM containing 10% FBS). Cells were counted and resuspended in M3 complete media to a density of 5e6 cells/mL and then plated at 50,000 cells/well/100 μL into a 96-well plate and incubated at 37° C. for 3h. Media was then removed and starvation media (0.5% FBS/DMEM) was added to the wells and allowed to incubate overnight. On the following day, the cells were incubated with compound in M3 starvation media and incubated at 37° C. for 2 hours.

For the protein extraction step, media was removed from the wells, 50 μL of extraction buffer containing M-PER (Pierce)/150 mM NaCl/10 mM DTT/1x Complete™ EDTA-free (Roche) antiprotease mixture/250 nM okadaic acid) added and the plate shaken in the cold room for 30 minutes at maximum speed. The cells were centrifuged at 3000 rpm for 20 minutes. 30 μL of supernatant were collected and pipetted into a chilled polypropylene plate containing 10 μL of 4× protein stabilizing cocktail (Pierce Cat No. 89806), mixed, and two 10 μL alioquots were withdrawn and the plates were frozen at −80° C. and reserved for the binding assay. Lysate dilution was carried out in two steps. The 96-well plate containing 10 μL extract aliquot was thawed at room temp, and 40 microliters of a solution of 0.1% BSA /1× PBS 0.05% Tween with 2 nM nucleic acid tag serving as the NF-κB probe was added, and mixed by orbital shaking at 450 rpm at room temp for 10 min. Then 270 microliters of a solution of 20 microgram per mL sheared salmon sperm DNA in 0.1% BSA/1× PBS 0.05was added, and mixed gently by pipetting up and down.

As a first step in the phospho-Mek1 detection assay, 2.5 μg anti-phospho-MEK 1/2 (Ser217/221) antibody was immobilized for each 100 μL protein G beads (Invitrogen Dynabeads-Protein G (Cat #100-04D)) in PBST (1× PBS/0.05% Tween 20) and rotated at room temperature for about 45 min, after which 1% BSA/0.02% sodium azide was added to the antibody/bead mixture and rotated at 4° C. overnight. On the following day, beads were pelleted then washed/blocked and resuspended in 1-2×2% BSA/PBST and plated out onto a 96-well polypropylene plate at half the original stock concentration. The phospho-MEK1 binding assay was carried out on a separate plate containing 25 μL of beads and 100 μL 2% BSA/PBST which was shaken until the addition of cell lysate. For the binding assay, beads were first pelleted and the buffer aspirated, and then 100 μL of diluted lysate was added to each well and the plate was shaken at room temperature for one hour. After the binding step, the beads were pelleted for 4 minutes, the buffer aspirated and 150 μL of PBST was added. The plate was briefly shaken and then pelleted over a magnet and then washed two to four times with wash buffer (1× PBS/0.05% Tween 20) to remove unbound proteins. After the final wash, the beads were resuspended in 150 μL of IgG elution buffer (Pierce Cat No. 21004) supplemented with Tween 20 to 0.05% and incubated at room temperature with shaking for 60 minutes. After pelleting the beads, 50 μL of the eluted mixture was removed, and added to 30 μL of 200 mM Tris base, mixed well, and then transferred to the DNA detection assay. For qPCR, 2.5 μL was transferred to 7.5 μL of mastermix with appropriate primers and probes (Applied Biosystems).

Alternatively, the binding assay may be carried out in the absence of the nucleic acid oligomer, which may be added later after the wash step removing the unbound proteins. Comparable results were obtained for alternative methods of antibody immobilization: immobilization of biotin-protein G (Pierce) on a strepavidin support, desthiobiotin labeled antibodies, antibodies attached to biotin through a cleavable disulfide linker, and immobilization of biotinylated antibodies on magnetic streptavidin M-280 beads (Invitrogen).

The binding assay was also run using anti-total-Mek1 antibody to normalize the amount of measured phospho-Mek1 across wells. The anti-phospho Mek assay was validated using known Braf inhibitors in the literature: BAY-43-9006, PLX-4720, Chir-265.

FIG. 3 shows the $IC_{50}$s obtained for BAY-43-9006, PLX-4720, Chir-265 against Braf using the above protocol, with CI-1040 also tested as a negative control.

6.3 Example 3: Phospho-Akt1 Cellular Assay

As shown in the diagram in FIG. 2, the PIK3CA kinase mediates signaling through two separate pathways, e.g., by direct activation of the kinase substrates FRAP1 (the kinase domain of mTOR), or other less-studied kinases known as "PDK2" in the literature and PDPK1, both of which in turn phosphorylate Akt. Since FRAP1 and PDPK1 each activate Akt1 through unique phosphorylation sites (with FRAP1 phosphorylating serine at amino acid 473 of the Akt1 kinase and PDPK1 phosphorylating threonine at amino acid 308 of the Akt kinase), the activation of each pathway may be isolated and tested using the anti-phospho antibodies specific to each phosphorylation site. Therefore, using this cellular assay, compounds were interrogated for their inhibitory mechanism not only against PIK3CA but also against FRAP1 or PDPK1, by measuring site-specific phosphorylation of Akt. The protocol described in Example 1 was followed, except that the cell line Hek 293 was used and plated at a density of 5e5/mL. For the phospho-Akt1 detection step, an anti-phospho Akt (Ser473) antibody (an antibody directed against a peptide containing phosphorylated serine at amino acid 473 of the Akt1 kinase) was used to measure inhibition through the FRAP pathway and the anti-phospho Akt1 (Thr308) antibody (an antibody directed against a peptide containing phosphorylated threonine at amino acid 308 of the Akt1 kinase) was used to measure inhibition through the PDPK1 pathway. A binding assay using anti-total Akt1 antibody was also run in parallel to normalize the amount of measured phospho-Akt1 across wells.

The anti-phospho-Akt1 cellular assay was validated using known selective PIK3CA inhibitors in the literature such PI103, ZSTK-474, wortmannin and PIK-93 and a known PDPK1 inhibitor in the literature, BX-795.

FIG. 4 shows the $IC_{50}$s obtained from the anti-phospho Akt1 (Ser473) and the anti-phospho Akt (Thr308) assays for PI103, ZSTK-474 and BX-795. The cellular assays show PI103 as having a nearly equipotent $IC_{50}$ through the FRAP1 and PDPK1 pathways, which indicates that PI103 works as a selective PIK3CA inhibitor, as established in the literature. Similarly, the cellular assays show both ZSTK-474 and wortmannin as having nearly equipotent $IC_{50}$s in each of the assays interrogating the FRAP1 or PDPK1 pathway, which is consistent with the literature establishing ZSTK-474 and wortmannin as selective PIK3CA inhibitors. In contrast, BX-795 which is a compound known in the literature to specifically inhibit PDPK1, is shown in the cellular assays as selectively inhibiting PDPK1 over FRAP1 (where $IC_{50}$ of BX-795 against FRAP1 is much greater than the $IC_{50}$ obtained for this compound against PDPK1).

The following compounds were also tested in the anti-phospho-Akt1 (Ser473) cellular assays: TG-100-115, a compound known in the literature to inhibit PIK3CG (the gamma isoform of PI3KC); radicicol, a known HSP90 inhibitor and triciribine, a known inhibitor of Akt1 phosphorylation and the dose response curves obtained for each are shown in FIG. 5. The results for BX-795 and TG-100-115 show that the phospho-Akt1 (Ser473) assay is insensitive to PDPK1 and PIK3CG inhibitors. The result for radicicol shows that the assay is partially sensitive to HSP90 inhibition, and that the pAkt inhibitor triciribine displays a dose response curve that is similar to radicicol.

Triciribine and radicicol were also tested in the anti-phospho-Akt (Thr308) cellular assays (FIG. 6) and the dose response curves show that both compounds could only partially inhibit Thr308 phosphorylation.

6.4 Example 4: PIK3CA Phospho-FOXO1 Cellular Assay

In this cellular assay, compounds were tested for their ability to inhibit Akt1, by measuring the phosphorylation of the transcription factor FOXO1 (also known as FKHR), a direct kinase substrate of Akt1. The protocol described in Example 1 was followed, except that the cell line Hek 293 was used and plated at a density of 5e5/mL. For the phospho-FOXO1 detection step, an anti-phospho-FOXO (Thr24) antibody (an antibody directed against phosphorylated threonine at amino acid 24 of the FOXO1 transcription factor) was used and antibody against NF-κB was used for total capture to normalize the amount of phospho-FOXO1 measured across wells.

FIG. 7 shows the dose response curves obtained for GSK-690693, a known Akt1 inhibitor, as well as for PI103 and BX-795, which are compounds that are known in the literature to inhibit PIK3CA and PDPK1, respectively. FIG. 7 shows that the anti-phospho-FOXO1 (Thr24) assay is more sensitive to Akt1 inhibitors such as GSK-6900693 (exhibiting an $IC_{50}$ of 165 nM) compared to PIK3CA inhibitors such as PI103 (exhibiting an $IC_{50}$ of 762 nM) and therefore permits differentiation of direct Akt1 inhibition from upstream inhibition of PIK3C.

The assays described in Examples 3 and 4 therefore represent a collection of assays of the invention that permit the interrogation of the mechanism of action of compounds that act in the PIK3CA pathway depicted in FIG. 2.

6.5 Example 5: Phospho-AurkA Cellular Assay

In this assay, compounds were tested for their ability to inhibit the autophosphorylation of Aurora A. HeLa cells were plated at a density of 5e6/mL in a 10 cm plate and tranfected with expression plasmid encoding detectable protein (8 μg) in 2 mL OPTI-MEM buffer (GIBCO/Invitrogen) with 40 μL Lipofectamine 2000 (Invitrogen) and incubated at 37° C. for 18-22 h. On the following day, media was removed and cells washed with PBS, trypsinized then quenched with M3 media (DMEM containing 10% FBS). Cells were counted and resuspended in M3 complete media to a density of 5e6mL and then plated at 50,000 cells/well/50 μL into a 96-well plate and incubated at 37° C. for 4 h.

For the bead preparation, which is carried out the evening before the binding experiment, protein G beads (Invitrogen, Dynabeads-Protein G (Cat #100-04D)) were washed in a 15 mL tube, pelleted over a magnet, and then washed again in 1× PBS/0.05% Tween 20. The beads were then resuspended and to it was added anti-phospho Aurora A (Thr288) antibody at a ratio of 2.5 μg antibody per 100 μL protein G beads and rotated at room temperature for about 45 min, after which 1% BSA/0.02% sodium azide was added to the antibody/bead mixture and rotated at 4° C. overnight. For all of the assays disclosed herein, the optimal antibody-to-bead ratio was determined empirically by testing several antibody concentrations and selecting the concentration yielding the highest signal ratio obtained from untreated cells (phosphorylated) versus treated cells (treated with specific inhibitors that inhibit phosphorylation of target protein).

On the following day after the overnight incubation, the cells were incubated with test compound in M3 and incubated at 37° C. for 2 hours. For the protein extraction, media was removed from the wells, 50 μL of extraction buffer containing M-PER (Pierce)/150 mM NaCl/10 mM DTT/1× Complete™ (Roche) antiprotease mixture/250 nM okadaic acid) added and the plate shaken in the cold room for 30 minutes at 3000 rpm. The cells were centrifuged at 3000 rpm for 20 minutes. 30 μL of supernatant were collected and pipetted into a chilled polypropylene plate containing 10 μL of 4× protein stabilizing cocktail (Pierce Cat No. 89806).

Lysate dilution was carried out in two steps. The cell extract was first diluted two-fold with 1× PBS/0/05% Tween/0.1% BSA in the presence of 0.5 nM a nucleic acid oligomer serving as the NF-κB probe and 80 μg/mL salmon sperm DNA, and allowed to incubate for about 30 minutes at rt. At the second dilution step, the diluted extract was diluted another 7.5× in 1× PBS/0.05% Tween/0.1% BSA and 40 μg/mL salmon sperm DNA, so that the final dilution yielded at 15-fold diluted stock containing 0.03 nM nucleic acid oligomer and 40 μg/mL salmon sperm DNA.

Also on the following day after the bead preparation, the beads were pelleted and then washed/blocked and resuspended in twice the original volume of 1× PBS/0.05% Tween 20/2% BSA and then plated out at half the original stock concentration onto a 96-well plate at a volume of 50 μL per well containing 1× PBS/0.05% Tween 20/2% BSA. 50 μL of the cell lysate was then added to each well, and the plate was shaken for 1 hour at room temperature.

After the binding reaction, the beads were pelleted for 4 minutes, the buffer aspirated and 150 μL of PBST was added to each well. The plate was shaken and then pelleted over a magnet and then washed two to four times with PBST to remove unbound proteins. At the final wash, the beads were transferred to a new plate on magnets. The final was buffer was removed with aspirator, and 150 μL of IgG elution buffer was added (Pierce Cat No. 21004) containing 0.05% Tween 20 and incubated at room temperature with shaking for 30 min.

Alternatively, the binding assay may be carried out in the absence of the nucleic acid oligomer, which may be added later after the wash step removing the unbound proteins. The binding assay was also run using anti-Aurora A antibody to normalize the amount of measured phospho-AurkA across wells.

For the qPCR detection step, 50 μL of eluate was transferred to a new 384-well polypropylene plate. To it was added 30 μL of a neutralization buffer (200 mM Tris pH 9.4/0.05% sodium azide) to neutralize the pH. 2.5 μL of the neutralized eluate was transferred to a PCR plate containing 7.5 μL of qPCR reaction mixture (a custom TaqMang® Master Mix (Applied Biosystems) and read using 7900 Real Time PCR Instrument (Applied Biosystems). $IC_{50}$ curves were obtained for MLN-8054 (a known AurkA inhibitor in the literature), AZD-1152HQPA (a known AurkB inhibitor in the literature) and VX-680 (a pan Aurora inhibitor).

6.6 Example 6: Phospho-Erk1 Cellular Assay

In this assay, compounds were tested for their ability to inhibit Mck1 by measuring the phosphorylation of Erk1 following the protocol described in Example 4. A vector encoding catalytically inactive Erk1-NFkB detectable protein was transfected in A375 cells, and for the binding assay, an anti-phospho Erk1 (Thr202/Tyr204) antibody was used. The binding assay was also run using anti-total Erk1 antibody to normalize the amount of measured phospho-Erk1 across wells. $IC_{50}$ curves were obtained for known Erk1 inhibitors in the literature, including CI-1040 (PD0325901).

6.7 Example 7: Phospho-Tnk2 Cellular Assay

In this assay, compounds were tested for their ability to inhibit autophosphorylation of Tnk2 (also known as Ack1) following the protocol described in Example 4. A vector encoding Tnk2-NFkB detectable protein was transfected into Hek 293 cells and for the binding reaction, an anti-phosphotyrosine antibody was used to detect the phosphorylation of Tnk2 at Tyr284. The binding reaction was also run using anti-total NFkB antibody to normalize the amount of measured phospho-Tnk2 across wells.

6.8 Example 8: Phospho-Src Cellular Assay

In this assay, compounds were tested for their ability to inhibit autophosphorylation of Src following the protocol described in Example 4. A vector encoding Src-NFkB detectable protein was transfected into Hek 293 cells and for the binding reaction, an anti-phospho tyrosine antibody was used to detected phosphorylation of Src at Tyr416. The binding reaction was also run using anti-total Src antibody to normalize the amount of measured phosphor-Src1 across wells. $IC_{50}$ curves were obtained for known Src inhibitors, including SKI606 (bosutinib), CGP-52421, PD-180970 and BMS-354825 (dasatinib).

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of detecting a protein modified by a cellular process of interest comprising the steps of:
    a) contacting a detectable protein comprising a target protein and a nucleic-acid interacting motif with:
        i) an antibody that specifically binds a target protein that has been modified by the cellular process of interest and does not bind an unmodified form of the target protein; and
        ii) a nucleic acid oligomer comprising a first nucleic acid comprising a reporter function and a second, heterologous nucleic acid sequence that binds the nucleic-acid interacting motif; and
    b) detecting said reporter function in the presence of the nucleic acid oligomer that is bound to the detectable protein which is also bound by the antibody;
    wherein the presence of the nucleic acid oligomer of step (b) indicates the presence of a protein modified by the cellular process of interest.

2. The method of claim 1, wherein the target protein is modified by a cellular process selected from acylation, acetylation, deacetylation, formylation, alkylation, methylation, phosphorylation, dephosphorylation, sulfation, oxidation, reduction, hydroxylation, deamidation, carboxylation, disulfide formation, prenylation, glycation, glycosylation, ubiquitination, sumoylation, proteolysis, racemization and isomerization.

3. The method of claim 1, wherein the cellular process is phosphorylation.

4. The method of claim 1, wherein the target protein is a kinase substrate.

5. The method of claim 4, wherein the modified target protein is phosphorylated at one or more residues, and the antibody is an anti-phospho antibody.

6. The method of claim 4, wherein the modified target protein is phosphorylated at one or more tyrosine residues, and the antibody is an antiphosphotyrosine antibody.

7. The method of claim 4, wherein the modified target protein is phosphorylated at one or more serine residues, and the antibody is an anti-phosphoserine antibody.

8. The method of claim 4, wherein the modified target protein is phosphorylated at one or more threonine residues, and the antibody is an antiphosphothreonine antibody.

9. The method of claim 1, wherein the target protein is a G-coupled protein receptor, an ion channel protein, a nuclear receptor protein, a transcription factor, a kinase, a cytokine, a growth factor, a hormone, an enzyme, an antibody or a small chain variable fragment (scFv).

10. The method of claim 1, wherein the nucleic acid-interacting motif is a DNA-binding domain.

11. The method of claim 1, wherein the DNA-binding domain is a NF-κB DNA binding domain, cro repressor DNA binding domain, lac repressor DNA binding domain, GAL4 DNA binding domain, GCN4 DNA binding domain, Lex-A DNA binding domain, Opaque-2 DNA binding domain or TGA1a DNA binding domain.

12. The method of claim 1, wherein the nucleic acid-interacting motif comprises the amino acid sequence depicted in SEQ ID NO:5 or SEQ ID NO:6.

13. The method of claim 1, wherein the oligomer is between about 50 and 500 nucleotides in length.

14. A method of identifying a test compound which modulates a cellular process, wherein the cellular process modifies a target protein, said method comprising the steps of:
    a) contacting a cell or cell lysate comprising a detectable protein with test compound, wherein the detectable protein comprises the target protein and a nucleic-acid interacting motif;
    b) contacting the detectable protein in said cell or cell lysate with:
        i) an antibody that specifically binds to the target protein that has been modified as a result of the cellular process and does not bind an unmodified form of the target protein; and ii) a nucleic acid oligomer comprising a first nucleic acid sequence comprising a reporter function and a second, heterologous nucleic acid sequence that binds the nucleic-acid interacting motif; and c) detecting said reporter function to determine an amount of nucleic acid oligomer bound to the detectable protein that is also bound by the antibody;

wherein an increase or decrease in the amount of bound nucleic acid oligomer of step (c) detected in the presence of said test compound relative to the amount of bound nucleic acid oligomer detected in the absence of said test compound indicates that the test compound modulates the cellular process.

15. The method of claim 14, wherein the detectable protein is contacted with the antibody before the detectable protein is contacted with the nucleic acid oligomer in step (b).

16. The method of claim 14, wherein the detectable protein is contacted with the antibody after the detectable protein is contacted with the nucleic acid oligomer in step (b).

17. The method of claim 14, wherein the detectable protein is concurrently contacted with the antibody and the nucleic acid oligomer in step (b).

18. The method of claim 14, wherein step (a) comprises contacting a cell comprising the detectable protein.

19. The method of claim 18, wherein the cell transiently expresses the detectable protein.

20. The method of claim 18, wherein the cell stably expresses the detectable protein.

21. The method of claim 18, wherein the cell constitutively expresses the detectable protein.

22. The method of claim 18, wherein the cell inducibly expresses the detectable protein.

23. The method of claim 14, wherein the cellular process is selected from acylation, acetylation, deacetylation, formylation, alkylation, methylation, phosphorylation, dephosphorylation, sulfation, oxidation, reduction, hydroxylation, deamidation, carboxylation, disulfide formation, prenylation, glycation, glycosylation, ubiquitination, sumoylation, proteolysis, racemization and isomerization.

24. The method of claim 14, wherein the cellular process is phosphorylation.

25. The method of claim 24, wherein the target protein is a kinase substrate.

26. The method of claim 25, wherein the modified target protein is phosphorylated at one or more tyrosine residues, and the antibody is an antiphosphotyrosine antibody.

27. The method of claim 25, wherein the modified target protein is phosphorylated at one or more serine residues, and the antibody is an anti-phosphoserine antibody.

28. The method of claim 25, wherein the modified target protein is phosphorylated at one or more threonine residues, and the antibody is an antiphosphothreonine antibody.

29. The method of claim 14, wherein the target protein is a G-coupled protein receptor, an ion channel protein, a nuclear receptor protein, a transcription factor, a kinase, a cytokine, a growth factor, a hormone, an enzyme, an antibody or a small chain variable fragment (scFv).

30. The method of claim 14, wherein the nucleic acid-interacting motif is a DNA-binding domain.

31. The method of claim 14, wherein the DNA-binding domain is a NF-KB DNA binding domain, cro repressor DNA binding domain, lac repressor DNA binding domain, GAL4 DNA binding domain, GCN4 DNA binding domain, Lex-A DNA binding domain, Opaque-2 DNA binding domain or TGA1a DNA binding domain.

32. The method of claim 14, wherein the nucleic acid-interacting motif comprises the amino acid sequence depicted in SEQ ID NO:5 or SEQ ID NO:6.

33. The method of claim 14, wherein the oligomer is between about 50 and 500 nucleotides in length.

34. The method of claim 25, wherein the kinase substrate is Mek 1 and step (a) further comprises preparing a positive control sample whereby the cell or cell lysate comprising a detectable protein is contacted with a Braf inhibitor instead of test compound.

35. The method of claim 34, wherein the Braf inhibitor is selected from BAY-43-9006, PLX-4720, Chir-265.

36. The method of claim 25, wherein the kinase substrate is Akt1 and the antibody binds to phosphorylated Akt.

37. The method of claim 36, wherein the antibody binds to Akt1 phosphorylated at Ser473 or Thr308.

38. The method of claim 37, wherein the antibody binds to Akt1 phosphorylated at Thr308.

39. The method of claim 37, wherein the antibody binds to Akt1 phosphorylated at Ser473.

40. The method of claim 25, wherein the kinase substrate is FRAP1 or PDPK1 and step (a) further comprises preparing a positive control sample whereby the cell or cell lysate comprising a detectable protein is contacted with a PIK3CA inhibitor instead of test compound.

41. The method of claim 40, wherein the PIK3CA inhibitor is selected from PI103, ZSTK-474, wortmannin and PIK-93.

42. The method of claim 25, wherein the kinase substrate is AKT1 and step (a) further comprises preparing a positive control sample whereby the cell or cell lysate comprising a detectable protein is contacted with a PDPK1, FRAP1 or mTOR inhibitor instead of test compound.

43. The method of claim 42, wherein the PDPK1 inhibitor is BX-795.

44. The method of claim 25, wherein the kinase substrate is FOXO 1 and the antibody binds to the phosphorylated FOXO 1.

45. The method of claim 44, wherein the antibody binds to FOXO 1 phosphorylated at Thr24.

46. The method of claim 25, wherein step (a) further comprises preparing a positive control sample whereby the cell or cell lysate comprising a detectable protein is contacted with an AKT1 inhibitor instead of test compound.

47. The method of claim 46, wherein the Aka inhibitor is GSK-690693.

48. The method of claim 14, further comprising contacting the cell or cell lysate comprising a detectable protein with at least two concentrations of test compound and calculating the $IC_{50}$ of the test compound.

49. The method of claim 14, wherein an increase in the amount of bound nucleic acid oligomer of step (c) detected in the presence of said test compound relative to the amount of bound nucleic acid oligomer detected in the absence of said test compound indicates that the test compound agonize the cellular process.

50. The method of claim 14, wherein a decrease in the amount of bound nucleic acid oligomer of step (c) detected in the presence of said test compound relative to the amount of bound nucleic acid oligomer detected in the absence of said test compound indicates that the test compound inhibits the cellular process.

51. The method of claim 1, wherein the nucleic acid oligomer comprises (a) a first nucleic acid sequence that is a PCR amplification sequence, and (b) a second nucleic acid sequence that binds the nucleic acid-interacting motif, wherein the first nucleic acid sequence is heterologous to the second nucleic acid sequence.

52. The method of claim 1, further comprising qPCR amplifying the nucleic acid oligomer that is bound to the detectable protein.

53. The method of claim 1, wherein the nucleic acid oligomer is radiolabeled, fluorescently labeled or biotinylated.

54. The method of claim 1, wherein the antibody is immobilized on a multiwell plate.

55. A kit comprising:
a) a cell comprising a detectable protein, wherein the detectable protein comprises a protein modified by a cellular process and a nucleic-acid interacting motif;
b) a nucleic acid oligomer comprising a nucleic acid sequence that binds the nucleic-acid interacting motif; and
c) an antibody that specifically binds the detectible protein modified by a cellular process and does not bind an unmodified form of the detectible protein.

56. The kit of claim 55, wherein the cellular process is phosphorylation.

57. The method of claim 2, wherein the nucleic acid oligomer comprises (a) a first nucleic acid sequence that is a PCR amplification sequence, and (b) a second nucleic acid sequence that binds the nucleic acid-interacting motif, wherein the first nucleic acid sequence is heterologous to the second nucleic acid sequence.

58. The method of claim 3, wherein the nucleic acid oligomer comprises (a) a first nucleic acid sequence that is a PCR amplification sequence, and (b) a second nucleic acid sequence that binds the nucleic acid-interacting motif, wherein the first nucleic acid sequence is heterologous to the second nucleic acid sequence.

* * * * *